US009850528B2

(12) United States Patent
Santourlidis

(10) Patent No.: US 9,850,528 B2
(45) Date of Patent: Dec. 26, 2017

(54) DETERMINATION OF THE NORMALIZED DEGREE OF DNA METHYLATION

(75) Inventor: Simeon Santourlidis, Neuss (DE)

(73) Assignee: HEINRICH-HEINE-UNIVERSITÄT DÜSSELDORF, Düsseldorf (DE)

( * ) Notice: Subject to any disclaimer, the term of this patent is extended or adjusted under 35 U.S.C. 154(b) by 0 days.

(21) Appl. No.: 13/145,164

(22) PCT Filed: Jan. 21, 2010

(86) PCT No.: PCT/EP2010/050687
§ 371 (c)(1),
(2), (4) Date: Jul. 19, 2011

(87) PCT Pub. No.: WO2010/084154
PCT Pub. Date: Jul. 29, 2010

(65) Prior Publication Data
US 2011/0318739 A1  Dec. 29, 2011

(30) Foreign Application Priority Data
Jan. 22, 2009 (EP) .................................... 09151141

(51) Int. Cl.
C12Q 1/68 (2006.01)
(52) U.S. Cl.
CPC ......... *C12Q 1/6858* (2013.01); *C12Q 1/6886* (2013.01); *C12Q 2600/154* (2013.01)
(58) Field of Classification Search
None
See application file for complete search history.

(56) References Cited

U.S. PATENT DOCUMENTS

| 5,854,033 A | 12/1998 | Lizardi |
| 2006/0019270 A1 | 1/2006 | Yang et al. |
| 2006/0115806 A1 | 6/2006 | McDonald |
| 2006/0194208 A1* | 8/2006 | Tetzner et al. .................... 435/6 |

FOREIGN PATENT DOCUMENTS

| WO | 2006/060308 A2 | 6/2006 |
| WO | 2006/111586 A2 | 10/2006 |
| WO | 2008/130516 A1 | 10/2008 |
| WO | 20081134596 A2 | 11/2008 |
| WO | WO 2008134596 A2 * | 11/2008 |

OTHER PUBLICATIONS

Roman-Gomez et al. Oncogene (2005) 24: 7213-7223.*
GenBank Accession No. M80343.1 for Human transposon L1.2 (Feb. 28, 2000 [online], [retrieved on Dec. 11, 2012], retrieved from the Internet: <URL: www.ncbi.nlm.nih.gov/nuccore/m80343>).*
Trinh et al. Methods (2001) 25: 456-462.*
Iacopetta et al. Cancer Science (2007) 98(9): 1454-1460.*
Bestor, "The DNA methyltransferases of mammals," Human Molecular Genetics, vol. 9, No. 16 Review, pp. 2395-2402 (2000).
Cervoni et al., "Demethylase Activity Is Directed by Histone Acetylation," The Journal of Biological Chemistry, 276 (44): 40778-40787 (Nov. 2, 2001).
Fraga et al., "DMA Methylation: A Profile of Methods and Applications," BioTechniques 33(3):632-649 (Sep. 2002).
Frommer et al., "A genomic sequencing protocol that yields a positive display of 5-methylcytosine residues in individual DNA strands," Proc. Natl. Acad. Sci. USA, 89: 1827-1831 (Mar. 1992).
Gardiner-Garden et al., "CpG Islands in Vertebrate Genomes," J. Mol. Biol. 196: 261-282 (1987).
Hill, "Genome-Wide DNA Methylation Profiling of CpG Islands in Breast Cancer Identifies Novel Genes Associated with Tumorigenicity," Cancer Research, 71(8): 2988-2999 (2011).
Jenuwein, "Re-SET-ting heterochromatin by histone methyltransferases," Trends in Cell Biology, 11(6): 266-273 (Jun. 2001).
Kariya et al., "Revision of consensus sequence of human Alu repeats—a review," Gene, 53:1-10 (1987).
Laird et al., "The Role of DNA Methylation in Cancer Genetics and Epigenetics," Annu. Rev. Genet. 30: 441-464 (1996).
Laird, "The Power and the Promise of DNA Methylation Markers," Nature Reviews Cancer, 3: 253-266 (Apr. 2003).
Razin, "CpG methylation, chromatin structure and gene silencing—a three way connection," The EMBO Journal, 17(17): 4905-4908 (1998).
Roman-Gomez et al., "Repetitive DNA hypomethylation in the advanced phase of chronic myeloid leukemia," Leukemia Research 32: 487-490 (2008).
Schulz, "DNA methylation in urological malignancies (Review)," International Journal of Oncology, 13: 151-167 (1998).
Serman et al., "DNA Methylation as a Regulatory Mechanism for Gene Expression in Mammals," Coll. Antropol., 30(3): 665-671 (2006).
Stirling et al., "Dual DNA/RNA Extraction," Methods in Molecular Biology, vol. 226:PCR Protocols, Second Ed., edited by J.M.S. Bartlett and D. Stirling, Humana Press Inc.(Totowa, NJ), pp. 49-51 (2003).
Tamaru et al., "A histone H3 methyltransferase controls DNA methylation in Neurospora crassa," Nature 414: 277-283 (Nov. 15, 2001).

(Continued)

*Primary Examiner* — Angela M Bertagna
(74) *Attorney, Agent, or Firm* — Christensen, Fonder, Dardi & Herbert PLLC; Peter S. Dardi; Kayla Pascoe

(57) ABSTRACT

The present invention provides oligonucleotides and processes for determining the normalized methylation level of DNA, and for determining the relative methylation level of DNA between at least two samples. The invention makes use of the random distribution of transposons in the genome. The disclosed oligonucleotides and processes are of importance, in particular, for clinical diagnostics.

15 Claims, 1 Drawing Sheet

(56) References Cited

OTHER PUBLICATIONS

Compton, "Nucleic Acid sequence-based amplification," Nature, 350(6313):91-2 (Mar. 7, 1991) (Abstract only).
European Office Action from corresponding European Patent Application No. 10 701 233.8, dated Jun. 17, 2014 (5 pages).
Livak et al.; Analysis of Relative Gene Expression Data Using Real-Time Quantitative PCR and the $2^{13}$ $\Delta\Delta CT$ Method, Methods 25, 402-408, 2001. pp. 1-7.

* cited by examiner

DETERMINATION OF THE NORMALIZED DEGREE OF DNA METHYLATION

CROSS REFERENCE TO RELATED APPLICATIONS

This application is a national stage filing of PCT application number PCT/EP2010/050687 filed on Jan. 21, 2010, which claims priority to European patent application serial number 09151141.0 filed on Jan. 22, 2009, both of which are incorporated herein by reference.

The invention belongs to the field of epigenetics, especially DNA methylation. It provides an amplification process for the detection of epigenetic changes that are relevant, in particular, to clinical diagnostics. Further, specific primers for this amplification process are provided.

Epigenetic mechanisms cause changes in gene expression that are not accompanied by a change of the coding sequence of the genes, but can be inherited, for example, mitotically. The DNA methylation patterns are transferred from the parent cell to the daughter cells in a manner that is coupled to replication. Thus, the inheritance of epigenetic information is ensured. In higher eukaryotes, DNA methylation is the best studied epigenetic mechanism in addition to RNA-associated silencing and histone modification (Serman et al., Coll Anthropol. 2006; 30(3):665-71).

In a fully differentiated healthy cell, the human genome has a specific and substantially invariable DNA methylation pattern, which decisively codetermines gene expression. Genomic regions having a regulative function for transcription are not methylated in many cases, while transcriptionally inactive genomic segments are methylated.

DNA methylation takes place at the cytosine residues of the nucleic acid, preferably at dinucleotides with a cytosine-guanine sequence (CpG). The most important base modification in eukaryotes in methylation at the 5' position of cytosine.

In a tumor cell, which is characterized among others by an increased proliferation rate, an altered gene expression and chromosomal anomalies, the genomic methylation pattern is aberrant (Schulz, DNA methylation in urological malignancies. Int J Oncol. 1998; 151-67). In many relevant reviews in this technical field, it is unanimously agreed that these epigenetic changes hold an immense diagnostically and prognostically relevant potential, the harnessing of which may result in modern methods of early cancer detection, cancer prognosis and follow-up.

However, since chromosomal anomalies occur in tumor tissue, i.e., since this tissue has a different genomic setting as compared to healthy tissue, the basic problem is to determine such an aberrant DNA methylation not only qualitatively, but also quantitatively and in a standardized way. Only such a kind of determination enables a direct comparison between two samples one of which may have chromosomal anomalies.

According to the invention, this object is achieved by the process according to claim 1, and by the advantageous embodiments and further embodiments of the dependent claims. For solving these problems, the present invention provides methods for determining the normalized DNA methylation and methods for determining the relative DNA methylation level between at least two samples.

In a first aspect, a process for determining the normalized DNA methylation level is disclosed, comprising the steps: a) quantitative determination of the presence of a transposon or fragment thereof in a DNA; b) quantitative determination of the presence of at least one differentially methylated C of a CpG dinucleotide within the same transposon or fragment thereof; and c) determination of the normalized DNA methylation level via the values determined in steps a) and b).

The present invention takes advantage of the surprising result that the methylation level of transposons that are randomly distributed over the entire genome can be considered representative of the methylation level of the entire genome. The principle of the invention resides in the quantitative determination, in a first step, of the presence of a transposon (or fragment thereof) in a DNA, for example, from a sample and in the quantitative determination, in a further step, of the presence of at least one differentially methylated cytosine of a CpG dinucleotide within the same transposon (or fragment thereof) in the same DNA. Then, a normalized DNA methylation level that is representative of the whole genome can be determined via the ratio between the determined values.

The methylation of DNA is a postreplicative epigenetic mechanism that is of significant importance to gene regulation in eukaryotes. In eukaryotes, the addition of a methyl group to the carbon atom No. 5 of the cytosine pyrimidine base to form 5-methylcytosine ($^{5m}C$) plays the dominant role. This methyl addition is catalyzed in vivo by a transfer of the methyl group from S-adenosylmethionine (methyl donor) to cytosine (methyl acceptor) by means of DNA methylases (DNMTs) and preferably occurs in cytosines that are localized 5' to a guanine (CpG).

In the vertebrate genome, $^{5m}C$ exclusively occurs in CpG dinucleotides (Bestor. The DNA methyltransferases of mammals. Hum Mol Genet 2000; 2395-2402), and in the human genome, mostly both cytosines of the palindromic CpG dinucleotide are methylated.

Due to evolutionary mechanisms and the tendency of methylcytosine to become deaminated spontaneously, CpG dinucleotides are strongly underrepresented with a frequency of 0.8%, at least in the mammal genome (the average GC content in humans is about 40%, which should lead to a calculated frequency of the CpG dinucleotide of 4%), and usually occur more abundantly only in "CpG islands", which are often localized in the 5'- or 3'-NTR of genes (Gardiner-Garden & Frommer. CpG islands in vertebrate genomes. J Mol Biol 1987; 261-282). The reasons for this limitation to non-coding regions is presumably the increased risk of point mutations by the deamination of $^{5m}C$ to thymine (Laird & Jaenisch. The role of DNA methylation in cancer genetic and epigenetics. Annu Rev Genet 1996; 441-464).

CpG islands have a size of about 500 bp to 4 kb and an increased GC content of >55%. They have a ten to twenty times increased frequency of the dinucleotide 5'-CpG-3'. More than three quarters of all (about 25,000) human genes have CpG islands in their starting regions.

In general, genes having a high transcriptional activity are localized in non-methylated genomic regions. In contrast, in methylated regions, there are genes that are little or not at all transcriptionally active. There is a correlation between DNA methylation and chromatin condensation, since genes in densely packed heterochromatin are generally inactive. Such a denser packing of the chromatin is induced by the deacetylation and methylation of the histones H3 and H4, which leads to a stronger binding of the nucleosomes to the DNA and thus results in a more difficult access to the DNA for the transcription machinery (Jenuwein. Re-SET-ting heterochromatin by histone methyltransferases. Trends Cell Biol 2001; 266-273). The protein MeCP2, which binds to CpG-methylated DNA, can recruit histone deacetylases and initiate the condensation of chromatin (Razin & Razin. CpG methylation, chromatin structure and gene silencing-a threeway connection. EMBO J. 1998; 4905-4908). However, histone methylases are also able to lead DNA methyltransferases into heterochromatic regions and thus to trigger DNA methylation there (Tamaru & Selker. A histone H3 methyl-transferase controls DNA methylation in *Neurospora crassa*. Nature 2001; 277-283). Further, histone acetylation presumably leads to active demethylation of the gene segment in question (Cervoni & Szyf. Demethylase activity is directed by histone acetylation. L Biol. Chem. 2001; 40778-40787).

As mentioned earlier, erroneous DNA methylations are mostly inherited stably to daughter cells and therefore may often be the cause of diseases on the organism level. In particular, tumor cells, for example, often exhibit methylation patterns that significantly deviate from those of healthy tissues. Therefore, it is considered to employ the analysis of the methylation level, for example, for diagnostic applications. Further, a directed modification/correction of the methylation state is also considered for the purpose of gene regulation.

For the analysis of the methylation state of nucleic acids, especially the methylation state of specific CpG sites, bisulfitation with, for example, subsequent amplification/sequencing, which was first described by Frommer et al. (Proc Natl Acad Sci USA. 1992; 89(5):1827-31), has become established. Bisulfitation converts non-methylated cytosine bases of the nucleic acid into uracil bases, while methylated cytosine bases remain unchanged. A survey of various technologies for the analysis of the methylation state of nucleic acids, especially bisulfitation, is found in Fraga et al., Biotechniques. 2002; 33(3):632, 634, 636-49, and Laird, Nat Rev Cancer. 2003; 3(4):253-66. Therefore, depending on the methylation state of the starting nucleic acid, the bisulfitation reaction leads to nucleic acid sequences having different sequences, after the analysis of which, among others by PCR or sequencing, the methylation state of the starting nucleic acid can be concluded.

This analysis of the methylation level of a sample, such as a tissue or bioptate, quickly reaches its limits with conventional methods, whenever a comparison of this sample with another sample is to be performed and the two samples have different genomic settings. Namely, as mentioned above, tumor cells have unbalanced chromosomal anomalies in many cases. These include gains and losses of whole chromosomes, individual chromosome arms and shorter DNA sequence segments. Several studies provide evidence that these genomic instabilities of the tumor cells are caused by a low degree of DNA methylation. The degree of DNA hypomethylation is found to be proportional to the genomic instability and tumor aggressiveness.

The present invention makes use of the surprising result that the methylation level of transposons that are randomly distributed over the entire genome can be considered representative of the methylation level of the entire genome. Thus, a normalized determination of the methylation level of the genome is possible if the quantitative presence of a transposon "as such" is determined in the genome in addition to the quantitative presence of at least one differential methylation within the transposon.

The term "transposon" as used herein refers to a DNA segment of a certain length in the genome. A transposon includes one or more genes and is able to change its place within the genome (transposition). Transposons may be elements whose mobile intermediate is constituted by RNA (retro elements; class I transposon), or elements whose mobile phase is DNA (DNA transposon; class II transposon).

The term "transposon" as used herein always includes fragments of such a transposon. Such fragments of a transposon are produced in the genome in the course of evolution, since a transposon that has "jumped" is not subject to any selection pressure, and thus the original sequence can be changed by mutations in the genome. Thus, rather than the complete transposons, often only partial regions thereof are found in the genome, generated, for example, by another insertion of a transposon or deletions, which are localized in the 5' region in most cases. A "fragment of a transposon" is preferably intended to mean a contiguous region of nucleic acid with a length of $\geq 40$ bp, $\geq 80$ bp, $\geq 100$ bp, preferably $\geq 150$ bp, more preferably $\geq 200$ bp, which has a homology of 75%, 80%, 85%, 90%, 95%, 97%, 98%, preferably 98.5%, 99%, 99.5% and even more preferably 99.7%, 99.9% or more with the corresponding nucleic acid region of the transposon. Such a homology can be determined, for example, by the FASTA algorithm. The terms "transposon" and "transposable element" are interchangeable.

Autonomous DNA transposons consist of DNA sequences coding for the enzyme transposase. Transposase is able to "excise" a transposon from the genome, transport it to a new site within the genome and there insert it into the genome. This process is referred to as "conservative transposition". Examples of DNA transposons include: Ac (activator) transposable elements (autonomous transposon) or Ds (dissociator) transposable elements (non-autonomous transposon without its own transposase).

Retrotransposons represent the majority of eukaryotic transposable elements and have a more complex structure. They are recognized by the host cell as a "normal" DNA sequence within the genome and are thus read by the transcription machinery of the host cell and transcribed into RNA. However, retrotransposons code for a reverse transcriptase, which enables this RNA to be converted to DNA. This transposase also performs the insertion of the generated DNA into the genome of the host cell. This process is referred to as "replicative transposition". Therefore, as long as the retrotransposon remains functional, several copies are produced in the genome.

The number of active transposons in the genome of an organism varies greatly with the species. In the human genome, for example, only a very small proportion of the transposons are active. It is considered that only about 50 LINE transposons (see below) and virtually no DNA transposons are active, so that the number of transposons can be considered almost constant during the lifetime of a human.

There are two main types of retrotransposons: viral and non-viral retrotransposons.

Viral retrotransposons broadly have properties very similar to those of retroviruses. Examples of viral retrotransposons include: Ty transposable elements and *Drosophila* copia transposable elements.

Non-viral retrotransposons represent the majority of all transposons in mammals. As examples, there may be mentioned, in particular: LINEs (long interspersed (transposable) elements), SINEs (short interspersed (transposable) elements), and Alu elements.

In the human genome, approximately 850,000 LINEs and 1,500,000 SINEs occur. The SINEs include the Alu elements, which represent the group of transposable elements that are most frequently occurring in the human genome and comprise about 5% of the genome.

The viral retrotransposons also include the HERVs (human endogenous retroviruses). They are classified into subfamilies in accordance with a characteristic amino acid position (e.g., HERV-K, HERV-W). They comprise an estimated 8% of the human genome. They originate in retroviral infections of the germ line, which have occurred repeatedly in the course of the evolution of man. However, most of these genetic elements have become transcriptionally inactive by mutations and deletions. Only a few have a full-length organization with the viral genes gag, pol and env. In this case, these are flanked by LTR (long terminal repeat) sequences, which include regulatory sequence modules. Potentially active HERVs are silenced by DNA methylation lest they should interfere with the integrity of the gene expression of a healthy cell. In contrast, an increased HERV transcription and also protein biosynthesis is found in different tumor entities.

Presently, the term "methylation level" is intended to mean the demethylation or methylation of a DNA. A DNA in question can be either methylated or non- or demethylated at at least one site thereof. Since this condition is a binary one and thus the demethylation and methylation at a particular position are directly related to one another, the methylation level can be determined either by the demethylation and/or by the methylation at this at least one site. Thus, the normalized DNA methylation level as well as the relative methylation level can be determined via the methylation and/or demethylation of the DNA.

Presently, the terms "primer" and "oligonucleotide" are used interchangeably. A primer is considered specific for a particular sequence if ≥75%, ≥80%, ≥85%, ≥90%, preferably ≥95%, ≥97%, more preferably ≥99%, or ≥99.5% sequence identity with the sequence in question of its complement. In a particularly preferred embodiment, the primer has 100% sequence identity with the sequence in question or its complement. In another preferred embodiment, the primer is considered specific for a particular sequence if it will hybridize with it (or its complement) under high salt conditions.

In the following, the term "high salt conditions" is supposed to mean a medium using a high salt buffer, preferably a high salt buffer containing chaotropic salts. High salt, preferably having chaotropic salts, reduces the solubility of nucleic acids in water. The reason for this is the rupture of hydrogen bonds and hence a reduction of the stabilization of secondary and tertiary structures of the nucleic acids in water. Now, if a polar surface is offered as a hydrogen bond donor, the nucleic acids will bind to this surface, because they experience a better stabilization there than they would experience in water. If the salt concentration is reduced, water again becomes a better hydrogen bond donor than the polar surface, and the nucleic acids can be detached from the surface again.

In particular, but not in a limited way, the term "high salt buffer" is understood to mean a buffer having a high salt concentration (preferably chaotropic substances), preferably ≥100 mM, more preferably ≥500 mM, and even more preferably ≥1 M.

In particular, but not in a limited way, the term "chaotropic substances" or "chaotropic salts" is understood to mean substances that alter the secondary, tertiary and/or quaternary structure of proteins and/or nucleic acids and leave at least the primary structure intact, reduce the solubility of polar substances in water, and/or enhance hydrophobic interactions. Preferred chaotropic substances include guanidine hydrochloride, guanidinium(iso)thiocyanate, sodium iodide, sodium perchlorate, potassium iodide, sodium(iso)thiocyanate and/or urea.

The term "amplification" or "amplification reaction" is intended to mean a process which enables the concentration of a nucleic acid sequence in question to be at least doubled.

A distinction is made between isothermic and thermocyclic amplification reactions. In the former, the temperature always remains constant throughout the process, while in the latter, thermocycles are passed by means of which the reaction and the amplification are controlled.

Preferred isothermic amplification reactions include, for example:
loop mediated isothermal amplification (LAMP),
nucleic acid sequence based amplification (NASBA),
rolling circle chain reaction (RCCR), or rolling circle amplification (RCA), and/or
transcription mediated amplification (TMA).

Preferred thermocyclic amplification reactions include, for example:
ligase chain reaction (LCR), and/or
polymerase chain reaction (PCR).

The term "polymerase chain reaction" (PCR) is intended to mean a process for the in vitro amplification of nucleic acids as described, for example, in Bartlett & Stirling (2003).

The term "ligase chain reaction" (LCR) is intended to mean a detection process for minute amounts of nucleic acids that functions in a way similar to that of polymerase chain reaction, but using a different enzyme (a ligase rather than a polymerase). Two probes per DNA strand are ligated to one probe. The generated amplificates of a cycle, which are often only 30-50 bp long, serve themselves as a starting point for the supplemented primers in the following cycles.

The term "loop mediated isothermal amplification" (LAMP) is intended to mean a method for isothermal nucleic acid amplification, in which 6 different primers are employed, which recognize and bind to particular regions on the target sequence. LAMP makes use of a DNA polymerase having strand-displacement activity and proceeds at a constant temperature of about 65° C. The amplification and detection of the target sequence take place in a single step.

The term "nucleic acid sequence based amplification" (NASBA) is intended to mean a method for the amplification of RNA (Compton 1991). In this method, an RNA template is added to a reaction mixture, and a first primer binds to the complementary sequence in the region of the 3'-end of the template. Subsequently, the DNA strand complementary to the template is polymerized by means of a reverse transcriptase. Then, the RNA template is digested by means of RNase H (RNase H digests exclusively RNA in RNA-DNA hybrids, but not single-stranded RNA). Subsequently, a second primer is bound to the 5' end of the DNA strand. It is used by the T7 RNA polymerase as a starting point for the synthesis of an RNA molecule complementary to the DNA strand, which can then again be used as a starting template. NASBA is performed at a constant temperature of usually 41° C. and under certain circumstances yields faster and better results as compared to PCR.

The term "transcription mediated amplification" (TMA) is intended to mean an isothermal amplification method developed by the U.S. company Gen-Probe, which is similar to NASBA and in which RNA polymerase and reverse transcriptase are also used (Hill, 2001).

The term "rolling circle chain reaction" (RCCR) or "rolling circle amplification" (RCA) relates to an amplification method that mimics the general nucleic acid replication according to the rolling circle principle and is described, inter alia, in U.S. Pat. No. 5,854,033.

The term "real-time PCR", also referred to as quantitative PCR or qPCR (not to be confused with reverse transcription PCR), is intended to mean a method that is based on the principle of the known polymerase chain reaction (PCR) and additionally enables the quantification of the amplified DNA. The quantification is performed by means of fluorescence measurements performed during a PCR cycle (whence the name "real time"). The fluorescence increases proportionally with the amount of PCR products. At the end of a run (which consists of several cycles), the quantification is effected in the exponential phase of PCR by means of obtained fluorescence signals. Only in the exponential phase of PCR (which takes a few cycles within a run), a correct quantification is possible, since optimum reaction conditions are prevailing during this phase. Thus, this method is distinct from other quantitative PCR methods, which perform a first evaluation only after completion of the PCR (e.g., competitive PCR), mostly with inclusion of a gel-electrophoretic separation of the PCR fragments.

For detection, dyes such as ethidium bromide, SYBR Green I as well as FRET probes or so-called double-dye oligos (also referred to as TaqMan probes) may be used.

The term "Ct value" (threshold cycle) refers to the PCR cycle in which an amplificate can be detected for the first time; usually, the fluorescence is measured, and the cycle in which this fluorescence rises significantly above the background fluorescence for the first time is stated as the Ct.

In the initial phase of a PCR reaction, the amount of template (i.e., of DNA to be amplified) is still limited, while in the final phase of amplification, the amount of the products increases to such an extent that there is inhibition by these products, product fragments increasingly hybridize with each other, and the educts are slowly consumed. Only in the intermediate phase, there is an exponential relationship between the number of amplification cycles and amount of amplificate ("exponential phase"). For the determination of the time at which the exponential phase begins, use is made of the mentioned Ct value.

Moreover, a low Ct value means that a low number of PCR cycles is sufficient for a first-time significant increase of the fluorescence above the background noise (i.e., relatively much templates was present), while a high Ct value correspondingly means that many PCR cycles are required for this (i.e., relatively little template was present).

In a first aspect, the present invention relates to a process for determining the normalized DNA methylation level, comprising the steps: a) quantitative determination of the presence of a transposon or fragment thereof in a DNA; b) quantitative determination of the presence of at least one differentially methylated C of a CpG dinucleotide within the same transposon or fragment thereof; and c) determination of the normalized DNA methylation level via the values determined in steps a) and b).

Thus, according to the invention, the presence of a transposon in a particular DNA (e.g., isolated from a bioptate) is quantitatively determined in a first step. This step yields a value providing information about the density/frequency (with respect to the DNA employed) or number of the transposon in the DNA examined, i.e., for example, the number of copies of the transposon present in the examined DNA. In a preferred embodiment, this determination is performed with a previously bisulfited DNA.

Then, in a second step, the presence of at least one differentially methylated cytosine of a CpG dinucleotide within the transposon detected in the first step is quantitatively determined. In a preferred embodiment, the same DNA as in the first step is used here. For example, the DNA isolated from a sample can be divided into two portions, preferably wherein each portion contains the same amount of DNA. In another preferred embodiment, this determination in the second step is performed on a bisulfited DNA (this step is treated in more detail below). Thus, the value obtained provides information about the presence of methylated or non-methylated cytosines at many different, randomly distributed positions in the genome. Thus, this second step provides information about the number/amount of differentially methylated cytosines within the transposon determined in the first step. Accordingly, the degree of differential methylation of the cytosines in the examined transposons is determined.

Since the transposons are randomly distributed over the genome, a normalization can be performed in a next step by means of the two values obtained, in which the values determined in the first and second steps are placed in relation to one another. Due to the high number of transposons in the genome, a large sample size is obtained. Thus, the obtained value of the normalized DNA methylation reflects a value of the differential methylation that can be considered as normalized to the respective genome in question.

In further embodiments, the order of the first and second steps can be reversed, or performed simultaneously, for example, by means of real time PCR.

Presently, "quantitative determination" is intended to mean a detection of the presence of a transposon or of the presence of a differential methylation. The detection is not to be merely qualitative, i.e., answer the question of whether a transposon or a differential methylation is present in the DNA being examined, but such presence is also to be quantified (for example, by stating the quantity, number of copies and the like).

The skilled person knows different methods for performing such a quantitative determination. In a preferred embodiment, such quantitative determination is effected by an amplification with subsequent measurement of the amount of amplificate produced. In a more preferred embodiment, the amplification is a PCR. In a further, even more preferred embodiment, the quantitative determination is effected by means of real time PCR to determine the Ct value. In a further embodiment, the quantitative determination is effected via the hybridization of a marked probe (e.g., nucleic acid probe), followed by determining the height of the peak produced (directly or indirectly) by the marker. In a further embodiment, an in situ hybridization (e.g., FISH) is performed, followed by determining the height of the peak produced by the marker. Other methods for such quantitative determinations include detection with 5-methylcytosine-specific antibodies, or the indirect detection of factors binding to methylated DNA using specific antibodies. Such factors include, for example, the nuclear repressor MeCP2, which binds to symmetrically methylated CpG positions of the genome, and MBD1, MBD2, MBD4.

In further embodiments, the DNA originates from organisms, tissue, cells, bioptate, or a sample. Preferably, the DNA is isolated DNA. In one embodiment, the isolated DNA is genomic and/or eukaryotic DNA. Preferably, this DNA is the DNA of a vertebrate, more preferably of a human. In a further preferred embodiment, the providing of the DNA does not include the sampling itself, but is based on sample material already obtained. In a further preferred embodiment, the tissues, cells, bioptates or samples from which the DNA originates are from a healthy subject or a diseased subject or patient.

In further embodiments, the sample is selected from the group consisting of a blood sample, a tissue sample, a saliva sample, a urine sample, a smear and a stool sample. In a preferred embodiment, the sample is a urine sample. This is advantageous, in particular, for the detection of a bladder and/or prostate cancer.

In further embodiments of the invention, the transposon is selected from the group consisting of a LINE element, an Alu element (Alu consensus sequence; Kariya et al. Gene. 1987; 53(1):1-10), a HERV element or a fragment thereof. In a particular embodiment, the transposon is a LINE-1 element (GenBank Accession M80343) or a fragment thereof. More preferably, the fragment of the transposon is the promoter region of a transposon. This has the advantage that a high frequency of CpG is present and thus, it is easier to determine the methylation level. In the most preferred embodiment, the fragment of the transposon is the promoter region of a LINE-1 element.

Presently, "differential methylation" is intended to mean the methylation state of a given DNA existing in the different possible forms. Reference to a "differential methylation of a cytosine" (C) means the methylation state of the cytosine in question. In a binary alternative, it may be either methylated, i.e., the cytosine is in the form of $^{5m}C$, or it may be non-methylated (or demethylated), i.e., the cytosine in question has no 5' methyl group.

A preferred method for determining the presence of a differential methylation (or the presence of a differential methylation of a cytosine) is based on the bisulfitation of DNA followed by analyzing the bisulfited DNA produced.

In order to get from isolated DNA to bisulfite-converted DNA, the isolated DNA is converted by a bisulfiting reaction well known to the skilled person. In this reaction, the non-methylated cytosines of the DNA are converted to uracil by the bilsulfite. As a result of this conversion, different variants of a converted nucleic acid depending on the number of non-methylated cytosines of such nucleic acid may exist. For example, a nucleic acid that contains 2 cytosines can result in 4 different variants after bisulfitation depending on the methylation state of these cytosines, because either none, the first, the second or both cytosines can be non-methylated and converted to uracil. In a preferred embodiment, these different variants can be detected by means of specific primers or sets of primers. In one embodiment, the conversion may be followed by another step of purification of the bisulfited DNA. In a further embodiment, the bisulfitation of the DNA is included an another step in the process of the invention, preferably as a first step, or before the quantitative determination of the presence of a differentially methylated cytosine of a CpG dinucleotide.

In a further, particularly preferred embodiment, step a) comprises the amplification of the non-bisulfited DNA with at least one primer pair that is specific for a transposon or fragment thereof, or alternatively the amplification of the bisulfited DNA with at least one primer pair that is specific for a bisulfited transposon or fragment thereof, wherein the primers do not include a differentially methylated position of the transposon, i.e., do not include a C or converted U/T of a CpG dinucleotide; further, step b) comprises the amplification of the bisulfited DNA with at least one primer pair that is specific for the transposon or fragment thereof (that was determined in step a)), and that includes at least one primer comprising at least one differentially methylated position of the transposon, i.e., is able to discriminate between at least one C of a methylated CpG and at least one U/T of a bisulfited non-methylated CpG; further, step c) comprises the determination of the normalized DNA methylation level via the ratio of the amplificates formed in steps a) and b).

In other words, the DNA may be either non-bisulfited (i.e., direct after the isolation from a sample, for example) or already bisulfited for the determination in step a). In the first case, any primers specific for the transposon can be used for its amplification; in the latter case, care should be taken that the primers employed do not include a differentially methylated site (i.e., no cytosine of a CpG dinucleotide). In a preferred embodiment, the same volume of DNA is employed in steps a) and b), wherein the DNA has preferably been isolated in one operation from one sample. More preferably, the same amounts of DNA are employed in steps a) and b). In this case too, the DNA has preferably been isolated in one operation from one sample.

In step b), which is always performed with bisulfited DNA, the situation is reversed; at least one primer should include a differentially methylated site of the transposon amplified in step a) (i.e., at least one cytosine of a CpG dinucleotide). It does not matter whether the at least one differentially methylated site for which said at least one primer is specific is on the sense or antisense strand. Thus, using this primer, an existing or non-existing methylation of the starting DNA can be detected at the examined position in question. If an amplificate is obtained with primers specific for a CpG, then there was a methylation of the original DNA at the site in question, since no conversion has taken place in the bisulfitation reaction. If an amplificate is obtained with primers specific for a bisulfited CpG, then there was no methylation (a demethylation) of the original DNA at the site in question. Accordingly, depending on the kind of primers employed, a methylation or demethylation can be detected.

For the determination of the methylation level according to the invention, either the methylation or the demethylation of the DNA of the transposon may be determined, since these two conditions are directly corresponding. Thus, if a CpG-specific primer pair is used, the DNA methylation level is determined using the methylation; if a primer pair specific for a bisulfited CpG is used, the DNA methylation level is determined using the demethylation.

In a preferred embodiment, at least one primer of the at least one primer pair is specific for at least one differentially methylated position of the transposon; more preferably, both primers of the at least one primer pair are specific for at least one differentially methylated position of the transposon. This has the advantage that a better specificity and an improved amplification are achieved.

In further preferred embodiments, the primers employed are specific for more than one differentially methylated position. Such primers are specific for more than one cytosine of a CpG or bisulfited CpG. In particularly preferred embodiments, the primers are specific for 2, 3, 4 or more than 4 differentially methylated position.

Further, since the primers are specific for a transposon, they are specific, in a preferred embodiment, for a LINE element, Alu element, HERV element, HERV-K element or a fragment thereof. In a particularly preferred embodiment, the primers are specific for a LINE-1 element or a fragment thereof. More preferably, the primers are specific for the promoter region of a transposon. This has the advantage that a high frequency of CpG is present, and thus it is easier to determine the methylation level. In the most preferred embodiment, the primers are specific for the promoter region of a LINE-1 element.

In another embodiment, the primers employed have a length of at least 15 nucleotides, preferably 18, 19, 20, 21, 22, 23, 24, 25 or more than 25 nucleotides. A primer pair may include primers having different lengths. In a preferred embodiment, the primers have a length of from 18 to 35 nucleotides, and in a further preferred embodiment, the primers have a length of from 20 to 30 nucleotides.

In a preferred embodiment, the primers of a primer pair are specific either exclusively for at least one cytosine of a CpG dinucleotide or exclusively for at least one cytosine of a bisulfited CpG dinucleotide.

The primers can include said at least one nucleotide specific for a differentially methylated position at any position, i.e., at the 5' end of the primer oligonucleotide, at the 3' end or at any position between. In a particularly preferred embodiment, said at least one nucleotide specific for a differentially methylated position is at the 3' end of the primer nucleotide. This has the advantage of an increased specificity.

In a further particularly preferred embodiment, the primer pairs used in step a) and step b) are in direct vicinity on the amplified region of the transposon. The term "direct vicinity" is intended to mean that there is a distance of ≤6000 bp, ≤5000 bp, ≤4000 bp, ≤3000 bp, ≤2000 bp, ≤1000 bp, ≤800 bp, ≤600 bp, ≤500 bp, more preferably ≤400 bp or ≤300 bp, and even more preferably ≤200 bp or ≤100 bp between the regions of the transposon amplified in step a) and in step b). In even more preferred embodiments, this distance is ≤80 bp, ≤50 bp or ≤10 bp. In further, even more preferred embodiments, the distance is 0 bp, or the amplified regions overlap.

Due to their expert knowledge, the skilled person is capable of producing a wide variety of primers according to the invention, which are specific for at least one differentially methylated position of a transposon. This shall be described in the following by means of the promoter region of the LINE-1 element.

The nucleic acid sequence (SEQ ID No. 1416) of this promoter region of the LINE-1 element (GenBank Accession M80343) is:

ggggggaggagccaagatggcCGaataggaacagctcCGgtctacagct cccagCGtgagCGaCGcagaagaCGgtgatttctgcatttccatctgag gtacCGggttcatctcactagggagtgccagacagtgggCGcaggccag tgtgtgtgCGcacCGtgCGCGagcCGaagcagggCGaggcattgcctca cctgggaagCGcaagggtcagggagttccctttctgagtcaaagaaag gggtgaCGgtCGcacctggaaaatCGggtcactcccaccCGaatattgC GcttttcagacCGgcttaagaaaCGgCGcaccaCGagactatatccac acctggctCGgagggtcctaCGcccaCGgaatctCGctgattgctagca cagcagtctgagatcaaactgcaaggCG wherein CpG have been highlighted by capital letters.

Thus, in the case of a complete methylation of this promoter sequence with subsequent bisulfitation, the following nucleic acid sequence (SEQ ID No. 1) would result:

ggggggaggagTTaagatggTCGaaTaggaaTagTtTCGgtTtaTagTt

TTTagCGtgagCGaCGTagaagaCGgtgatttTtgTatttTTatTtgag gtaTCGggttTatTtTaTtagggagtgTTagaTagtgggCGTaggTTag tgtgtgtgCGTaTCGtgCGCGagTCGaagTagggCGaggTattgTTtTa TTtgggaagCGTaaggggtTagggagttTTTtttTtgagtTaaagaaag gggtgaCGgtCGTaTTtggaaaatCGggtTaTtTTTaTTCGaatattgC GTttttTagaTCGgTtttaagaaaCGgCGTaTTaCGagaTtatatTTTaT aTTtggTtCGgagggtTTtaCGTTTaCGgaatTtCGTtgattgTtagTa TagTagtTtgagatTaaaTtgTaaggCG wherein the methylated CpG and the nucleotides converted from C to U (or T) by the bisulfitation are represented in capital letters.

In the case of a complete demethylation of this promoter sequence with subsequent bisulfitation, the following nucleic acid sequence (SEQ ID No. 2) would result:

ggggggaggagTTaagaTggTTGaaTaggaaTagTTTTGgTTTaTagTT

TTTagTGTgagTGaTGTagaagaTGgTgaTTTTTgTaTTTTTaTTTgag gTaTTGggTTTaTTTTaTTagggagTgTTagaTagTgggTGTaggTTag TgTgTgTgTGTaTTGTgTGTGagTTGaagTagggTGaggTaTTgTTTTa TTTgggaagTGTaaggggTTagggagTTTTTTTTTTgagTTaaagaaag gggTgaTGgTTGTaTTTggaaaaTTGggTTaTTTTTaTTTGaaTaTTgT GTTTTTTagaTTGgTTTaagaaaTGgTGTaTTaTGagaTTaTaTTTTaT aTTTggTTTGgagggTTTTaTGTTTaTGgaaTTTTGTTgaTTgTTagTa TagTagTTTgagaTTaaaTTgTaaggTG wherein the demethylated (and converted) CpG and the nucleotides converted from C to U (or T) by the bisulfitation are represented in capital letters.

Thus, on the basis of SEQ ID No. 1 and SEQ ID No. 2, primers can be selected for discrimination between DNAs differentially methylated at at least one site. Of course, the skilled person is familiar with the fact that there is also an antisense strand corresponding to the shown sense strand. On the antisense strand, 5'-CpG-3' dinucleotides that correspond to the 5'-CpG-3' dinucleotides are present, which are also differentially methylated. Thus, primers may also be selected on the basis of the sequence information of the antisense strand.

Since the sense and antisense strands are no longer complementary after the bisulfitation reaction, four different specific primers can be generated at first when there is one differentially methylated position: 1) identical sequence and specific for the converted sense strand, 2) complementary and specific for the converted sense strand, 3) identical sequence and specific for the converted antisense strand, 4) complementary and specific for the converted antisense strand. Since the differentially methylated position can be in two states, there are thus eight possible primers.

As an example, we may proceed from the double-stranded DNA sequence:

```
5'-AGCACGT-3' (sense)
3'-TCGTGCA-5' (antisense)
```

After the bisulfitation reaction, this respectively yields the no longer complementary strands, depending on the methylation state:

```
Methylated:   5'-AGUACGT-3' and 3'-TUGTGCA-5';
Demethylated: 5'-AGUAUGT-3' and 3'-TUGTGUA-5'.
```

Now, for each of these 4 sequences, a primer having an identical sequence and a primer that is complementary to the sequence can be generated, namely:

```
Methylated:
5'-AGUACGT-3'  and  5'-ACGTACT-3',
5'-ACGTGUT-3'  and  5'-AACACGT-3', Demethylated:
5'-AGUAUGT-3'  and  5'-ACATACT-3',
5'-AUGTGUT-3'  and  5'-AACACAT-3'.
```

Examples and even more preferred embodiments of such primers that are specific for one or more (bisulfited) cytosines of CpG dinucleotides and thus for at least one differentially methylated position of a transposon are given in SEQ ID Nos. 3 to 1048 or in Tables 1 to 12. Of these, Tables 1 to 4 state particularly preferred primers for the LINE-1 element, Tables 5 to 8 state particularly preferred primers for the Alu element, and Tables 9 to 12 state particularly preferred primers for the HERV-K element. The primers are stated in 5' to 3' orientation.

In preferred embodiments, the invention relates to the following of these oligonucleotides and the use thereof in the processes according to the invention:

Identical sequence or complementary primer sequences that are specific for the bilsulfite-converted methylated or demethylated sense or antisense strand of the promoter region of the LINE-1 element, i.e., SEQ ID Nos. 3 to 436; more preferably SEQ ID Nos. 3 to 112, or SEQ ID Nos. 113 to 220, or SEQ ID Nos. 221 to 336, or SEQ ID Nos. 337 to 436; even more preferably SEQ ID Nos. 3 to 57, or SEQ ID Nos. 58 to 112, or SEQ ID Nos. 113 to 166, or SEQ ID Nos. 167 to 220, or SEQ ID Nos. 221 to 278, or SEQ ID Nos. 279 to 336, or SEQ ID Nos. 337 to 386, or SEQ ID Nos. 387 to 436.

Identical sequence or complementary primer sequences that are specific for the bilsulfite-converted methylated or demethylated sense or antisense strand of the promoter region of the Alu element, i.e., SEQ ID Nos. 437 to 612; more preferably SEQ ID Nos. 437 to 476, or SEQ ID Nos. 477 to 522, or SEQ ID Nos. 523 to 570, or SEQ ID Nos. 571 to 612; even more preferably SEQ ID Nos. 437 to 456, or SEQ ID Nos. 457 to 476, or SEQ ID Nos. 477 to 499, or SEQ ID Nos. 500 to 522, or SEQ ID Nos. 523 to 546, or SEQ ID Nos. 547 to 570, or SEQ ID Nos. 571 to 591, or SEQ ID Nos. 592 to 612.

Identical sequence or complementary primer sequences that are specific for the bilsulfite-converted methylated or demethylated sense or antisense strand of the promoter region of the HERV-K element, i.e., SEQ ID Nos. 613 to 1048; more preferably SEQ ID Nos. 613 to 708, or SEQ ID Nos. 709 to 796, or SEQ ID Nos. 797 to 922, or SEQ ID Nos. 923 to 1048; even more preferably SEQ ID Nos. 613 to 660, or SEQ ID Nos. 661 to 708, or SEQ ID Nos. 709 to 752, or SEQ ID Nos. 753 to 796, or SEQ ID Nos. 797 to 859, or SEQ ID Nos. 860 to 922, or SEQ ID Nos. 923 to 985, or SEQ ID Nos. 986 to 1048.

TABLE 1

Preferred identical sequence primer sequences specific for the bisulfite-converted methylated or demethylated sense strand of the promoter region of the LINE-1 element.

| Methylated | SEQ ID No. | Demethylated | SEQ ID No. |
| --- | --- | --- | --- |
| GGGGAGGAGTTAAGATGGTC | 3 | GGGGAGGAGTTAAGATGGTT | 58 |
| GGTCGAATAGGAATAGTTTC | 4 | GGTTGAATAGGAATAGTTTT | 59 |
| TTCGGTTTATAGTTTTTAGC | 5 | TTTGGTTTATAGTTTTTAGT | 60 |
| TTATAGTTTTTAGCGTGAGC | 6 | TTATAGTTTTTAGTGTGAGT | 61 |
| TAGTTTTTAGCGTGAGCGAC | 7 | TAGTTTTTAGTGTGAGTGAT | 62 |
| GCGTGAGCGACGTAGAAGAC | 8 | GTGTGAGTGATGTAGAAGAT | 63 |
| GTATTTTTATTTGAGGTATC | 9 | GTATTTTTATTTGAGGTATT | 64 |
| GGGAGTGTTAGATAGTGGGC | 10 | GGGAGTGTTAGATAGTGGGT | 65 |
| GCGTAGGTTAGTGTGTGTGC | 11 | GTGTAGGTTAGTGTGTGTGT | 66 |
| GGTTAGTGTGTGTGCGTATC | 12 | GGTTAGTGTGTGTGTGTATT | 67 |
| AGTGTGTGTGCGTATCGTGC | 13 | AGTGTGTGTGTGTATTGTGT | 68 |
| TGTGTGTGCGTATCGTGCGC | 14 | TGTGTGTGTGTATTGTGTGT | 69 |
| GTGCGTATCGTGCGCGAGTC | 15 | GTGTGTATTGTGTGTGAGTT | 70 |
| TGCGCGAGTCGAAGTAGGGC | 16 | TGTGTGAGTTGAAGTAGGGT | 71 |
| TATTGTTTTATTTGGGAAGC | 17 | TATTGTTTTATTTGGGAAGT | 72 |
| GAGTTAAAGAAAGGGGTGAC | 18 | GAGTTAAAGAAAGGGGTGAT | 73 |
| TAAAGAAAGGGGTGACGGTC | 19 | TAAAGAAAGGGGTGATGGTT | 74 |
| ACGGTCGTATTTGGAAAATC | 20 | ATGGTTGTATTTGGAAAATT | 75 |

TABLE 1-continued

Preferred identical sequence primer sequences specific for the bisulfite-converted methylated or demethylated sense strand of the promoter region of the LINE-1 element.

| Methylated | SEQ ID No. | Demethylated | SEQ ID No. |
|---|---|---|---|
| AAATCGGGTTATTTTTATTC | 21 | AAATTGGGTTATTTTTATTT | 76 |
| TATTTTTATTCGAATATTGC | 22 | TATTTTTATTTGAATATTGT | 77 |
| AATATTGCGTTTTTAGATC | 23 | AATATTGTGTTTTTAGATT | 78 |
| TTTAGATCGGTTTAAGAAAC | 24 | TTTAGATTGGTTTAAGAAAT | 79 |
| AGATCGGTTTAAGAAACGGC | 25 | AGATTGGTTTAAGAAATGGT | 80 |
| TTTAAGAAACGGCGTATTAC | 26 | TTTAAGAAATGGTGTATTAT | 81 |
| TTATATTTTATATTTGGTTC | 27 | TTATATTTTATATTTGGTTT | 82 |
| TTTGGTTCGGAGGGTTTTAC | 28 | TTTGGTTTGGAGGGTTTTAT | 83 |
| TCGGAGGGTTTTACGTTTAC | 29 | TTGGAGGGTTTTATGTTTAT | 84 |
| TTTTACGTTTACGGAATTTC | 30 | TTTTATGTTTATGGAATTTT | 85 |
| TTGAGATTAAATTGTAAGGC | 31 | TTGAGATTAAATTGTAAGGT | 86 |
| TTAAATTGTAAGGCGGTAAC | 32 | TTAAATTGTAAGGTGGTAAT | 87 |
| AACGAGGTTGGGGAGGGGC | 33 | AATGAGGTTGGGGAGGGGT | 88 |
| AGGTTGGGGAGGGGCGTTC | 34 | AGGTTGGGGAGGGGTGTTT | 89 |
| TTTAGGTAAATAAAGTAGTC | 35 | TTTAGGTAAATAAAGTAGTT | 90 |
| ATAAAGTAGTCGGGAAGTTC | 36 | ATAAAGTAGTTGGGAAGTTT | 91 |
| AGTAGTGGTTTTTTAGTAC | 37 | AGTAGTGGTTTTTTAGTAT | 92 |
| GTAGTTGGAGATTTGAGAAC | 38 | GTAGTTGGAGATTTGAGAAT | 93 |
| GTTTTTGATTTTGATTTTC | 39 | GTTTTTGATTTTGATTTTT | 94 |
| GGTATATTGATATTTTATAC | 40 | GGTATATTGATATTTTATAT | 95 |
| TTAGAAAGGATATTTATATC | 41 | TTAGAAAGGATATTTATATT | 96 |
| AAAATTGGAAATTTTAAAAC | 42 | AAAATTGGAAATTTTAAAAT | 97 |
| GAAATTTTAAAACGTAGAGC | 43 | GAAATTTTAAAATGTAGAGT | 98 |
| TTTTTTTTTTTAAAGGAAC | 44 | TTTTTTTTTTTAAAGGAAT | 99 |
| GGATGGAGAATGATTTTGAC | 45 | GGATGGAGAATGATTTTGAT | 100 |
| GAGAGAAGAAGGTTTTAGAC | 46 | GAGAGAAGAAGGTTTTAGAT | 101 |
| ATTAAATTATTTTGAGTTAC | 47 | ATTAAATTATTTTGAGTTAT | 102 |
| GGAGTTGAAAATTAAGGTTC | 48 | GGAGTTGAAAATTAAGGTTT | 103 |
| AATTAAGGTTCGAGAATTAC | 49 | AATTAAGGTTTGAGAATTAT | 104 |
| ATGTAGAAGTTTTAGGAGTC | 50 | ATGTAGAAGTTTTAGGAGTT | 105 |
| GAAGTTTTAGGAGTCGATGC | 51 | GAAGTTTTAGGAGTTGATGT | 106 |
| TGAAATGAATGAAATGAAGC | 52 | TGAAATGAATGAAATGAAGT | 107 |
| TGTGAAAAGATTAAATTTAC | 53 | TGTGAAAAGATTAAATTTAT | 108 |
| ATTTAGTAAGGTAGGTTAAC | 54 | ATTTAGTAAGGTAGGTTAAT | 109 |
| ATTTAGGAAATATAGAGAAC | 55 | ATTTAGGAAATATAGAGAAT | 110 |

TABLE 1-continued

Preferred identical sequence primer sequences specific for the bisulfite-converted methylated or demethylated sense strand of the promoter region of the LINE-1 element.

| Methylated | SEQ ID No. | Demethylated | SEQ ID No. |
|---|---|---|---|
| GTTATAAAGATATTTTTC | 56 | GTTATAAAGATATTTTTT | 111 |
| GGTAGTTAGAGAGAAAGGTC | 57 | GGTAGTTAGAGAGAAAGGTT | 112 |

TABLE 2

Preferred complementary primer sequences specific for the bisulfite-converted methylated or demethylated sense strand of the promoter region of the LINE-1 element.

| Methylated | SEQ ID No. | Demethylated | SEQ ID No. |
|---|---|---|---|
| TTTCCTTTAAAAATAACCCG | 113 | TTTCCTTTAAAAATAACCCA | 167 |
| TCTTAAAATTACTCTTCTCG | 114 | TCTTAAAATTACTCTTCTCA | 168 |
| CGAAAAATATCTTTATAACG | 115 | CAAAAAATATCTTTATAACA | 169 |
| ATATTTCCTAAATCTAAACG | 116 | ATATTTCCTAAATCTAAACA | 170 |
| TCAAATACACCAATCAAACG | 117 | TCAAATACACCAATCAAACA | 171 |
| TCTCTAAACTTCCCTTCTCG | 118 | TCTCTAAACTTCCCTTCTCA | 172 |
| CCCTTTCTTCCAATTAATCG | 119 | CCCTTTCTTCCAATTAATCA | 173 |
| TCTTCCAATTAATCGCATCG | 120 | TCTTCCAATTAATCACATCA | 174 |
| AAACTTCTACATTCTTCACG | 121 | AAACTTCTACATTCTTCACA | 175 |
| CATTCTTCACGTAATTCTCG | 122 | CATTCTTCACATAATTCTCA | 176 |
| TTAATTTAAATATCCTCCCG | 123 | TTAATTTAAATATCCTCCCA | 177 |
| AACTCAAAATAATTTAATCG | 124 | AACTCAAAATAATTTAATCA | 178 |
| AACCTTCTTCTCTCAACTCG | 125 | AACCTTCTTCTCTCAACTCA | 179 |
| ATTACTAATAAAAAACTACG | 126 | ATTACTAATAAAAAACTACA | 180 |
| CCTTTAAAAAAAAAAAACG | 127 | CCTTTAAAAAAAAAAAACA | 181 |
| AAAAAAAAAAACGCTCTACG | 128 | AAAAAAAAAAACACTCTACA | 182 |
| AATATACAAATAAATTTTCG | 129 | AATATACAAATAAATTTTCA | 183 |
| TCTATTAAAATACCCTACCG | 130 | TCTATTAAAATACCCTACCA | 184 |
| CCTCCCAATTAAACTACTCG | 131 | CCTCCCAATTAAACTACTCA | 185 |
| AAAAACAATCTATCTACCCG | 132 | AAAAACAATCTATCTACCCA | 186 |
| TTCTCAAATCTCCAACTACG | 133 | TTCTCAAATCTCCAACTACA | 187 |
| AATAAACTCCACCCAATTCG | 134 | AATAAACTCCACCCAATTCA | 188 |
| CACCCAATTCGAACTTCCCG | 135 | CACCCAATTCAAACTTCCCA | 189 |
| AACCTAAACAATAACGAACG | 136 | AACCTAAACAATAACAAACA | 190 |
| ACGCCCCTCCCCCAACCTCG | 137 | ACACCCCTCCCCCAACCTCA | 191 |
| CTCCCCCAACCTCGTTACCG | 138 | CTCCCCCAACCTCATTACCA | 192 |
| TACTATACTAACAATCAACG | 139 | TACTATACTAACAATCAACA | 193 |
| TAACAATCAACGAAATTCCG | 140 | TAACAATCAACAAAATTCCA | 194 |

TABLE 2-continued

Preferred complementary primer sequences specific for the bisulfite-converted methylated or demethylated sense strand of the promoter region of the LINE-1 element.

| Methylated | SEQ ID No. | Demethylated | SEQ ID No. |
|---|---|---|---|
| TCAACGAAATTCCGTAAACG | 141 | TCAACAAAATTCCATAAACA | 195 |
| CGTAAACGTAAAACCCTCCG | 142 | CATAAACATAAAACCCTCCA | 196 |
| AAATATAAAATATAATCTCG | 143 | AAATATAAAATATAATCTCA | 197 |
| AAATATAATCTCGTAATACG | 144 | AAATATAATCTCATAATACA | 198 |
| TATAATCTCGTAATACGCCG | 145 | TATAATCTCATAATACACCA | 199 |
| ATACGCCGTTTCTTAAACCG | 146 | ATACACCATTTCTTAAACCA | 200 |
| TTAAACCGATCTAAAAAACG | 147 | TTAAACCAATCTAAAAAACA | 201 |
| TCTAAAAACGCAATATTCG | 148 | TCTAAAAACACAATATTCA | 202 |
| ATTCGAATAAAAATAACCCG | 149 | ATTCAAATAAAAATAACCCA | 203 |
| AACCCGATTTTCCAAATACG | 150 | AACCCAATTTTCCAAATACA | 204 |
| CGATTTTCCAAATACGACCG | 151 | CAATTTTCCAAATACAACCA | 205 |
| AAACTCCCTAACCCCTTACG | 152 | AAACTCCCTAACCCCTTACA | 206 |
| CCAAATAAAACAATACCTCG | 153 | CCAAATAAAACAATACCTCA | 207 |
| CAATACCTCGCCCTACTTCG | 154 | CAATACCTCACCCTACTTCA | 208 |
| CCTCGCCCTACTTCGACTCG | 155 | CCTCACCCTACTTCAACTCA | 209 |
| TCGCCCTACTTCGACTCGCG | 156 | TCACCCTACTTCAACTCACA | 210 |
| CCTACTTCGACTCGCGCACG | 157 | CCTACTTCAACTCACACACA | 211 |
| TTCGACTCGCGCACGATACG | 158 | TTCAACTCACACACAATACA | 212 |
| CGCACACACACTAACCTACG | 159 | CACACACACACTAACCTACA | 213 |
| TCCCTAATAAAATAAACCCG | 160 | TCCCTAATAAAATAAACCCA | 214 |
| TAAAAATACAAAAATCACCG | 161 | TAAAAATACAAAAATCACCA | 215 |
| AAAAATCACCGTCTTCTACG | 162 | AAAAATCACCATCTTCTACA | 216 |
| AATCACCGTCTTCTACGTCG | 163 | AATCACCATCTTCTACATCA | 217 |
| CGTCTTCTACGTCGCTCACG | 164 | CATCTTCTACATCACTCACA | 218 |
| ACGCTAAAAACTATAAACCG | 165 | ACACTAAAAACTATAAACCA | 219 |
| ACCGAAACTATTCCTATTCG | 166 | ACCAAAACTATTCCTATTCA | 220 |

TABLE 3

Preferred identical sequence primer sequences specific for the bisulfite-converted methylated or demethylated antisense strand of the promoter region of the LINE-1 element.

| Methylated | SEQ ID No. | Demethylated | SEQ ID No. |
|---|---|---|---|
| TGTAGTTTTTTTTAGTTTC | 221 | TGTAGTTTTTTTTAGTTTT | 279 |
| TTTTGGTATGATTTTGTAGC | 222 | TTTTGGTATGATTTTGTAGT | 280 |
| ATTTTGTAGCGGTTGGTATC | 223 | ATTTTGTAGTGGTTGGTATT | 281 |
| TGGTTTGTAGGGTTTTTGTC | 224 | TGGTTTGTAGGGTTTTTGTT | 282 |
| TTTTTTTTTGAGGGTAATTC | 225 | TTTTTTTTTGAGGGTAATTT | 283 |

TABLE 3-continued

Preferred identical sequence primer sequences specific for the bisulfite-converted methylated or demethylated antisense strand of the promoter region of the LINE-1 element.

| Methylated | SEQ ID No. | Demethylated | SEQ ID No. |
|---|---|---|---|
| GTTTTGGAGTTGTTTTTTTC | 226 | GTTTTGGAGTTGTTTTTTTT | 284 |
| TGTATTTTTGAATTTGAAC | 227 | TGTATTTTTGAATTTGAAT | 285 |
| TTTAGGTATATTAATTAGAC | 228 | TTTAGGTATATTAATTAGAT | 286 |
| TTTTTTAAATTTTTTTTTTC | 229 | TTTTTTAAATTTTTTTTTTT | 287 |
| ATTTTTTTTTTAGTTGATC | 230 | ATTTTTTTTTTAGTTGATT | 288 |
| TTTTTTTAGTTGATCGTATC | 231 | TTTTTTTAGTTGATTGTATT | 289 |
| GAGGTTTTGTATTTTTTAC | 232 | GAGGTTTTGTATTTTTTAT | 290 |
| GTATTTTTACGTAGTTTTC | 233 | GTATTTTTATGTAGTTTTT | 291 |
| TTTGGTTTGAATGTTTTTTC | 234 | TTTGGTTTGAATGTTTTTTT | 292 |
| TAGTTTAGAGTAATTTGATC | 235 | TAGTTTAGAGTAATTTGATT | 293 |
| AAGTTTTTTTTTTAGTTC | 236 | AAGTTTTTTTTTTAGTTT | 294 |
| TGTTGTTGGTGAGGAATTGC | 237 | TGTTGTTGGTGAGGAATTGT | 295 |
| TTTTTTGGAGGAGGAGAGGC | 238 | TTTTTTGGAGGAGGAGAGGT | 296 |
| GAGGAGGAGAGGCGTTTTGC | 239 | GAGGAGGAGAGGTGTTTTGT | 297 |
| TGATGTATAGATGGGTTTTC | 240 | TGATGTATAGATGGGTTTTT | 298 |
| GTTTGTTGGAATATTTTGTC | 241 | GTTTGTTGGAATATTTTGTT | 299 |
| GTTTTTTAGTTAGGTTGTTC | 242 | GTTTTTTAGTTAGGTTGTTT | 300 |
| AGGAGGTAGTTTGTTTGTTC | 243 | AGGAGGTAGTTTGTTTGTTT | 301 |
| GTTTTTAGATTTTTAGTTGC | 244 | GTTTTTAGATTTTTAGTTGT | 302 |
| TGGTGGGTTTTATTTAGTTC | 245 | TGGTGGGTTTTATTTAGTTT | 303 |
| TTATTTAGTTCGAGTTTTTC | 246 | TTATTTAGTTTGAGTTTTTT | 304 |
| AAGTAAGTTTGGGTAATGGC | 247 | AAGTAAGTTTGGGTAATGGT | 305 |
| AAGTTTGGGTAATGGCGGGC | 248 | AAGTTTGGGTAATGGTGGGT | 306 |
| GGCGTTTTTTTTTAGTTTC | 249 | GGTGTTTTTTTTTAGTTTT | 307 |
| TTTTTTTTAGTTTCGTTGTC | 250 | TTTTTTTTAGTTTTGTTGTT | 308 |
| TTGTTGTGTTAGTAATTAGC | 251 | TTGTTGTGTTAGTAATTAGT | 309 |
| TTAGTAATTAGCGAGATTTC | 252 | TTAGTAATTAGTGAGATTTT | 310 |
| ATTAGCGAGATTTCGTGGGC | 253 | ATTAGTGAGATTTTGTGGGT | 311 |
| TCGTGGGCGTAGGATTTTTC | 254 | TTGTGGGTGTAGGATTTTTT | 312 |
| TAGGTGTGGGATATAGTTTC | 255 | TAGGTGTGGGATATAGTTTT | 313 |
| GGGATATAGTTTCGTGGTGC | 256 | GGGATATAGTTTTGTGGTGT | 314 |
| ATATAGTTTCGTGGTGCGTC | 257 | ATATAGTTTTGTGGTGTGTT | 315 |
| GGTGCGTCGTTTTTTAAGTC | 258 | GGTGTGTTGTTTTTTAAGTT | 316 |
| TTTAAGTCGGTTTGAAAAGC | 259 | TTTAAGTTGGTTTGAAAAGT | 317 |
| GTTTGAAAAGCGTAATATTC | 260 | GTTTGAAAAGTGTAATATTT | 318 |
| TATTCGGGTGGGAGTGATTC | 261 | TATTTGGGTGGGAGTGATTT | 319 |

TABLE 3-continued

Preferred identical primer sequences specific for the bisulfite-converted methylated or demethylated antisense strand of the promoter region of the LINE-1 element.

| Methylated | SEQ ID No. | Demethylated | SEQ ID No. |
|---|---|---|---|
| TGATTCGATTTTTTAGGTGC | 262 | TGATTTGATTTTTTAGGTGT | 320 |
| TCGATTTTTTAGGTGCGATC | 263 | TTGATTTTTTAGGTGTGATT | 321 |
| GGAATTTTTTGATTTTTTGC | 264 | GGAATTTTTTGATTTTTTGT | 322 |
| TTTAGGTGAGGTAATGTTTC | 265 | TTTAGGTGAGGTAATGTTTT | 323 |
| GTAATGTTTCGTTTTGTTTC | 266 | GTAATGTTTTGTTTTGTTTT | 324 |
| GTTTCGTTTTGTTTCGGTTC | 267 | GTTTTGTTTTGTTTTGGTTT | 325 |
| TTCGTTTTGTTTCGGTTCGC | 268 | TTTGTTTTGTTTTGGTTTGT | 326 |
| TTTTGTTTCGGTTCGCGTAC | 269 | TTTTGTTTTGGTTTGTGTAT | 327 |
| TTTCGGTTCGCGTACGGTGC | 270 | TTTTGGTTTGTGTATGGTGT | 328 |
| GCGTATATATATTGGTTTGC | 271 | GTGTATATATATTGGTTTGT | 329 |
| TTTTTTAGTGAGATGAATTC | 272 | TTTTTTAGTGAGATGAATTT | 330 |
| ATGGAAATGTAGAAATTATC | 273 | ATGGAAATGTAGAAATTATT | 331 |
| TAGAAATTATCGTTTTTTGC | 274 | TAGAAATTATTGTTTTTTGT | 332 |
| AAATTATCGTTTTTTGCGTC | 275 | AAATTATTGTTTTTTGTGTT | 333 |
| TCGTTTTTTGCGTCGTTTAC | 276 | TTGTTTTTTGTGTTGTTTAT | 334 |
| TACGTTGGGAGTTGTAGATC | 277 | TATGTTGGGAGTTGTAGATT | 335 |
| GATCGGAGTTGTTTTTATTC | 278 | GATTGGAGTTGTTTTTATTT | 336 |

TABLE 4

Preferred complementary primer sequences specific for the bisulfite-converted methylated or demethylated antisense strand of the promoter region of the LINE-1 element.

| Methylated | SEQ ID No. | Demethylated | SEQ ID No. |
|---|---|---|---|
| AAAAAAAAACCAAAATAACCG | 337 | AAAAAAAAACCAAAATAACCA | 387 |
| AACCGAATAAAAACAACTCCG | 338 | AACCAAATAAAAACAACTCCA | 388 |
| TCCGATCTACAACTCCCAACG | 339 | TCCAATCTACAACTCCCAACA | 389 |
| CTACAACTCCCAACGTAAACG | 340 | CTACAACTCCCAACATAAACA | 390 |
| CAACTCCCAACGTAAACGACG | 341 | CAACTCCCAACATAAACAACA | 391 |
| ACGTAAACGACGCAAAAAACG | 342 | ACATAAACAACACAAAAAACA | 392 |
| ACATTTCCATCTAAAATACCG | 343 | ACATTTCCATCTAAAATACCA | 393 |
| AAAAATACCAAACAATAAACG | 344 | AAAAATACCAAACAATAAACA | 394 |
| ACGCAAACCAATATATATACG | 345 | ACACAAACCAATATATATACA | 395 |
| AACCAATATATATACGCACCG | 346 | AACCAATATATATACACACCA | 396 |
| AATATATATACGCACCGTACG | 347 | AATATATATACACACCATACA | 397 |
| TATATATACGCACCGTACGCG | 348 | TATATATACACACCATACACA | 398 |
| ATACGCACCGTACGCGAACCG | 349 | ATACACACCATACACAAACCA | 399 |
| TACGCGAACCGAAACAAAACG | 350 | TACACAAACCAAAACAAAACA | 400 |

TABLE 4-continued

Preferred complementary primer sequences specific for the bisulfite-converted methylated or demethylated antisense strand of the promoter region of the LINE-1 element.

| Methylated | SEQ ID No. | Demethylated | SEQ ID No. |
|---|---|---|---|
| CATTACCTCACCTAAAAAACG | 351 | CATTACCTCACCTAAAAAACA | 401 |
| AAATCAAAAAAAAAATAACG | 352 | AAATCAAAAAAAAAATAACA | 402 |
| CAAAAAAAAAATAACGATCG | 353 | CAAAAAAAAAATAACAATCA | 403 |
| ACGATCGCACCTAAAAAATCG | 354 | ACAATCACACCTAAAAAATCA | 404 |
| AAATCGAATCACTCCCACCCG | 355 | AAATCAAATCACTCCCACCCA | 405 |
| CACTCCCACCCGAATATTACG | 356 | CACTCCCACCCAAATATTACA | 406 |
| AATATTACGCTTTTCAAACCG | 357 | AATATTACACTTTTCAAACCA | 407 |
| TTCAAACCGACTTAAAAAACG | 358 | TTCAAACCAACTTAAAAAACA | 408 |
| AAACCGACTTAAAAAACGACG | 359 | AAACCAACTTAAAAAACAACA | 409 |
| CTTAAAAAACGACGCACCACG | 360 | CTTAAAAAACAACACACCACA | 410 |
| CTATATCCCACACCTAACTCG | 361 | CTATATCCCACACCTAACTCA | 411 |
| CCTAACTCGAAAAATCCTACG | 362 | CCTAACTCAAAAAATCCTACA | 412 |
| TCGAAAATCCTACGCCCACG | 363 | TCAAAAATCCTACACCCACA | 413 |
| TCCTACGCCCACGAAATCTCG | 364 | TCCTACACCCACAAAATCTCA | 414 |
| CTAAAATCAAACTACAAAACG | 365 | CTAAAATCAAACTACAAAACA | 415 |
| TCAAACTACAAAACGACAACG | 366 | TCAAACTACAAAACAACAACA | 416 |
| AACGAAACTAAAAAAAAACG | 367 | AACAAAACTAAAAAAAAACA | 417 |
| AAACTAAAAAAAAACGCCCG | 368 | AAACTAAAAAAAAACACCCA | 418 |
| CTTAAATAAACAAAACAACCG | 369 | CTTAAATAAACAAAACAACCA | 419 |
| ACAAACAACCGAAAAACTCG | 370 | ACAAACAACCAAAAAACTCA | 420 |
| AACAATAATTCTCCCAACACG | 371 | AACAATAATTCTCCCAACACA | 421 |
| GCAACTAAAAATCTAAAAACG | 372 | GCAACTAAAAATCTAAAAACA | 422 |
| ATCCCTAACTCCTAACCCCCG | 373 | ATCCCTAACTCCTAACCCCCA | 423 |
| AACACACTAACACCTCACACG | 374 | AACACACTAACACCTCACACA | 424 |
| CCAAAAAAAACATCTACACCG | 375 | CCAAAAAAAACATCTACACCA | 425 |
| AAAACTAAAAACTCTAAAACG | 376 | AAAACTAAAAACTCTAAAACA | 426 |
| AAAACTCTAAAACGCAAAACG | 377 | AAAACTCTAAAACACAAAACA | 427 |
| CTCTCCTCCTCCAAAAAAACG | 378 | CTCTCCTCCTCCAAAAAAACA | 428 |
| AAATAAAAATAATTTTAACG | 379 | AAATAAAAATAATTTTAACA | 429 |
| AAAAAAAAAAACTTCAAACG | 380 | AAAAAAAAAAACTTCAAACA | 430 |
| ATCAAATTACTCTAAACTACG | 381 | ATCAAATTACTCTAAACTACA | 431 |
| AAAACTAAAAACCAAAACTCG | 382 | AAAACTAAAAACCAAAACTCA | 432 |
| AACCAAAACTCGAAAACTACG | 383 | AACCAAAACTCAAAAACTACA | 433 |
| ATACAAAAACCTCAAAAACCG | 384 | ATACAAAAACCTCAAAAACCA | 434 |
| AAAACCTCAAAAACCGATACG | 385 | AAAACCTCAAAAACCAATACA | 435 |
| TAAAATAAATAAAATAAAACG | 386 | TAAAATAAATAAAATAAAACA | 436 |

TABLE 5

Preferred identical sequence primer sequences specific for the bisulfite-converted methylated or demethylated sense strand of the Alu element.

| Methylated | SEQ ID No. | Demethylated | SEQ ID No. |
|---|---|---|---|
| GGTCGGGCGCGGTGGTTTAC | 437 | GGTTGGGTGTGGTGGTTTAT | 457 |
| TTTTAGTATTTTGGGAGGTC | 438 | TTTTAGTATTTTGGGAGGTT | 458 |
| GTATTTTGGGAGGTCGAGGC | 439 | GTATTTTGGGAGGTTGAGGT | 459 |
| TTTGGGAGGTCGAGGCGGGC | 440 | TTTGGGAGGTTGAGGTGGGT | 460 |
| TTATTTGAGGTTAGGAGATC | 441 | TTATTTGAGGTTAGGAGATT | 461 |
| GGTTAATATGGTGAAATTTC | 442 | GGTTAATATGGTGAAATTTT | 462 |
| TAAAAATATAAAAATTAGTC | 443 | TAAAAATATAAAAATTAGTT | 463 |
| AATATAAAAATTAGTCGGGC | 444 | AATATAAAAATTAGTTGGGT | 464 |
| AATTAGTCGGGCGTGGTGGC | 445 | AATTAGTTGGGTGTGGTGGT | 465 |
| TTAGTCGGGCGTGGTGGCGC | 446 | TTAGTTGGGTGTGGTGGTGT | 466 |
| AGTCGGGCGTGGTGGCGCGC | 447 | AGTTGGGTGTGGTGGTGTGT | 467 |
| GTTTGTAATTTTAGTTATTC | 448 | GTTTGTAATTTTAGTTATTT | 468 |
| GAGGTTGAGGTAGGAGAATC | 449 | GAGGTTGAGGTAGGAGAATT | 469 |
| TAGGAGAATCGTTTGAATTC | 450 | TAGGAGAATTGTTTGAATTT | 470 |
| ATCGTTTGAATTCGGGAGGC | 451 | ATTGTTTGAATTTGGGAGGT | 471 |
| GGTTGTAGTGAGTCGAGATC | 452 | GGTTGTAGTGAGTTGAGATT | 472 |
| TTGTAGTGAGTCGAGATCGC | 453 | TTGTAGTGAGTTGAGATTGT | 473 |
| TATTGTATTTTAGTTTGGGC | 454 | TATTGTATTTTAGTTTGGGT | 474 |
| TTTAGTTTGGGCGATAGAGC | 455 | TTTAGTTTGGGTGATAGAGT | 475 |
| GGGCGATAGAGCGAGATTTC | 456 | GGGTGATAGAGTGAGATTTT | 476 |

TABLE 6

Preferred complementary primer sequences specific for the bisulfite-converted methylated or demethylated sense strand of the Alu element.

| Methylated | SEQ ID No. | Demethylated | SEQ ID No. |
|---|---|---|---|
| TTTTTTAAAACGAAATCTCG | 477 | TTTTTTAAAACAAAATCTCA | 500 |
| AACGAAATCTCGCTCTATCG | 478 | AACAAAATCTCACTCTATCA | 501 |
| CAAACTAAAATACAATAACG | 479 | CAAACTAAAATACAATAACA | 502 |
| AACTAAAATACAATAACGCG | 480 | AACTAAAATACAATAACACA | 503 |
| AATACAATAACGCGATCTCG | 481 | AATACAATAACACAATCTCA | 504 |
| TCGACTCACTACAACCTCCG | 482 | TCAACTCACTACAACCTCCA | 505 |
| ACTACAACCTCCGCCTCCCG | 483 | ACTACAACCTCCACCTCCCA | 506 |
| CCGCCTCCCGAATTCAAACG | 484 | CCACCTCCCAAATTCAAACA | 507 |
| TCTCCTACCTCAACCTCCCG | 485 | TCTCCTACCTCAACCTCCCA | 508 |
| AATAACTAAAATTACAAACG | 486 | AATAACTAAAATTACAAACA | 509 |
| TAACTAAAATTACAAACGCG | 487 | TAACTAAAATTACAAACACA | 510 |

TABLE 6-continued

Preferred complementary primer sequences specific for the bisulfite-converted methylated or demethylated sense strand of the Alu element.

| Methylated | SEQ ID No. | Demethylated | SEQ ID No. |
|---|---|---|---|
| ACTAAAATTACAAACGCGCG | 488 | ACTAAAATTACAAACACACA | 511 |
| TACAAACGCGCGCCACCACG | 489 | TACAAACACACACCACCACA | 512 |
| AACGCGCGCCACCACGCCCG | 490 | AACACACACCACCACACCCA | 513 |
| TTATATTTTAATAAAAACG | 491 | TTATATTTTAATAAAAACA | 514 |
| TATTAACCAAAATAATCTCG | 492 | TATTAACCAAAATAATCTCA | 515 |
| TCCTAACCTCAAATAATCCG | 493 | TCCTAACCTCAAATAATCCA | 516 |
| AACCTCAAATAATCCGCCCG | 494 | AACCTCAAATAATCCACCCA | 517 |
| CAAATAATCCGCCCGCCTCG | 495 | CAAATAATCCACCCACCTCA | 518 |
| AAATACTAAAATTACAAACG | 496 | AAATACTAAAATTACAAACA | 519 |
| ATTACAAACGTAAACCACCG | 497 | ATTACAAACATAAACCACCA | 520 |
| TACAAACGTAAACCACCGCG | 498 | TACAAACATAAACCACCACA | 521 |
| AACGTAAACCACCGCGCCCG | 499 | AACGTAAACCACCGCGCCCA | 522 |

TABLE 7

Preferred identical sequence primer sequences specific for the bisulfite-converted methylated or demethylated antisense strand of the Alu element.

| Methylated | SEQ ID No. | Demethylated | SEQ ID No. |
|---|---|---|---|
| TTTTTTTGAGACGGAGTTTC | 523 | TTTTTTTGAGACTGAGTTTT | 547 |
| AGACGGAGTTTCGTTTTGTC | 524 | AGACTGAGTTTCTTTTTGTT | 548 |
| AGACGGAGTTTCGTTTTGTC | 525 | AGACTGAGTTTCTTTTTGTT | 549 |
| TTAGGTTGGAGTGTAGTGGC | 526 | TTAGGTTGGAGTGTAGTGGT | 550 |
| AGGTTGGAGTGTAGTGGCGC | 527 | AGGTTGGAGTGTAGTGGCTT | 551 |
| GAGTGTAGTGGCGCGATTTC | 528 | GAGTGTAGTGGCTCTATTTT | 552 |
| TTCGGTTTATTGTAATTTTC | 529 | TTCTGTTTATTGTAATTTTT | 553 |
| TATTGTAATTTTCGTTTTTC | 530 | TATTGTAATTTTCTTTTTTT | 554 |
| TTCGTTTTTCGGGTTTAAGC | 531 | TTCTTTTTTCTGGTTTAAGT | 555 |
| TTTTTTTGTTTTAGTTTTTC | 532 | TTTTTTTGTTTTAGTTTTTT | 556 |
| GAGTAGTTGGGATTATAGGC | 533 | GAGTAGTTGGGATTATAGGT | 557 |
| GTAGTTGGGATTATAGGCGC | 534 | GTAGTTGGGATTATAGGCTT | 558 |
| AGTTGGGATTATAGGCGCGC | 535 | AGTTGGGATTATAGGCTCTT | 559 |
| TTATAGGCGCGCGTTATTAC | 536 | TTATAGGCTCTCTTTATTAT | 560 |
| AGGCGCGCGTTATTACGTTC | 537 | AGGCTCTCTTTATTACTTTT | 561 |
| TTTGTATTTTAGTAGAGAC | 538 | TTTGTATTTTAGTAGAGAT | 562 |
| ATGTTGGTTAGGATGGTTTC | 539 | ATGTTGGTTAGGATGGTTTT | 563 |
| TTTTTGATTTTAGGTGATTC | 540 | TTTTTGATTTTAGGTGATTT | 564 |
| TGATTTTAGGTGATTCGTTC | 541 | TGATTTTAGGTGATTCTTTT | 565 |
| TTAGGTGATTCGTTCGTTTC | 542 | TTAGGTGATTCTTTCTTTTT | 566 |
| AAAGTGTTGGGATTATAGGC | 543 | AAAGTGTTGGGATTATAGGT | 567 |
| GATTATAGGCGTGAGTTATC | 544 | GATTATAGGCTTGAGTTATT | 568 |
| TTATAGGCGTGAGTTATCGC | 545 | TTATAGGCTTGAGTTATCTT | 569 |
| AGGCGTGAGTTATCGCGTTC | 546 | AGGCTTGAGTTATCTCTTTT | 570 |

TABLE 8

Preferred complementary primer sequences specific for the bisulfite-converted methylated or demethylated antisense strand of the Alu element.

| Methylated | SEQ ID No. | Demethylated | SEQ ID No. |
|---|---|---|---|
| ACCGAACGCGATAACTCACG | 571 | ACCAAACACAATAACTCACA | 592 |
| CCCAACACTTTAAAAAACCG | 572 | CCCAACACTTTAAAAAACCA | 593 |
| CACTTTAAAAAACCGAAACG | 573 | CACTTTAAAAAACCAAAACA | 594 |
| TTAAAAAACCGAAACGAACG | 574 | TTAAAAAACCAAAACAAACA | 595 |

TABLE 8-continued

Preferred complementary primer sequences specific for the bisulfite-converted methylated or demethylated antisense strand of the Alu element.

| Methylated | SEQ ID No. | Demethylated | SEQ ID No. |
|---|---|---|---|
| CACCTAAAATCAAAAAATCG | 575 | CACCTAAAATCAAAAAATCA | 596 |
| ACCAACATAATAAAACCCCG | 576 | ACCAACATAATAAAACCCCA | 597 |
| AAAAATACAAAAATTAACCG | 577 | AAAAATACAAAAATTAACCA | 598 |
| ATACAAAAATTAACCGAACG | 578 | ATACAAAAATTAACCAAACA | 599 |
| ATTAACCGAACGTAATAACG | 579 | ATTAACCAAACATAATAACA | 600 |
| TAACCGAACGTAATAACGCG | 580 | TAACCAAACATAATAACACA | 601 |
| ACCGAACGTAATAACGCGCG | 581 | ACCAAACATAATAACACACA | 602 |
| CCTATAATCCCAACTACTCG | 582 | CCTATAATCCCAACTACTCA | 603 |
| GAACTAAAACAAAAAAATCG | 583 | GAACTAAAACAAAAAAATCA | 604 |
| AAAAAAATCGCTTAAACCCG | 584 | AAAAAAATCACTTAAACCCA | 605 |
| TCGCTTAAACCCGAAAAACG | 585 | TCACTTAAACCCAAAAAACA | 606 |
| ACGAAAATTACAATAAACCG | 586 | ACAAAAATTACAATAAACCA | 607 |
| ATTACAATAAACCGAAATCG | 587 | ATTACAATAAACCAAAATCA | 608 |
| TACAATAAACCGAAATCGCG | 588 | TACAATAAACCAAAATCACA | 609 |
| ACTACACTCCAACCTAAACG | 589 | ACTACACTCCAACCTAAACA | 610 |
| CCAACCTAAACGACAAAACG | 590 | CCAACCTAAACAACAAAACA | 611 |
| AACGACAAAACGAAACTCCG | 591 | AACAACAAAACAAAACTCCA | 612 |

TABLE 9

Preferred identical sequence primer sequences specific for the bisulfite-converted methylated or demethylated sense strand of the HERV-K element.

| Methylated | SEQ ID No. | Demethylated | SEQ ID No. |
|---|---|---|---|
| ATGATTTTATTTTTAATTTC | 613 | ATGATTTATTTTTAATTTT | 661 |
| GGGTTAAATGGATTAAGGGC | 614 | GGGTTAAATGGATTAAGGGT | 662 |
| TTTAGGGATATAAAAATTGC | 615 | TTTAGGGATATAAAAATTGT | 663 |
| AGAGTTTGAAATATGGTTTC | 616 | AGAGTTTGAAATATGGTTTT | 664 |
| GGGAAGGGAAAGATTTGATC | 617 | GGGAAGGGAAAGATTTGATT | 665 |
| ATTTGATCGTTTTTTAGTTC | 618 | ATTTGATCTTTTTTTAGTTT | 666 |
| TTTGGGTAATGGAATGTTTC | 619 | TTTGGGTAATGGAATGTTTT | 667 |
| AATGTTTCGGTATAAAATTC | 620 | AATGTTTCTGTATAAATTT | 668 |
| GGTATAAAATTCGATTGTAC | 621 | GGTATAAAATTCTATTGTAT | 669 |
| ATGTAAAGATTTTGTTTAC | 622 | ATGTAAAGATTTTGTTTAT | 670 |
| TTTTTTAGAGAAATATTTAC | 623 | TTTTTTAGAGAAATATTTAT | 671 |
| GGATTTTTTATATGTTGAAC | 624 | GGATTTTTTATATGTTGAAT | 672 |
| ATGTTGAACGTTGGTTTTTC | 625 | ATGTTGAACTTTGGTTTTTT | 673 |
| AGTTTTTTATTGTATTTTAC | 626 | AGTTTTTTATTGTATTTTAT | 674 |
| TTTTTTATTTGGTGTTTAAC | 627 | TTTTTTATTTGGTGTTTAAT | 675 |
| TTTGGGGTGAAGGTATATTC | 628 | TTTGGGGTGAAGGTATATTT | 676 |
| GGGTGAAGGTATATTCGAGC | 629 | GGGTGAAGGTATATTCTAGT | 677 |
| GTGGTTATTGAGGATAAGTC | 630 | GTGGTTATTGAGGATAAGTT | 678 |
| ATAAGTCGATAAGAGATTTC | 631 | ATAAGTCTATAAGAGATTTT | 679 |
| ATATTTATAGTTAGTTTTAC | 632 | ATATTTATAGTTAGTTTTAT | 680 |
| TACGGTAAGTTTGTGTATTC | 633 | TACTGTAAGTTTGTGTATTT | 681 |
| TATTTTAAATAGAAGATAGC | 634 | TATTTTAAATAGAAGATAGT | 682 |
| AAAAAATTTTAGAAGGAAAC | 635 | AAAAAATTTTAGAAGGAAAT | 683 |
| AAACGGAAATTTTATATTGC | 636 | AAACTGAAATTTTATATTGT | 684 |
| TGCGAATATGTAGTAGAGTC | 637 | TGCTAATATGTAGTAGAGTT | 685 |
| TCGTTAATGGTTTAGTTAAC | 638 | TCTTTAATGGTTTAGTTAAT | 686 |
| GTTATTAGAGTTTAAATTAC | 639 | GTTATTAGAGTTTAAATTAT | 687 |
| TTTTAGTAGGTTAGGTGATC | 640 | TTTTAGTAGGTTAGGTGATT | 688 |
| GTAATATTATAATTTTAAGC | 641 | GTAATATTATAATTTTAAGT | 689 |
| GTTATTAATATTGGTTATC | 642 | GTTATTAATATTGGTTATT | 690 |
| ATTAATATTGGTTATCGGTC | 643 | ATTAATATTGGTTATCTGTT | 691 |
| ATCGGTCGAATTTTAGTATC | 644 | ATCTGTCTAATTTTAGTATT | 692 |
| AGGGAGTTATATTTTTAGTC | 645 | AGGGAGTTATATTTTTAGTT | 693 |
| AAGGAAGGAGATATTGAGGC | 646 | AAGGAAGGAGATATTGAGGT | 694 |
| GCGTGGTAATTTTTAGTAAC | 647 | GCTTGGTAATTTTTAGTAAT | 695 |
| TTTTTAGTAACGTTAGAATC | 648 | TTTTTAGTAACTTTAGAATT | 696 |
| ATGTGGATTTTGTGTTTAC | 649 | ATGTGGATTTTGTGTTTAT | 697 |
| GATTTTGTGTTTACGGATC | 650 | GATTTTGTGTTTACTGATT | 698 |
| TTTGTGTTTACGGATCGATC | 651 | TTTGTGTTTACTGATCTATT | 699 |
| GATCGATCGTGGGAGGTTTC | 652 | GATCTATCTTGGGAGGTTTT | 700 |
| TGATTGAAATATTAAAAGGC | 653 | TGATTGAAATATTAAAAGGT | 701 |
| TTATAAATTTTATATTAATC | 654 | TTATAAATTTTATATTAATT | 702 |
| TAGGTGTATTTAATAGTTTC | 655 | TAGGTGTATTTAATAGTTTT | 703 |
| TTCGAAGAGATAGTGATATC | 656 | TTCTAAGAGATAGTGATATT | 704 |
| GAGATAGTGATATCGAGAAC | 657 | GAGATAGTGATATCTAGAAT | 705 |
| CGAGAACGGGTTATGATGAC | 658 | CTAGAACTGGTTATGATGAT | 706 |

TABLE 9-continued

Preferred identical sequence primer sequences specific for the bisulfite-converted methylated or demethylated sense strand of the HERV-K element.

| Methylated | SEQ ID No. | Demethylated | SEQ ID No. |
|---|---|---|---|
| CGGGTTATGATGACGATGGC | 659 | CTGGTTATGATGACTATGGT | 707 |
| ATGACGATGGCGGTTTTGTC | 660 | ATGACTATGGCTGTTTTGTT | 708 |

TABLE 10

Preferred complementary primer sequences specific for the bisulfite-converted methylated or demethylated sense strand of the HERV-K element.

| Methylated | SEQ ID No. | Demethylated | SEQ ID No. |
|---|---|---|---|
| AAAAAAAATAAAAAAACCCG | 709 | AAAAAAAATAAAAAAACCCA | 753 |
| AAAAACCCGAAAAACCAACG | 710 | AAAAACCCAAAAAACCAACA | 754 |
| TCAACATATAAAAAATCCCG | 711 | TCAACATATAAAAAATCCCA | 755 |
| CATTCATAAATATTTCTCCG | 712 | CATTCATAAATATTTCTCCA | 756 |
| AAAATCAACAAACAAACACG | 713 | AAAATCAACAAACAAACACA | 757 |
| AAACATCTCAATACTTTACG | 714 | AAACATCTCAATACTTTACA | 758 |
| ATAAATAAAATATTCAATCG | 715 | ATAAATAAAATATTCAATCA | 759 |
| AAAATCCCTACGACCTTTCG | 716 | AAAATCCCTACAACCTTTCA | 760 |
| ATTTCCCCCTTTTCTTTTCG | 717 | ATTTCCCCCTTTTCTTTTCA | 761 |
| TTTTCTTTTCGACAAAACCG | 718 | TTTTCTTTTCAACAAAACCA | 762 |
| TTTCGACAAAACCGCCATCG | 719 | TTTCAACAAAACCACCATCA | 763 |
| GCCATCGTCATCATAACCCG | 720 | GCCATCATCATCATAACCCA | 764 |
| GTCATCATAACCCGTTCTCG | 721 | GTCATCATAACCCATTCTCA | 765 |
| TCGATATCACTATCTCTTCG | 722 | TCAATATCACTATCTCTTCA | 766 |
| AACAAAACAAACACACAACG | 723 | AACAAAACAAACACACAACA | 767 |
| TAACAAAATTAAAATTTACG | 724 | TAACAAAATTAAAATTTACA | 768 |
| TTTTAAATCTATTTAAAACG | 725 | TTTTAAATCTATTTAAAACA | 769 |
| CAAAATATAAATAAATAACG | 726 | CAAAATATAAATAAATAACA | 770 |
| AAATAACGAAACCTCCCACG | 727 | AAATAACAAAACCTCCCACA | 771 |
| AACGAAACCTCCCACGATCG | 728 | AACAAAACCTCCCACAATCA | 772 |
| AACCTCCCACGATCGATCCG | 729 | AACCTCCCACAATCAATCCA | 773 |
| GCAACTTTATAAAAAACCG | 730 | GCAACTTTATAAAAAACCA | 774 |
| TTAAAATAAAATTTAAATCG | 731 | TTAAAATAAAATTTAAATCA | 775 |
| ATAATATAAAATAACTTACG | 732 | ATAATATAAAATAACTTACA | 776 |
| CTAAACTTTCTATTAAATCG | 733 | CTAAACTTTCTATTAAATCA | 777 |
| TTTCTATTAAATCGCTATCG | 734 | TTTCTATTAAATCACTATCA | 778 |

TABLE 10-continued

Preferred complementary primer sequences specific for the bisulfite-converted methylated or demethylated sense strand of the HERV-K element.

| Methylated | SEQ ID No. | Demethylated | SEQ ID No. |
|---|---|---|---|
| AACGATCATAATAATTTCCG | 735 | AACAATCATAATAATTTCCA | 779 |
| CATTATTATAACAAATCTCG | 736 | CATTATTATAACAAATCTCA | 780 |
| CTTCTAAAACTATACCTACG | 737 | CTTCTAAAACTATACCTACA | 781 |
| CTAAAACTATACCTACGCCG | 738 | CTAAAACTATACCTACACCA | 782 |
| ACATTATCTCCTAATAAACG | 739 | ACATTATCTCCTAATAAACA | 783 |
| TAACTTTCTAAAAATAACCG | 740 | TAACTTTCTAAAAATAACCA | 784 |
| ATAACCGATACTAAAATTCG | 741 | ATAACCAATACTAAAATTCA | 785 |
| CCGATACTAAAATTCGACCG | 742 | CCAATACTAAAATTCAACCA | 786 |
| CTTATTTTCTCTAACCTACG | 743 | CTTATTTTCTCTAACCTACA | 787 |
| TTCGCAATATAAAATTTCCG | 744 | TTCACAATATAAAATTTCCA | 788 |
| TATCACCCTAACTTCTTCCG | 745 | TATCACCCTAACTTCTTCCA | 789 |
| CCGAATACACAAACTTACCG | 746 | CCAAATACACAAACTTACCA | 790 |
| ACTAACTATAAATATACTCG | 747 | ACTAACTATAAATATACTCA | 791 |
| ACTTATCCTCAATAACCACG | 748 | ACTTATCCTCAATAACCACA | 792 |
| ATCCTCAATAACCACGCTCG | 749 | ATCCTCAATAACCACACTCA | 793 |
| ACACCTATAAATATTTCTCG | 750 | ACACCTATAAATATTTCTCA | 794 |
| AAAAACCCGAAAAACCAACG | 751 | AAAAACCCAAAAAACCAACA | 795 |
| AAAATCAACAAACAAACACG | 752 | AAAATAAACAAACAAACACA | 796 |

TABLE 11

Preferred identical sequence primer sequences specific for the bisulfite-converted methylated or demethylated antisense strand of the HERV-K element.

| Methylated | SEQ ID No. | Demethylated | SEQ ID No. |
|---|---|---|---|
| AGAAAGAAATAAGGGGGTTC | 797 | AGAAAGAAATAAGGGGGTTT | 860 |
| AGGGGGTTCGGGGAATTAGC | 798 | AGGGGGTTCTGGGAATTAGT | 861 |
| TTTAGTATATGGAGGATTTC | 799 | TTTAGTATATGGAGGATTTT | 862 |
| TTAGTATTTATTGATTATTC | 800 | TTAGTATTTATTGATTATTT | 863 |
| TTATTCGTGGGTGTTTTTC | 801 | TTATTCTTGGGTGTTTTTT | 864 |
| GAGGGTTAGTAGATAAATAC | 802 | GAGGGTTAGTAGATAAATAT | 865 |
| TAAATATTTTAATGTTTTAC | 803 | TAAATATTTTAATGTTTTAT | 866 |
| AGTAGATGGAATGTTTAATC | 804 | AGTAGATGGAATGTTTAATT | 867 |
| TTTTAGTATAGATTTTTTAC | 805 | TTTTAGTATAGATTTTTTAT | 868 |
| ATAGATTTTTACGGGTGTC | 806 | ATAGATTTTTACTGGTGTT | 869 |
| TTAGGTTTTTTTTTTTTTAC | 807 | TTAGGTTTTTTTTTTTTTAT | 870 |

TABLE 11-continued

Preferred identical primer sequences specific for the bisulfite-converted methylated or demethylated antisense strand of the HERV-K element.

| Methylated | SEQ ID No. | Demethylated | SEQ ID No. |
|---|---|---|---|
| TTTTAGGTAGAGGTTTTTGC | 808 | TTTTAGGTAGAGGTTTTTGT | 871 |
| AGAGGTTTTTGCGGTTTTTC | 809 | AGAGGTTTTTGCTGTTTTTT | 872 |
| GTATATGTTTTAGAGAGTAC | 810 | GTATATGTTTTAGAGAGTAT | 873 |
| TATTTTTTTTTTTTTTTTC | 811 | TATTTTTTTTTTTTTTTTT | 874 |
| TTTTTTTTTTCGATAAAATC | 812 | TTTTTTTTTTCTATAAAATT | 875 |
| TTTTCGATAAAATCGTTATC | 813 | TTTTCTATAAAATCTTTATT | 876 |
| CGTTATCGTTATTATGGTTC | 814 | CTTTATCTTTATTATGGTTT | 877 |
| CGTTATTATGGTTCGTTTTC | 815 | CTTTATTATGGTTCTTTTTT | 878 |
| TTCGATGTTATTGTTTTTTC | 816 | TTCTATGTTATTGTTTTTTT | 879 |
| AGATAAAATAGGTATATAAC | 817 | AGATAAAATAGGTATATAAT | 880 |
| GTGATAGGGTTAAGATTTGC | 818 | GTGATAGGGTTAAGATTTGT | 881 |
| TAATTTTTGTTATAGTAGTC | 819 | TAATTTTTGTTATAGTAGTT | 882 |
| TTTTTGGATTTATTTAAAAC | 820 | TTTTTGGATTTATTTAAAAT | 883 |
| TTAAAATATGGATGGATGGC | 821 | TTAAAATATGGATGGATGGT | 884 |
| TGGATGGCGAGGTTTTTTAC | 822 | TGGATGGCTAGGTTTTTTAT | 885 |
| TGGCGAGGTTTTTTACGGTC | 823 | TGGCTAGGTTTTTTACTGTT | 886 |
| AGGTTTTTTACGGTCGGTTC | 824 | AGGTTTTTTACTGTCTGTTT | 887 |
| TGTTTTTATTAGTAGAATAC | 825 | TGTTTTTATTAGTAGAATAT | 888 |
| CGTAATTTTGTAAAGGAATC | 826 | CTTAATTTTGTAAAGGAATT | 889 |
| GTTAGAATGGAATTTAGGTC | 827 | GTTAGAATGGAATTTAGGTT | 890 |
| GATAGTATAAAATGGTTTAC | 828 | GATAGTATAAAATGGTTTAT | 891 |
| TTATTTGTGTATTTGGATAC | 829 | TTATTTGTGTATTTGGATAT | 892 |
| ATTGTGGTAGAATTGATTTC | 830 | ATTGTGGTAGAATTGATTTT | 893 |
| GTTTAATTTATAATAGTTTC | 831 | GTTTAATTTATAATAGTTTT | 894 |
| GTTTTGTAAATAATTTATTC | 832 | GTTTTGTAAATAATTTATTT | 895 |
| CGTGGTTTGAGTGATATTTC | 833 | CTTGGTTTGAGTGATATTTT | 896 |
| TTTAGGTTTGGTAGGGTAGC | 834 | TTTAGGTTTGGTAGGGTAGT | 897 |
| TGATTGGTGTTATTATTTTC | 835 | TGATTGGTGTTATTATTTTT | 898 |
| GTTATTATTTTCGTGGAGGC | 836 | GTTATTATTTTCTTGGAGGT | 899 |
| GTATTATATATGTAGAATTC | 837 | GTATTATATATGTAGAATTT | 900 |
| AGTATTTTTAAAGGTTTAC | 838 | AGTATTTTTAAAGGTTTAT | 901 |
| AGGAATGTTTAGAGTTGGTC | 839 | AGGAATGTTTAGAGTTGGTT | 902 |
| ATGGGGTTATATAATGTAGC | 840 | ATGGGGTTATATAATGTAGT | 903 |
| TTATTGTTGTAATAAATTTC | 841 | TTATTGTTGTAATAAATTTT | 904 |
| ATTTTTGAGGTTGTGTTTAC | 842 | ATTTTTGAGGTTGTGTTTAT | 905 |
| TTTGAGGTTGTGTTTACGTC | 843 | TTTGAGGTTGTGTTTACTTT | 906 |
| TTATAAGTATAGTTTTATGC | 844 | TTATAAGTATAGTTTTATGT | 907 |
| TTTTTTTTTTAGGTGGTATC | 845 | TTTTTTTTTTAGGTGGTATT | 908 |
| TAGGTGGTATCGGTTTTAAC | 846 | TAGGTGGTATCTGTTTTAAT | 909 |
| TTGATTTTTGGGGGTGGTC | 847 | TTGATTTTTGGGGGTGGTT | 910 |
| GGTGGTCGATATTGAAGTTC | 848 | GGTGGTCTATATTGAAGTTT | 911 |
| GTCGATATTGAAGTTCGGTC | 849 | GTCTATATTGAAGTTCTGTT | 912 |
| TTTTATTTTTTTTAATTTGC | 850 | TTTTATTTTTTTAATTTGT | 913 |
| GTTTGAGGTTGTAATGTTAC | 851 | GTTTGAGGTTGTAATGTTAT | 914 |
| GCGTTGATTGAGTTATTAAC | 852 | GCTTTGATTGAGTTATTAAT | 915 |
| TTGTTATTTTAGTTTTTTTC | 853 | TTGTTATTTTAGTTTTTTTT | 916 |
| TTCGAGTGTATAAGTTTATC | 854 | TTCTAGTGTATAAGTTTATT | 917 |
| GATTGTTTTTAATGATTAC | 855 | GATTGTTTTTAATGATTAT | 918 |
| TGTTTTTAATGATTACGTTC | 856 | TGTTTTTAATGATTACTTTT | 919 |
| TATATTTGTGGGTGTTTTTC | 857 | TATATTTGTGGGTGTTTTTT | 920 |
| AGAAAGAAATAAGGGGGTTC | 858 | AGAAAGAAATAAGGGGGTTT | 921 |
| AGGGGGTTCGGGGAATTAAC | 859 | AGGGGGTTCTGGGAATTAAT | 922 |

TABLE 12

Preferred complementary primer sequences specific for the bisulfite-converted methylated or demethylated antisense strand of the HERV-K element.

| Methylated | SEQ ID No. | Demethylated | SEQ ID No. |
|---|---|---|---|
| TAACCTTACCCCCAACCCCG | 923 | TAACCTTACCCCCAACCCCA | 986 |
| AATTAAATAAATTAAAAACG | 924 | AATTAAATAAATTAAAAACA | 987 |
| CCAAAAACACAAAAACTACG | 925 | CCAAAAACACAAAAACTACA | 988 |
| AAATCTAAAATATAACCTCG | 926 | AAATCTAAAATATAACCTCA | 989 |
| AAAAAAAAAAACCTAACCG | 927 | AAAAAAAAAAACCTAACCA | 990 |
| CCTAACCGTCCCCCAACCCG | 928 | CCTAACCATCCCCCAACCCA | 991 |
| CTAAACAATAAAATATCTCG | 929 | CTAAACAATAAAATATCTCA | 992 |
| ATATCTCGATATAAAACCCG | 930 | ATATCTCAATATAAAACCCA | 993 |
| ATATAAACCCGATTATACG | 931 | ATATAAACCCAATTATACA | 994 |
| TACAAAACCTTTATTCACG | 932 | TACAAAACCTTTATTCACA | 995 |
| CTCTCAAAAAACACCCACG | 933 | CTCTCAAAAAACACCCACA | 996 |
| AATCCTCCATATACTAAACG | 934 | AATCCTCCATATACTAAACA | 997 |

TABLE 12-continued

Preferred complementary primer sequences specific for the bisulfite-converted methylated or demethylated antisense strand of the HERV-K element.

| Methylated | SEQ ID No. | Demethylated | SEQ ID No. |
|---|---|---|---|
| TACTAAACGTTAATTCCCCG | 935 | TACTAAACATTAATTCCCCA | 998 |
| ATCTCTCATTACACCTTACG | 936 | ATCTCTCATTACACCTTACA | 999 |
| CCTTCATCTAATACCCAACG | 937 | CCTTCATCTAATACCCAACA | 1000 |
| CTAAAATAAAAATACACTCG | 938 | CTAAAATAAAAATACACTCA | 1001 |
| AATAAAAATACACTCGAACG | 939 | AATAAAAATACACTCAAACA | 1002 |
| TAATCATTAAAAACAAATCG | 940 | TAATCATTAAAAACAAATCA | 1003 |
| ATTTCAAACAAAAAATAACG | 941 | ATTTCAAACAAAAAATAACA | 1004 |
| AAAAATCCCAAAAAAAAACG | 942 | AAAAATCCCAAAAAAAAACA | 1005 |
| AACGAAAACTTTACATTACG | 943 | AACAAAAACTTTACATTACA | 1006 |
| ACGAATATATAACAAAACCG | 944 | ACAAATATATAACAAAACCA | 1007 |
| CGTTAATAACTCAATCAACG | 945 | CATTAATAACTCAATCAACA | 1008 |
| CCATTAAAATCTAAACCACG | 946 | CCATTAAAATCTAAACCACA | 1009 |
| TTCAACAAATCAAATAACCG | 947 | TTCAACAAATCAAATAACCA | 1010 |
| TAACATTACAACCTCAAACG | 948 | TAACATTACAACCTCAAACA | 1011 |
| CTTATCAATACTAACCACCG | 949 | CTTATCAATACTAACCACCA | 1012 |
| TCAATACTAACCACCGACCG | 950 | TCAATACTAACCACCAACCA | 1013 |
| CCGACCGAACTTCAATATCG | 951 | CCAACCAAACTTCAATATCA | 1014 |
| ATTACCAATAAAAAAACCCG | 952 | ATTACCAATAAAAAAACCCA | 1015 |
| AATAAAATTAATAACATACG | 953 | AATAAAATTAATAACATACA | 1016 |
| ATTAATAACATACGAAAACG | 954 | ATTAATAACATACAAAAACA | 1017 |
| TCAAAATATATAAAAACCCG | 955 | TCAAAATATATAAAAACCCA | 1018 |
| ATAAAATTAAAAAAACTACG | 956 | ATAAAATTAAAAAAACTACA | 1019 |
| AAAATAAACAACCATTATCG | 957 | AAAATAAACAACCATTATCA | 1020 |
| CTAATCTTAAAAAAATCACG | 958 | CTAATCTTAAAAAAATCACA | 1021 |
| AATTTAAAAACACTAATCCG | 959 | AATTTAAAAACACTAATCCA | 1022 |
| AACTATTACAAAACTTATCG | 960 | AACTATTACAAAACTTATCA | 1023 |
| TATTACAAAACTTATCGACG | 961 | TATTACAAAACTTATCAACA | 1024 |
| TATTACAACAATAAAATACG | 962 | TATTACAACAATAAAATACA | 1025 |
| AAAAATATTAATTAAATTCG | 963 | AAAAATATTAATTAAATTCA | 1026 |
| ATTAATCCGACAAAATTACG | 964 | ATTAATCCAACAAAATTACA | 1027 |
| TCAAAACTCCATATCAATCG | 965 | TCAAAACTCCATATCAATCA | 1028 |
| CAAAAAAAAAGCCTCCACG | 966 | CAAAAAAAAACACCTCCACA | 1029 |
| GAAATATCACTCAAACCACG | 967 | GAAATATCACTCAAACCACA | 1030 |
| ATTATAAATTAAACACCTCG | 968 | ATTATAAATTAAACACCTCA | 1031 |
| ACTCAAAACAAACTCAATCG | 969 | ACTCAAAACAAACTCAATCA | 1032 |
| ACAAATAAATCCAACTATCG | 970 | ACAAATAAATCCAACTATCA | 1033 |
| AAATCCAACTATCGATAACG | 971 | AAATCCAACTATCAATAACA | 1034 |
| ACTTTAAAAACAAAATATCG | 972 | ACTTTAAAAACAAAATATCA | 1035 |
| TAAACCATTTTATACTATCG | 973 | TAAACCATTTTATACTATCA | 1036 |
| ACCTAAATTCCATTCTAACG | 974 | ACCTAAATTCCATTCTAACA | 1037 |
| TATAAATCCCTATATCCACG | 975 | TATAAATCCCTATATCCACA | 1038 |
| ATCCCTATATCCACGAACCG | 976 | ATCCCTATATCCACAAACCA | 1039 |
| CTATATCCACGAACCGACCG | 977 | CTATATCCACAAACCAACCA | 1040 |
| ACCGACCGTAAAAAACCTCG | 978 | ACCAACCATAAAAAACCTCA | 1041 |
| CACTAAAACATAATTAAACG | 979 | CACTAAAACATAATTAAACA | 1042 |
| AAAAATTACTAATAACCTCG | 980 | AAAAATTACTAATAACCTCA | 1043 |
| CCGAAAAAACAATAACATCG | 981 | CCAAAAAAACAATAACATCA | 1044 |
| AAACAATAACATCGAAAACG | 982 | AAACAATAACATCAAAAACA | 1045 |
| GAAAACGAACCATAATAACG | 983 | GAAAACAAACCATAATAACA | 1046 |
| GAACCATAATAACGATAACG | 984 | GAACCATAATAACAATAACA | 1047 |
| TAACGATAACGATTTTATCG | 985 | TAACAATAACAATTTTATCA | 1048 |

The skilled person will acknowledge that each of the oligonucleotide sequences stated in Tables 1 to 12 is to be understood only as a core sequence, which may be truncated or extended from the 5' end and/or from the 3' end. This holds for all the oligonucleotides/primers disclosed in this invention. In a preferred embodiment, the oligonucleotides shown in Tables 1 to 12 are extended by from 1 to 20 nucleotides from the 5' end and/or from the 3' end; even more preferably, the oligonucleotides are extended by from 5 to 15 nucleotides from the 5' end and/or from the 3' end. In another embodiment, the oligonucleotides are truncated by up to a total of 5 nucleotides from the 5' end and/or from the 3' end, wherein the oligonucleotide always remains specific for at least one CpG or bisulfited CpG.

In another preferred embodiment, the primers of a primer pair have almost identical $T_m$s, preferably $T_m$s that deviate from one another by ≤3° C., ≤2° C., ≤1° C., ≤0.5° C., ≤0.2° C. or ≤0.1° C.

In another preferred embodiment, the sequence regions enclosed by the primers have a length of ≥1 and ≤3000 bp, more preferably ≥10 and ≤2000 bp, even more preferably ≥30 and ≤800 bp, and most preferably ≥50 and ≤300 bp.

The skilled person will acknowledge that not only one pair of primers, but also a plurality thereof may be employed. Therefore, in another embodiment, the process is performed with 2, 3, 4, 5 or more than 5 primer pairs that are specific for a transposon or fragment thereof and that respectively comprise at least one primer that is specific for at least one cytosine of a CpG dinucleotide or a bisulfited cytosine of a CpG dinucleotide. Preferably, these several primer pairs have almost identical $T_m$s.

Further, in step a), either the non-bisulfited DNA with at least one primer pair whose pair of primers are specific for regions of the same transposon or fragment thereof is amplified; or a bisulfited DNA with at least one primer pair that is also specific for the transposon, but wherein the primers do not include a differentially methylated position of the transposon, is amplified. In a preferred embodiment, primers are used which are specific for always non-methylated regions of the transposon. By a previous sequence analysis, the skilled person can determine which positions in a given genome are always non-methylated. Thus, since $^{5m}C$ exclusively occur in CpG dinucleotides in vertebrates, regions that contain no cytosines of such CpG sequences can be selected for such cases.

Tables 13 to 18 render preferred ones of such oligonucleotides for normalization, which may be used for step a) of the process, and when bisulfited DNA is employed. Tables 13 to 14 disclose preferred primers for the LINE-1 element, Tables 15 to 16 disclose preferred primers for the Alu element, and Tables 17 to 18 disclose preferred primers for the HERV-K element. The amplificates produced by this amplification step can then be employed for the normalization according to the invention.

In preferred embodiments, the invention relates to the following of such oligonucleotides for the normalization and the use thereof in the processes according to the invention:

Identical sequence or complementary primer sequences that are specific for the bilsulfite-converted sense or antisense strand of the promoter region of the LINE-1 element, i.e., SEQ ID Nos. 1049 to 1227; more preferably SEQ ID Nos. 1049 to 1145, or SEQ ID Nos. 1146 to 1227; even more preferably SEQ ID Nos. 1049 to 1096, or SEQ ID Nos. 1097 to 1145, or SEQ ID Nos. 1146 to 1192, or SEQ ID Nos. 1193 to 1227.

Identical sequence or complementary primer sequences that are specific for the bilsulfite-converted sense or antisense strand of the promoter region of the Alu element, i.e., SEQ ID Nos. 1228 to 1257; more preferably SEQ ID Nos. 1228 to 1243, or SEQ ID Nos. 1244 to 1257; even more preferably SEQ ID Nos. 1228 to 1237, or SEQ ID Nos. 1238 to 1243, or SEQ ID Nos. 1244 to 1250, or SEQ ID Nos. 1251 to 1257.

Identical sequence or complementary primer sequences that are specific for the bilsulfite-converted sense or antisense strand of the promoter region of the HERV-K element, i.e., SEQ ID Nos. 1258 to 1415; more preferably SEQ ID Nos. 125.8 to 1323, or SEQ ID Nos. 1324 to 1415; even more preferably SEQ ID Nos. 1258 to 1289, or SEQ ID Nos. 1290 to 1323, or SEQ ID Nos. 1324 to 1371, or SEQ ID Nos. 1372 to 1415.

TABLE 13

Preferred identical sequence and complementary primer sequences specific for the bisulfite-converted sense strand of the promoter region of the LINE-1 element.

| Identical sequence | SEQ ID No. | Complementary | SEQ ID No. |
|---|---|---|---|
| GTGATTTTTGTATTTTATT | 1049 | CTCTATATTTCCTAAATCTA | 1097 |
| GGTTTATTTTATTAGGGAGT | 1050 | TTAACCTACCTTACTAAATT | 1098 |
| AGGGAGTGTTAGATAGTGGG | 1051 | TAAATAATATCCTACAAAAT | 1099 |
| AGGTATTGTTTATTTGGGA | 1052 | CACATCACTTTCAAATACAC | 1100 |

TABLE 13-continued

Preferred identical sequence and complementary primer sequences specific for the bisulfite-converted sense strand of the promoter region of the LINE-1 element.

| Identical sequence | SEQ ID No. | Complementary | SEQ ID No. |
|---|---|---|---|
| TAAGGGGTTAGGGAGTTTTT | 1053 | ATTTAATCTTTTCACATAAT | 1101 |
| TTTTTGAGTTAAAGAAAGGG | 1054 | CTTAAAAACTTTACTCATTT | 1102 |
| AGATTATATTTTATATTTGG | 1055 | TTATTCTTTTTTCTCTAAAC | 1103 |
| TTGATTGTTAGTATAGTAGT | 1056 | TTCATTTCATTCATTTCATC | 1104 |
| TTTGAGATTAAATTGTAAGG | 1057 | ATACCCTTTCTTCCAATTAA | 1105 |
| TTATTGTTTAGGTTTGTTTA | 1058 | CCTAAAACTTCTACATTCTT | 1106 |
| GTTTAGGTAAATAAAGTAGT | 1059 | ATTTTCAACTCCATCAACTC | 1107 |
| AATTGGGTGGAGTTTATTAT | 1060 | TTATTCTAATTATACATTCT | 1108 |
| TAGTTTAAGGAGGTTTGTTT | 1061 | AAAATTTTCAACTTCTTTAC | 1109 |
| GTTTTTGTAGGTTTTATTTT | 1062 | GTAACTCAAAATAATTTAAT | 1110 |
| TGGGGGTAGGGTATAGATAA | 1063 | AAAACCTTCTTCTCTCAACT | 1111 |
| ATAAAAGATAGTAGTAATT | 1064 | GTCAAATCATTCTCCATCC | 1112 |
| TTTGTAGATTTAAGTGTTTT | 1065 | ATTCTATTACTAATAAAAAA | 1113 |
| TGTTTGATAGTTTTGAAGAG | 1066 | GTTCCTTTAAAAAAAAAAAA | 1114 |
| GAGTAGTGGTTTTTTTAGTA | 1067 | TTTAAAATTTCCAATTTTTC | 1115 |
| GGTAGATAGATTGTTTTTTT | 1068 | CCCATCTTTATAATTTTATC | 1116 |
| AAGTGGGTTTTTGATTTTTG | 1069 | TAATCTTTAATAATAATAAT | 1117 |
| ATTTTCGAGTAGTTTAATTG | 1070 | TAAATATCCTTTCTAATTAT | 1118 |
| GGAGGTATTTTTTAGTAGGG | 1071 | CAAACAAAACCCTCAACTAC | 1119 |
| GGGTATATTGATATTTTATA | 1072 | GTATAAAATATCAATATACC | 1120 |
| GTAGGGTATTTTAATAGATT | 1073 | AAATACCTCCCAATTAAACT | 1121 |
| TGTAGTTGAGGGTTTTGTTT | 1074 | AAAATCAAAAACCCACTTAA | 1122 |
| TTAGAAGGAAAATTAATAAT | 1075 | AAAAAAACAATCTATCTACC | 1123 |
| ATTAGAAAGGATATTTATAT | 1076 | GTTCTCAAATCTCCAACTA | 1124 |
| AAAATTTATTTGTATATTAT | 1077 | ACTAAAAAAACCACTACTCT | 1125 |
| TATTATTAAAGATTAAAAGT | 1078 | AAACAAAAACACTTAAATCT | 1126 |
| AGATAAAATTATAAAGATGG | 1079 | ATTACTACTATCTTTTTATT | 1127 |
| GGAAAAAATAGAATAGAAAA | 1080 | CCCCAAAAATAAAACCTACA | 1128 |
| AAAAATTGGAAATTTTAAAA | 1081 | CAAACCTCCTTAAACTATAA | 1129 |
| TTTTTTTTTTTTAAAGGAA | 1082 | TTTACCTAAACAAACCTAAA | 1130 |
| TAGTTTTTTATTAGTAATAG | 1083 | CAATTTAATCTCAAACTACT | 1131 |
| AATAAAGTTGGATGGAGAAT | 1084 | CCAAATATAAAATATAATCT | 1132 |
| AGTTGAGAGAAGAAGGTTTT | 1085 | CACCCCTTTCTTTAACTCAA | 1133 |
| AGACGATTAAATTATTTTGA | 1086 | AAAAACTCCCTAACCCCTTA | 1134 |
| GGAGGATATTTAAATTAAAG | 1087 | TCCCAAATAAAACAATACCT | 1135 |

TABLE 13-continued

Preferred identical sequence and complementary primer sequences specific for the bisulfite-converted sense strand of the promoter region of the LINE-1 element.

| Identical sequence | SEQ ID No. | Complementary | SEQ ID No. |
|---|---|---|---|
| GTAAAGAAGTTGAAAATTTT | 1088 | TCTAACACTCCCTAATAAAA | 1136 |
| TGAAAAAAATTTAGAAGAAT | 1089 | ACCTCAAATAAAAATACAAA | 1137 |
| GTATAATTAGAATAATTAAT | 1090 | ACCATCTTAACTCCTCCCCC | 1138 |
| ATAGAGAAGTGTTTAAAGGA | 1091 | CACTAAAACATAATTAAACA | 1139 |
| GTTGATGGAGTTGAAAATTA | 1092 | AAAAATTACTAATAACCTCA | 1140 |
| TGAAGAATGTAGAAGTTTTA | 1093 | CCAAAAAAACAATAACATCA | 1141 |
| ATTAATTGGAAGAAAGGGTA | 1094 | AAACAATAACATCAAAAACA | 1142 |
| TTAGTAATGGAAGATGAAAT | 1095 | GAAAACAAACCATAATAACA | 1143 |
| AGAAGGGAAGTTTAGAGAAA | 1096 | GAACCATAATAACAATAACA | 1144 |
|  |  | TAACAATAACAATTTTATCA | 1145 |

TABLE 14

Preferred identical sequence and complementary primer sequences specific for the bisulfite-converted antisense strand of the promoter region of the LINE-1 element.

| Identical sequence | SEQ ID No. | Complementary | SEQ ID No. |
|---|---|---|---|
| AattttgttgatTTtttTaa | 1146 | tctAcatttccatctAaAAt | 1193 |
| gtgtTtTtattttTTttTagt | 1147 | taAAAaAtAccaAacaAtAA | 1194 |
| aatgtgtttgTtTttgTttt | 1148 | AaAttccctttctAaAtcaa | 1195 |
| TaattttggatTtttTTtgT | 1149 | actatatcccacacctAAct | 1196 |
| tTTTtTttaTaTaTtgTtttg | 1150 | acaAcaAtctAaAatcaaac | 1197 |
| gtatgtggtgtTtttgttTt | 1151 | AActtActtaAAtaaacaaa | 1198 |
| aTatTtttatttTtgTTtttT | 1152 | caccacaActcaaAAaAAcc | 1199 |
| aggttgttTagtttTTatgt | 1153 | ctAAAAAcaAAAacaAaca | 1200 |
| tgTaTtgtggtTtgagagat | 1154 | AacttaaAtAtccctAtctA | 1201 |
| aTtatgtggtTaattttgga | 1155 | aaAaAaAcaAtAAttctccc | 1202 |
| gatttggggtggagagttTt | 1156 | caaAtAAAtccctAactcct | 1203 |
| ttTTtgggtatTTttgttga | 1157 | ccaAcaAAAAcacactAaca | 1204 |
| tgttaaagtTtTTTattatt | 1158 | tAaAAAtcctAtctAttaAa | 1205 |
| gTtttatgaatTtgggtgTt | 1159 | AaaAaccaaaaAtaAataaa | 1206 |
| tgttgaattgatTTTtttaT | 1160 | aacaAaacaaaActAAatAA | 1207 |
| atTagagaTtaggattgTaa | 1161 | tAaAaAaaAaaAActtcaAa | 1208 |
| ttggtagatTttTTtTTatT | 1162 | aaccaaaAAcaaaAaaAttA | 1209 |
| gTaTaTtgatgggtTtttgaT | 1163 | tataactaAaataaccaata | 1210 |
| tTttttaattgTagaattta | 1164 | AatAAaActAaaaaccaaAA | 1211 |

TABLE 14-continued

Preferred identical sequence and complementary primer sequences specific for the bisulfite-converted antisense strand of the promoter region of the LINE-1 element.

| Identical sequence | SEQ ID No. | Complementary | SEQ ID No. |
|---|---|---|---|
| tttgTtTattagttgatgTa | 1165 | aatAcaAaaAcctcaAAaAc | 1212 |
| ttaTattttggTatgattttt | 1166 | caAcaatAAaaAatAaaatA | 1213 |
| gtgTttTTttTaggagTtTt | 1167 | aAaAaaaaaaAaataaaaaA | 1214 |
| aaagtattttattTTtTTtt | 1168 | AaaatatAAAactatAtAaa | 1215 |
| aaattTtgggttgaaaattT | 1169 | tAaaaAtAatAtAAaAaatA | 1216 |
| ggTtgTTTttaaTattttttt | 1170 | tAcaAAatattatccaAAaA | 1217 |
| aTaattatgtgtTtttggagt | 1171 | AattcaAAaaatacaAaAaa | 1218 |
| gttTTattTtTTaTatTaTt | 1172 | AattcaccaaaAttAaaatA | 1219 |
| aTatagtTTTatatttTttg | 1173 | aaaAcccatcaAactaacaA | 1220 |
| TtgataTTTttttTttTTagt | 1174 | AaaAaAaAtAAAAAccaata | 1221 |
| TTTgaggTttTtgTattTttt | 1175 | aAccaaactaaActtcataa | 1222 |
| atTagTtTTtttaagTaTtt | 1176 | aaatAttAaAaAattttAtc | 1223 |
| ttttTaaTttTttttgTTtttg | 1177 | AcactaaacatAAaaaAAaa | 1224 |
| gaagTTttTtttTtTtTagTt | 1178 | atcatAccaaaatAtaaaAa | 1225 |
| tgttTtgttgTtggtgagga | 1179 | atcaactaatAaAcaaaatc | 1226 |
| tgatggtgatgtaTagatgg | 1180 | caAAatcaaattcacacata | 1227 |
| TTtTagTtgTaggtTtgttg | 1181 |  |  |
| agtgtgTTTTtgTtgggggg | 1182 |  |  |
| TTTaTttgaggaggTagtTt | 1183 |  |  |
| gTtgtTagaTagggaTaTttt | 1184 |  |  |
| TtgtgTTTtgTTTTTagagg | 1185 |  |  |
| agTgtggtgggTtTTaTTT | 1186 |  |  |
| ttaagTaagTTtgggTaatg | 1187 |  |  |
| ttqatTtTagaTtgTtgtgT | 1188 |  |  |
| TTaggtgtgggatatagtTt | 1189 |  |  |
| tttTttttgaTtTagaaaggg | 1190 |  |  |
| TtggTaTtTTTTtagtgagat | 1191 |  |  |
| TagatggaaatgTagaaatT | 1192 |  |  |

TABLE 15

Preferred identical sequence and complementary primer sequences specific for the bisulfite-converted sense strand of the Alu element.

| Identical sequence | SEQ ID No. | Complementary | SEQ ID No. |
|---|---|---|---|
| GTTTGTAATTTTAGTATTTT | 1228 | CCCAAACTAAAATACAATAA | 1238 |
| ATTTTAGTATTTTGGGAGGT | 1229 | ATTCTCCTACCTCAACCTCC | 1239 |

TABLE 15-continued

Preferred identical sequence and complementary primer sequences specific for the bisulfite-converted sense strand of the Alu element.

| Identical sequence | SEQ ID No. | Complementary | SEQ ID No. |
|---|---|---|---|
| GGATTATTTGAGGTTAGGAG | 1230 | TTTTATATTTTTAATAAAAA | 1240 |
| GAGATTATTTTGGTTAATAT | 1231 | CATATTAACCAAAATAATCT | 1241 |
| TGGTTAATATGGTGAAATTT | 1232 | TCTCCTAACCTCAAATAATC | 1242 |
| GTTTTTATTAAAAATATAAA | 1233 | CAAATACTAAAATTACAAA | 1243 |
| TTAAAAATATAAAAATTAGT | 1234 | | |
| GTTTGTAATTTTAGTTATT | 1235 | | |
| GGGAGGTTGAGGTAGGAGAA | 1236 | | |
| GTTATTGTATTTTAGTTTGG | 1237 | | |

TABLE 16

Preferred identical sequence and complementary primer sequences specific for the bisulfite-converted antisense strand of the Alu element.

| Identical sequence | SEQ ID No. | Complementary | SEQ ID No. |
|---|---|---|---|
| TTTAGGTTGGAGTGTAGTGG | 1244 | ATCCCAACACTTTAAAAAAC | 1251 |
| ATTTTTTTGTTTTAGTTTTT | 1245 | AATCACCTAAAATCAAAAAA | 1252 |
| GAGTAGTTGGGATTATAGG | 1246 | TCCTAACCAACATAATAAAA | 1253 |
| TTTTTGTATTTTTAGTAGAG | 1247 | TACTAAAAATACAAAAATTA | 1254 |
| TTTTATTATGTTGGTTAGGA | 1248 | GCCTATAATCCCAACTACT | 1255 |
| ATTTTTTGATTTTAGGTGAT | 1249 | GAAAAACTAAAACAAAAAA | 1256 |
| TTTTTAAAGTGTTGGGATTA | 1250 | CCACTACACTCCAACCTAAA | 1257 |

TABLE 17

Preferred identical sequence and complementary primer sequences specific for the bisulfite-converted sense strand of the HERV-K element.

| Identical sequence | SEQ ID No. | Complementary | SEQ ID No. |
|---|---|---|---|
| gtagttgagataagaggaag | 1258 | cttaatatttattaatcatt | 1290 |
| agggagaaattatttttaggg | 1259 | tacatacacataaacatctc | 1291 |
| taaagtattgagatgtttat | 1260 | ttccctatctcaataaataa | 1292 |
| atatattttttttttagaga | 1261 | aacattccattacccaaaaa | 1293 |
| gaaatatttataggtgtgga | 1262 | ctcacataaaaaaaaacctt | 1294 |
| ggggtaaattaaaattaaaa | 1263 | taaaaaataataataactct | 1295 |
| atagaataattttgtttatg | 1264 | tccatttaacccaaaattta | 1296 |
| agtaggtaggaagggtaata | 1265 | aacaaaaaaattttttcttaa | 1297 |
| gttttagaattatttttaaat | 1266 | actaacaacaaacaaaacaa | 1298 |
| Ggaagttgtataatagattg | 1267 | tcctaacaccaaatttaaat | 1299 |
| aattagtggggttattagag | 1268 | ctaaaataaaattatcttct | 1300 |
| gatttaattgttagtagttt | 1269 | tattctaaaatcataaacct | 1301 |
| tatggtattatttagtaggt | 1270 | aacttaccaattttaatca | 1302 |
| gaaagagggagtaaaatagt | 1271 | aatcaaaatataaataaata | 1303 |
| gaattgatggggtataagaa | 1272 | aactaatttaataactatat | 1304 |
| taagtattaatgtaaaatga | 1273 | tatacttatatttatctaaa | 1305 |
| agagtttgggaaaaaattta | 1274 | cttaaaacaaatttttccctt | 1306 |
| atagtaagataaggtttaaa | 1275 | catcctaatactctccctaa | 1307 |
| gatgtaattttagagtatgt | 1276 | cattataaaacttcaaatat | 1308 |
| atattgggttagttaatgtt | 1277 | taaaattttccactaactta | 1309 |
| ataaaaattttttataggag | 1278 | cattactaaaaccatcaata | 1310 |
| ttagaagtgtattaaagtat | 1279 | tttactaataaatataaaac | 1311 |
| tggtttatatagggttaaaa | 1280 | atataaaatctcaatactttt | 1312 |
| ttagttatatggatggataa | 1281 | aaccttaatatataacaaaa | 1313 |
| gatttaattttttaattggta | 1282 | aactcccctaaaaacaaaaa | 1314 |
| atatttgattgaaatatta | 1283 | ctctacctattattataata | 1315 |
| gagtattattgggatatggt | 1284 | tctaaaattacatctaatcc | 1316 |
| ttatgattataaattttata | 1285 | accctacctactaaataata | 1317 |
| agtagatataggagatttta | 1286 | acctcctataattaattata | 1318 |
| tttgtttaggaaagttaggt | 1287 | atttttaataaaaactaaaata | 1319 |
| tttattgagatagggaaaaa | 1288 | cataaacaaaataaaaaatt | 1320 |
| ataaatattaagggaattta | 1289 | ctaatcctcctcaacacaaa | 1321 |
| ccttcaaacatctatttaac | 1322 | | |
| ttaacaacatctcaaaacaa | 1323 | | |

TABLE 18

Preferred identical sequence and complementary primer sequences specific for the bisulfite-converted antisense strand of the HERV-K element.

| Identical sequence | SEQ ID No. | Complementary | SEQ ID No. |
|---|---|---|---|
| tTTTttagtatttattgatT | 1324 | atctatAaccttaccccccaa | 1372 |
| ggggatgtgtTagggtTaTa | 1325 | aacaAatActtAaaAAcaAc | 1373 |
| tgTatTatagaTaaggtaaa | 1326 | aatctcaaAtacccaAAAac | 1374 |
| atatgTataTaTataaaTat | 1327 | tccccatAtAaAaAtctAaa | 1375 |

TABLE 18-continued

Preferred identical sequence and complementary primer sequences specific for the bisulfite-converted antisense strand of the HERV-K element.

| Identical sequence | SEQ ID No. | Complementary | SEQ ID No. |
|---|---|---|---|
| tttttTTTtatTtTagtaga | 1328 | AaAAaAAattaAtataaAaA | 1376 |
| gatgtTttTTtTttTtTtTa | 1329 | caccttaAAActAAaAAtAA | 1377 |
| ggatggtTaggtTtttTTTt | 1330 | cacatctccctctcaAaAaa | 1378 |
| agattagggagtggtgatga | 1331 | tttttctttccaaAtctct | 1379 |
| ttgaTaTagTaTatgtttTa | 1332 | tttctctAAAAtAaaAAtac | 1380 |
| gattaaTagTatTtTaaggT | 1333 | cttaActtcattaaaattct | 1381 |
| gtaaTaatTtTatTtTtTtt | 1334 | aAcaAAtaAAaaAAAtaata | 1382 |
| gatttataatTatagtaTtt | 1335 | aattacaAaAAtAatatat | 1383 |
| aaTtTTtgTaattgTTtTag | 1336 | ccaactAccaAtaActtatc | 1384 |
| tggaaatgtTtaaagtgaga | 1337 | aAtaAAcaAAAtaAtAaatt | 1385 |
| gTtTagaTtTattataaatt | 1338 | ccaAataaaAAtcttttaA | 1386 |
| TtgTaattaaagtaaaaatg | 1339 | tttacaatttaaAacttAAt | 1387 |
| ggtttaataaTtatatttTT | 1340 | aAttaAaActatctAccttta | 1388 |
| tTttggggtagagattTTtt | 1341 | ccattaaAccattaaaaAAa | 1389 |
| TtgagTaattgtggtagaat | 1342 | AtcaaaatAAtcatttaaaa | 1390 |
| TTaaaTtaaaaTttTtgtat | 1343 | tAataaaaatAAAcaaccat | 1391 |
| gataagtgaatTtaTtgtta | 1344 | caaccccactAtcccaaAt | 1392 |
| aggTattaaaTatTTTggtg | 1345 | AtAccaAtccaAAaAacaAA | 1393 |
| taTttTtataggattatTTa | 1346 | aaatcaAtAAccaaaaaatt | 1394 |
| aTttTaaatgtTtagtgggt | 1347 | tAaccaaAatAAAatatata | 1395 |
| tattttTTTatgtTttatttt | 1348 | taattcaAaaAaaatccaAc | 1396 |
| gTtagattaagttgTatTtg | 1349 | AaAAttAccaatAcaAAact | 1397 |
| agttgTaTaTatgaaatgtg | 1350 | atcccttaAccccactccaa | 1398 |
| tTtTaaTatTTTttgtagTT | 1351 | AtAAaaatAacccaAacaaa | 1399 |
| gTTaTttttTTattgTtgga | 1352 | AAaaaaAtAActtacacaAA | 1400 |
| TtattttgtTtgggtTattt | 1353 | aaAaaacttccattttata | 1401 |
| tatTtTTTagTaatttttga | 1354 | acttattcacatttcatAtA | 1402 |
| GatttTtttTtgaattaTaaa | 1355 | cacatAaaAAaaaactaatt | 1403 |
| TTTatTtttggtTataatttt | 1356 | taatAataAtAtatAAAtac | 1404 |
| ggTTTtaagTaatgtaaaat | 1357 | cttatcaaaAatcattaaaa | 1405 |
| aatTTttTTaagTtgttttTT | 1358 | tAcacaAtAaAtccaActA | 1406 |
| TTttaatatatggTaggagt | 1359 | ctataacctAtAaaaattAt | 1407 |
| aagattagtTTTtaTagtTtT | 1360 | AcaaaaAaattctacaaAat | 1408 |
| tTaaatttagaatgaTattg | 1361 | tAaAtctAaAcatcactAAA | 1409 |
| tgTttgggTTataagTatag | 1362 | tAttAttaAtctAcaAAtAt | 1410 |
| gTtTtttttgaaTTttgtTtt | 1363 | aAAAtAAtAcaaAatAtAct | 1411 |
| atagttgatTtgTatTtatg | 1364 | taAtataaAaAAaaaAcatA | 1412 |
| taTtgtttttaTtTTTtTttt | 1365 | actAccttaAAAActAAaAAt | 1413 |
| gaTttTtTaataatttTatg | 1366 | tattAtcttAtAaccctAac | 1414 |
| aaatggttTtaaagTtgTtt | 1367 | tccaccttatAaAaaacacc | 1415 |
| TTtTTaTaTTtgtgggtgtt | 1368 | | |
| Taatagtggggagagggtga | 1369 | | |
| ggaaaTagatgTTttTTtTt | 1370 | | |
| Tttgagattagggagtggtg | 1371 | | |

The skilled person will also be able to provide primers for any other transposon or fragment thereof in accordance with the scheme explained above.

According to the invention, the determination of the normalized DNA methylation level is performed via the ratio of the amplificates formed in the two amplification steps (steps a) and b)). In particular embodiments, the ratio is determined via the quantities of amplificate formed, more preferably via the increase of amplificate formed per amplification cycle, even more preferably via the cycle threshold (Ct) value during a real time PCR.

In one embodiment, the total amount of the two amplificates formed is determined after an identical number of amplification cycles and placed in relation to one another. The skilled person knows a variety of methods for determining the amplificates formed, including spectroscopic methods, staining by means of ethidium bromide or silver, and densitometric determination, or radioactive labeling with subsequent determination by, for example, scintillation measurement.

In a preferred embodiment, the determination of the amplificates formed in the two amplification steps is effected by means of real time PCR during the formation of the amplificates themselves. In another preferred embodiment, the determination of the amplificates formed in the two amplification steps is effected simultaneously during a real time PCR.

After the determination of the amplificates formed in the two amplification steps, the value for the amplificate in the second amplification step (step b)) is normalized by means of the value for the amplificate in the first amplification step (step a)); for example, by division or subtraction of the determined values. Thus, a methylation level normalized to the total occurrence of the examined DNA region is determined (i.e., the normalized (de)methylation), which can be assumed to be representative for the methylation level of the total genome.

In a preferred embodiment, the amplifications of steps a) and b) as well as the determination of the amplificates formed were effected by means of real time PCR. Thus, cycle threshold (Ct) values are determined, both for the primer pair that is specific for at least one differentially methylated position of the transposon (step b), $Ct_m$), and for the primer pair that is specific for a non-differentially methylated region of the transposon (step a), $Ct_k$). The Ct value describes the cycle of PCR in which the fluorescence rises significantly above the background fluorescence for the first time, and thus marks the beginning of the exponential phase of PCR. Thereafter, the Ct value from step a) is subtracted from the Ct value from step b) to arrive at the normalized methylation level ($\Delta$Ct). Thus, $\Delta$Ct can be calculated as: $\Delta Ct = Ct_m - Ct_k$.

As previously mentioned, the process according to the invention also allows a comparison to be made between the methylation levels of two genomes having different genomic settings (for example, in erroneous multiplications of individual chromosomes, which in part occur in tumor cells; trisomies or the like). When the normalized methylation level of a DNA from a "normal genome" (control) is compared with that from a patient, different methylation levels between the two genomes can be indications of a disease. Thus, the process according to the invention for determining a relative DNA methylation level is of immense importance to (clinical) diagnostics.

Therefore, a second aspect of the present invention relates to a process for determining the relative DNA methylation level, comprising the steps: a) determination of the normalized methylation level according to steps a) to c) of the first aspect of the invention for a first DNA and a second DNA; and b) determination of the relative DNA methylation level via the ratio of the normalized methylation levels determined for the first and second DNAs.

In other words, the above described process of the first aspect of the invention is performed for two different DNAs, which may originate, for example, from different (clinical) samples, and the obtained normalized methylation levels of the two DNAs are divided by one another. Then, from the ratio of the two methylation levels, conclusions can be drawn and/or diagnoses made, for example, with respect to a cancer.

In one embodiment, the relative methylation level of more than two DNAs is determined. In another embodiment, the methylation level of at least one DNA to be examined is divided by a mean value of the methylation levels from more than one "normal genome". Thus, for example, the normalized methylation level of the DNA from $\geq 10$, $\geq 50$ or $\geq 100$ healthy subjects is determined, and the mean value calculated therefrom is used to calculate a ratio from the normalized DNA methylation level of a patient. In another embodiment, the normalized DNA methylation level of a patient is used to calculate a ratio from the normalized.

DNA methylation level of an individual sample or from the average normalized DNA methylation level of several samples/DNAs (preferably $\geq 10$, $\geq 50$ or $\geq 100$), wherein these latter samples contain DNA having the methylation pattern of a disease.

In one embodiment, at least one of the two DNAs originates from a sample; preferably, the DNA has been isolated from this sample. In a preferred embodiment, both DNAs originate from a sample each. In another preferred embodiment, the first sample is a sample from a healthy subject, while the second sample is a sample from a patient. In a further preferred embodiment, the first sample is a sample comprising at least one tumor cell, and the second sample is a sample from a patient. Thus, the first sample/DNA serves as a negative or positive control with which the sample from the patient is compared. In another embodiment, the positive control is HT1376 DNA.

In another embodiment, the determination of the normalized methylation level of one of the two DNAs was performed more than a day, a week, a month or a year before the determination of the normalized methylation level of the second DNA.

In another embodiment, at least one of the two samples is selected from the group consisting of a blood sample, a tissue sample, a saliva sample, a urine sample, a smear and a stool sample. In a preferred embodiment, the sample is a urine sample.

In another step of the process according to the invention, the determination of the relative DNA methylation level is effected via the ratio of the normalized methylation levels determined for the first and second DNAs, for example, by dividing or subtracting the determined values.

In a preferred embodiment, the determination of the normalized methylation level is performed by real time PCR as described above. If the difference of the $\Delta$Ct value of the second DNA ($\Delta Ct_2$), which may originate from a patient sample to be examined, for example, and the $\Delta$Ct value of the first DNA ($\Delta Ct_1$), which may originate from a reference sample, for example, is calculated as $\Delta\Delta Ct = \Delta Ct_2 - \Delta Ct_1$, then the relative methylation level of the second DNA can be stated as $2^{-\Delta\Delta Ct}$. Thus, the relative methylation of the second DNA to the first DNA is calculated if primers specific for a cytosine of a CpG were used for the amplification, and the relative demethylation is calculated if primers specific for the bisulfited cytosine of a CpG were used for the amplification.

The skilled person knows that the ratio of the amplificates formed in the two amplification steps can be determined by means of repeated measurement and forming of mean values in order to increase the accuracy of the process. Therefore, in one embodiment of the invention, a mean value of several amounts of amplificate or Ct values determined for a DNA is calculated.

In another embodiment, the invention discloses a process for the detection or diagnosis of a disease related to an altered DNA methylation. In a preferred embodiment, such a disease is a tumor. In another preferred embodiment, the relative methylation level of the DNA from a reference sample and that from a sample to be examined (for example, from one of the samples stated above, such as a urine or saliva sample from a patient) is determined. In a preferred embodiment, the tumor is diagnosed/detected in a subject or in a sample from a subject.

In one embodiment of the invention, the reference sample originates from a healthy subject, and/or the DNA obtained therefrom has a methylation level known to prevail when no tumor is present. In another embodiment of the invention, the reference sample originates from a subject afflicted with a tumor, and/or it has a methylation level known to prevail when a tumor is present. In a preferred embodiment of the invention, the reference sample originates from a diseases subject in whom the tumor disease has been typed. The reference sample may also consist of cultured and preferably typed tumor cells, such as HT1376 cells. As mentioned above, mean values of several reference samples may also be used for the reference sample.

In one embodiment of the invention, the collection of the samples from the subject is part of the process according to the invention, and in another particular embodiment of the invention, the collection of the samples from the subject is not part of the process according to the invention.

If the normalized DNA methylation level of the patient sample deviates from the normalized DNA methylation level of the reference sample, i.e., if a division of the two values for forming the relative DNA methylation level yields a value not equal to 1, for example, then this is an indication of the presence of a disease related to an altered DNA methylation, preferably a tumor.

In one embodiment, a reduced DNA methylation, a reduced DNA demethylation, an increased DNA methylation or an increased DNA demethylation of the DNA from the sample as compared to the DNA from the reference indicate the presence of such a disease.

In a preferred embodiment, a reduced DNA methylation or an increased DNA demethylation of the DNA from the sample as compared to the DNA from the reference indicate the presence of a tumor. In an even more preferred embodiment of the invention, the difference in the reduction of DNA methylation or in the increase of DNA demethylation correlates with the aggressiveness of the tumor.

In further preferred embodiments, this tumor is selected from the group consisting of: bladder tumor, prostate tumor, breast cancer, bronchial carcinoma, leukemias, intestinal cancer, testicular tumor, nasopharyngeal carcinoma, cervical cancer, pancreatic carcinoma and/or gastric cancer.

In a further aspect, the invention relates to an oligonucleotide that can be used, for example, as a primer in the amplification steps in the processes of the present invention.

In one embodiment, the oligonucleotide is specific for a transposon or fragment thereof, wherein said transposon is selected from the group consisting of a LINE element, an Alu element, a HERV element, a HERV-K element or a fragment thereof. In a particular embodiment, the transposon is a LINE-1 element or fragment thereof. More preferably, the fragment of the transposon is the promoter region of the LINE-1 element. In a particular embodiment, the oligonucleotide has an identical sequence or is complementary to the sense or antisense strand of the bisulfited transposon and comprises at least one differentially methylated position of the transposon. In a further preferred embodiment, the oligonucleotide has an identical sequence or is complementary to the sense or antisense strand of the bisulfited transposon and comprises no differentially methylated position of the transposon.

In a preferred embodiment, the oligonucleotide comprises at least one differentially methylated position of the transposon. In a further embodiment, the oligonucleotide is specific for a region of the transposon that is always non-methylated; preferably, for a region that contains no cytosines of CpG dinucleotides.

In a further preferred embodiment, the oligonucleotide has a length of 15 nucleotides; preferably 18, 19, 20, 21, 22, 23, 24 or 25 nucleotides. In a further preferred embodiment, the oligonucleotide has a length of 18 and 35 nucleotides; more preferably, it has a length of 20 and 30 nucleotides.

In another embodiment, the oligonucleotide has a sequence selected from the group consisting of SEQ ID Nos. 3 to 1415.

In a further embodiment, the oligonucleotide comprises a sequence selected from the group consisting of SEQ ID Nos. 3 to 1048, wherein the sequence may be truncated or (according to the respective transposon) extended from the 5' end and/or from the 3' end. In a preferred embodiment, the oligonucleotide according to the invention is extended by from 1 to 20 nucleotides from the 5' end and/or from the 3' end; even more preferably, the oligonucleotide is extended by from 5 to 15 nucleotides from the 5' end and/or from the 3' end. In another embodiment, the oligonucleotide is truncated by up to a total of 5 nucleotides from the 5' end and/or from the 3' end, wherein the oligonucleotide always remains specific for at least one CpG or bisulfited CpG.

In a further embodiment, the oligonucleotide comprises said at least one nucleotide specific for a differentially methylated position at any position within the oligonucleotide, i.e., at the 5' end of the oligonucleotide, at the 3' end or at any position between. In a particularly preferred embodiment, said at least one nucleotide specific for a differentially methylated position is at the 3' end of the nucleotide. This has the advantage of an increased specificity.

In a further embodiment, the oligonucleotide is selected from the group consisting of SEQ ID Nos. 3 to 436; more preferably SEQ ID Nos. 3 to 112, or SEQ ID Nos. 113 to 220, or SEQ ID Nos. 221 to 336, or SEQ ID Nos. 337 to 436; even more preferably SEQ ID Nos. 3 to 57, or SEQ ID Nos. 58 to 112, or SEQ ID Nos. 113 to 166, or SEQ ID Nos. 167 to 220, or SEQ ID Nos. 221 to 278, or SEQ ID Nos. 279 to 336, or SEQ ID Nos. 337 to 386, or SEQ ID Nos. 387 to 436.

In further embodiments, the oligonucleotide is selected from the group consisting of SEQ ID Nos. 437 to 612; more preferably SEQ ID Nos. 437 to 476, or SEQ ID Nos. 477 to 522, or SEQ ID Nos. 523 to 570, or SEQ ID Nos. 571 to 612; even more preferably SEQ ID Nos. 437 to 456, or SEQ ID Nos. 457 to 476, or SEQ ID Nos. 477 to 499, or SEQ ID Nos. 500 to 522, or SEQ ID Nos. 523 to 546, or SEQ ID Nos. 547 to 570, or SEQ ID Nos. 571 to 591, or SEQ ID Nos. 592 to 612.

In further embodiments, the oligonucleotide is selected from the group consisting of SEQ ID Nos. 613 to 1048; more preferably SEQ ID Nos. 613 to 708, or SEQ ID Nos. 709 to 796, or SEQ ID Nos. 797 to 922, or SEQ ID Nos. 923 to 1048; even more preferably SEQ ID Nos. 613 to 660, or SEQ ID Nos. 661 to 708, or SEQ ID Nos. 709 to 752, or SEQ ID Nos. 753 to 796, or SEQ ID Nos. 797 to 859, or SEQ ID Nos. 860 to 922, or SEQ ID Nos. 923 to 985, or SEQ ID Nos. 986 to 1048.

In further embodiments, the oligonucleotide is selected from the group consisting of SEQ ID Nos. 1049 to 1227; more preferably SEQ ID Nos. 1049 to 1145, or SEQ ID Nos. 1146 to 1227; even more preferably SEQ ID Nos. 1049 to 1096, or SEQ ID Nos. 1097 to 1145, or SEQ ID Nos. 1146 to 1192, or SEQ ID Nos. 1193 to 1227.

In further embodiments, the oligonucleotide is selected from the group consisting of SEQ ID Nos. 1228 to 1257; more preferably SEQ ID Nos. 1228 to 1243, or SEQ ID Nos. 1244 to 1257; even more preferably SEQ ID Nos. 1228 to 1237, or SEQ ID Nos. 1238 to 1243, or SEQ ID Nos. 1244 to 1250, or SEQ ID Nos. 1251 to 1257.

In further embodiments, the oligonucleotide is selected from the group consisting of SEQ ID Nos. 1258 to 1415; more preferably SEQ ID Nos. 1258 to 1323, or SEQ ID Nos. 1324 to 1415; even more preferably SEQ ID Nos. 1258 to 1289, or SEQ ID Nos. 1290 to 1323, or SEQ ID Nos. 1324 to 1371, or SEQ ID Nos. 1372 to 1415.

EXAMPLES

Example 1

DNA from the urothelial carcinoma cell line HT1376, DNA from a urothelial carcinoma and from healthy bladder epithelium were isolated by means of a commercially available kit (Qiagen; QIAamp DNA blood kit). The DNA of the urothelial carcinoma cell line was diluted with DNA from the healthy bladder epithelium in different dilution stages. This was followed by a bisulfitation of the DNA in the different compositions by means of the EpiTect Bisulfite Kit (Qiagen). Subsequently, the determination according to the invention of the relative methylation level of the individual samples as compared to the DNA from the healthy bladder epithelium is performed.

For each sample, each value was determined in triplicate, and mean values were calculated.

The amplification was performed by means of real time PCR. Primers were used that were specific for the following LINE-1 promoter sequences:

```
                                    (SEQ ID No. 1417)
    5'-GCGCGAGTCGAAGTAGGGC
    for the forward primer (SEQ ID No. 1418)
    5'-CTCCGAACCAAATATAAAATATAATCTCG
    for the reverse primer
```

These two primers enclose a 193 bp region of the LINE-1 element and are specific for methylated DNA.

For the always non-methylated region, primers having the following sequences were used:

```
                                    (SEQ ID No. 1419)
    5'-AGGTTTTATTTTTGGGGGTAGGGTATAG
    as the forward primer (SEQ ID No. 1420)
    5'-CCCCTACTAAAAAATACCTCCCAATTAAAC
    as the reverse primer
```

The PCR was performed under the following conditions (per reaction):

| Reagent | Volume (μl) |
|---|---|
| Sybergreen (Qiagen) | 12.5 |
| 5' primer, 10 pmol/ml | 1 |
| 3' primer, 10 pmol/ml | 1 |
| DNA (10 ng) | 1 |
| Water | 10.5 |
| Sum | 25 |

| Cycler conditions |
|---|
| 95° C. for 15' |
| 95° C. for 55" |
| 54° C. for 30" 35x |
| 72° C. for 30" |
| 4° C. for ∞ |

Figure 1:
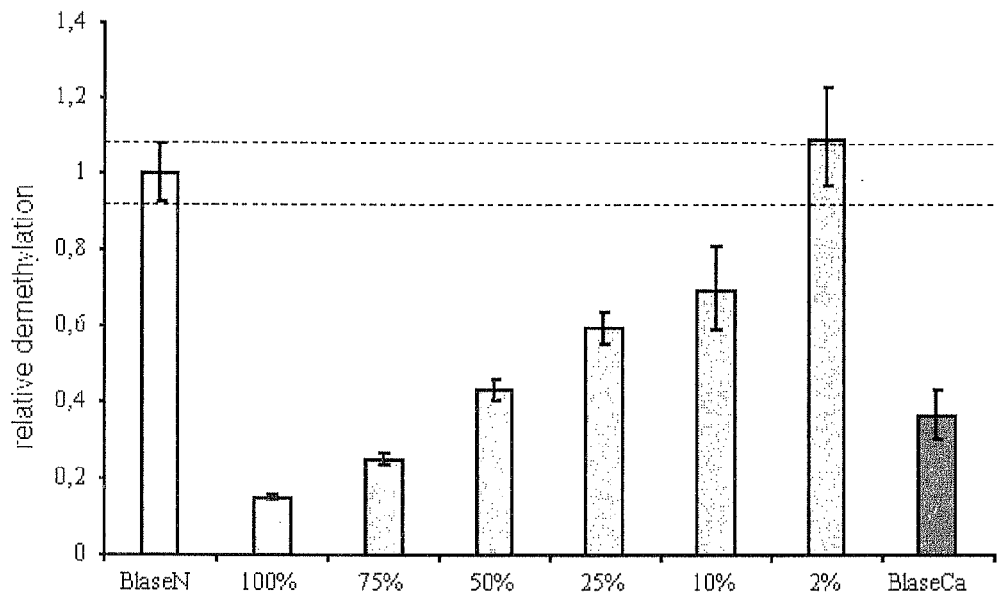
FIG. 1 shows the result of the determination of the relative DNA methylation of tumor DNA in different dilution stages (with healthy urothelium) according to a preferred embodiment of the invention.

The result of the examination using the primers specific for the methylated DNA is shown in FIG. 1. It can be seen that a reliable detection can be effected of 2 ng of the tumor DNA from a 1:10 mixture with DNA from healthy urothelium.

Example 2

Example 1 was repeated with primers that are specific for the demethylated LINE-1 sequence.

These primers had the following sequences:

```
                                    (SEQ ID No. 1421)
    5'-GTGTGTATTGTGTGTGAGTTGAAGTAGGGT
    for the forward primer (SEQ ID No. 1422)
    5'-ACCCTCCAAACCAAATATAAAATATAATCTCA
    for the reverse primer
```

These two primers enclose a 207 bp region of the LINE-1 element and are specific for demethylated DNA.

However, urine samples from healthy subjects and from urothelial carcinoma patients were employed as samples. One milliliter of urine and 10 ng of bisulfited DNA were employed.

Figure 2:
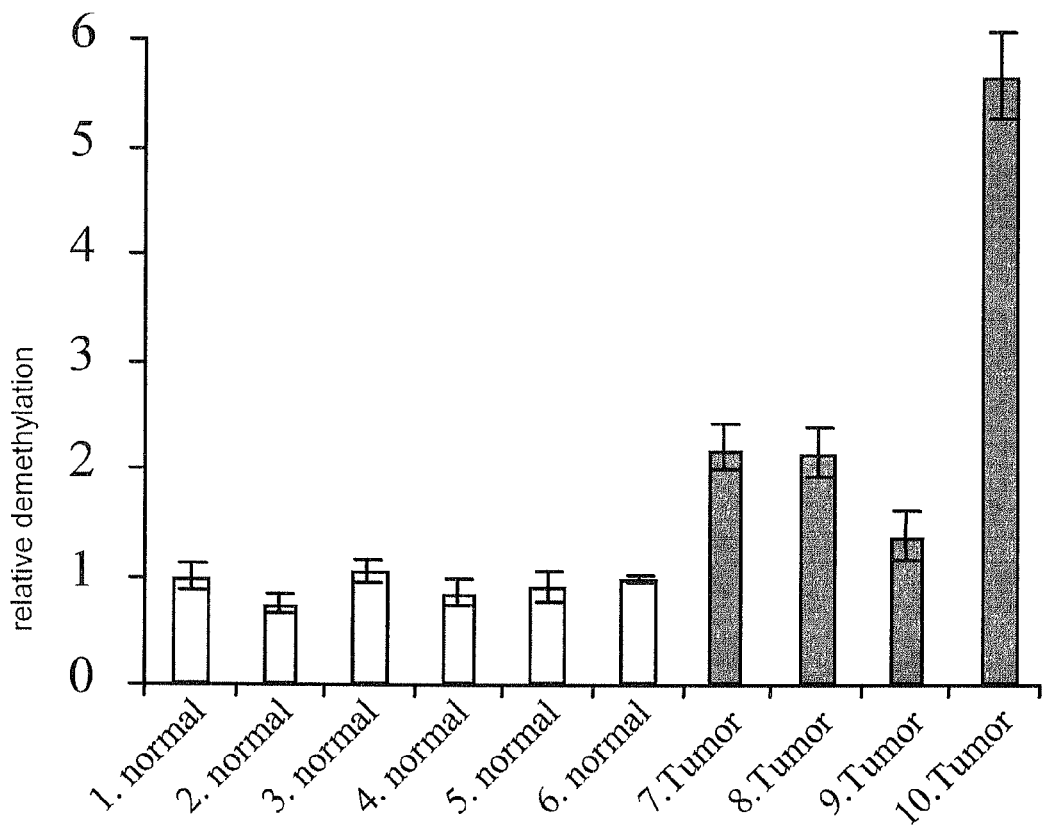
FIG. 2 shows the result of the determination of the relative DNA demethylation in 4 patient samples as compared to healthy subjects according to a preferred embodiment of the invention.

FIG. 2 shows the result of this experiment. It can be seen that a significant hypomethylation could be detected in 3 of 4 samples from the urothelial carcinoma patients as compared to the 6 control samples employed.

Embodiments

E1. A process for determining the normalized DNA methylation level, comprising the steps:
  a) quantitative determination of the presence of a transposon or fragment thereof in a DNA;
  b) quantitative determination of the presence of at least one differentially methylated C of a CpG dinucleotide within the same transposon or fragment thereof; and
  c) determination of the normalized DNA methylation level via the values determined in steps a) and b).

E2. The process according to embodiment E1, wherein said transposon or fragment thereof is selected from the group consisting of a LINE element, LINE-1 element, Alu element, HERV element and preferably the promoter region of a LINE-1 element.

E3. The process according to embodiment E1, wherein said DNA in step a) and/or in step b) is bisulfited DNA.

E4. The process according to embodiment E3, wherein:
  step a) comprises: amplification of the non-bisulfited DNA with at least one primer pair that is specific for a transposon or fragment thereof, or amplification of the bisulfited DNA with at least one primer pair that is specific for a bisulfited transposon or fragment thereof, wherein the primers do not include a differentially methylated position of the transposon;
  step b) comprises: amplification of the bisulfited DNA with at least one primer pair that is specific for the transposon or fragment thereof, and that includes at least one primer comprising at least one differentially methylated position of the transposon; and
  step c) comprises: determination of the normalized DNA methylation level via the ratio of the amplificates formed in steps a) and b).

E5. The process according to embodiment E4, wherein both primers of the primer pair in step b) include at least one differentially methylated position of the transposon.

E6. The process according to embodiment E4, wherein the primer in step b) includes 2, 3 or 4 differentially methylated positions of the transposon.

E7. The process according to embodiment E4, wherein the primer has a differentially methylated position of the transposon at its 3' end.

E8. The process according to embodiment E4, wherein said at least one primer in step b) includes an oligonucleotide selected from the group consisting of SEQ ID Nos. 3 to 1048.

E9. The process according to embodiment E4, wherein said amplification in steps a) and b) is performed by means of real time PCR.

E10. A process for determining the relative DNA methylation level, comprising the steps:
- d) determination of the methylation level according to steps a) to c) according to claim 1 for a first DNA and a second DNA; and
- e) determination of the relative DNA methylation level via the ratio of the methylation levels determined for the first and second DNAs.

E11. The process according to embodiment E10 for the diagnosis of a disease related to an altered DNA methylation, wherein said first DNA is a reference sample and said second DNA originates from a sample to be examined.

E12. The process according to embodiment E11, wherein said disease is a tumor.

E13. An oligonucleotide selected from the group consisting of SEQ ID No. 3 to SEQ ID No. 1415, preferably SEQ ID No. 3 to SEQ ID No. 436 and/or SEQ ID Nos. 1049 to 1227.

E14. Use of at least one oligonucleotide according to embodiment E13 for determining the normalized and/or relative DNA methylation level.

SEQUENCE LISTING

```
<160> NUMBER OF SEQ ID NOS: 1422

<210> SEQ ID NO 1
<211> LENGTH: 420
<212> TYPE: DNA
<213> ORGANISM: Artificial
<220> FEATURE:
<223> OTHER INFORMATION: Promoter range of the LINE-1 element with
      complete methylation of this promoter sequence and subsequent
      bisulfitation

<400> SEQUENCE: 1 gggggagga gttaagatgg tcgaatagga atagtttcgg tttatagttt ttagcgtgag     60
cgacgtagaa gacggtgatt tttgtatttt tatttgaggt atcgggttta ttttattagg    120
gagtgttaga tagtgggcgt aggttagtgt gtgtgcgtat cgtgcgcgag tcgaagtagg    180
gcgaggtatt gttttatttg ggaagcgtaa ggggttaggg agtttttttt ttgagttaaa    240 gaaagggtg acggtcgtat ttggaaaatc gggttatttt tattcgaata ttgcgttttt    300
tagatcggtt taagaaacgg cgtattacga gattatattt tatatttggt tcggagggtt    360
ttacgtttac ggaatttcgt tgattgttag tatagtagtt tgagattaaa ttgtaaggcg    420

<210> SEQ ID NO 2
<211> LENGTH: 420
<212> TYPE: DNA
<213> ORGANISM: Artificial
<220> FEATURE:
<223> OTHER INFORMATION: Promoter range of the LINE-1 element with
      complete demethylation of this promoter sequence and subsequent
      bisulfitation

<400> SEQUENCE: 2 gggggagga gttaagatgg ttgaatagga atagttttgg tttatagttt ttagtgtgag     60
tgatgtagaa gatggtgatt tttgtatttt tatttgaggt attgggttta ttttattagg    120
gagtgttaga tagtgggtgt aggttagtgt gtgtgtgtat tgtgtgtgag ttgaagtagg    180
gtgaggtatt gttttatttg ggaagtgtaa ggggttaggg agtttttttt ttgagttaaa    240 gaaagggtg atggttgtat ttggaaaatt gggttatttt tatttgaata ttgtgttttt    300
tagattggtt taagaaatgg tgtattatga gattatattt tatatttggt ttggagggtt    360
ttatgtttat ggaatttgt tgattgttag tatagtagtt tgagattaaa ttgtaaggtg     420

<210> SEQ ID NO 3
<211> LENGTH: 20
<212> TYPE: DNA
```

```
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 3
ggggaggagt taagatggtc                                              20

<210> SEQ ID NO 4
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 4
ggtcgaatag gaatagtttc                                              20

<210> SEQ ID NO 5
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 5
ttcggtttat agtttttagc                                              20

<210> SEQ ID NO 6
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 6
ttatagtttt tagcgtgagc                                              20

<210> SEQ ID NO 7
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 7
tagtttttag cgtgagcgac                                              20

<210> SEQ ID NO 8
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 8
gcgtgagcga cgtagaagac                                              20
```

<210> SEQ ID NO 9
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 9
gtatttttat ttgaggtatc                                              20

<210> SEQ ID NO 10
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 10
gggagtgtta gatagtgggc                                              20

<210> SEQ ID NO 11
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 11
gcgtaggtta gtgtgtgtgc                                              20

<210> SEQ ID NO 12
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 12
ggttagtgtg tgtgcgtatc                                              20

<210> SEQ ID NO 13
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 13
agtgtgtgtg cgtatcgtgc                                              20

<210> SEQ ID NO 14
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region -continued of the LINE-1 element

<400> SEQUENCE: 14
tgtgtgtgcg tatcgtgcgc                                        20

<210> SEQ ID NO 15
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 15
gtgcgtatcg tgcgcgagtc                                        20

<210> SEQ ID NO 16
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 16
tgcgcgagtc gaagtagggc                                        20

<210> SEQ ID NO 17
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 17
tattgtttta tttgggaagc                                        20

<210> SEQ ID NO 18
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 18
gagttaaaga aaggggtgac                                        20

<210> SEQ ID NO 19
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 19
taaagaaagg ggtgacggtc                                        20

<210> SEQ ID NO 20
<211> LENGTH: 20

-continued

```
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 20
acggtcgtat ttggaaaatc                                                20

<210> SEQ ID NO 21
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 21
aaatcgggtt atttttattc                                                20

<210> SEQ ID NO 22
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 22 tattttatt cgaatattgc                                                 20

<210> SEQ ID NO 23
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 23
aatattgcgt tttttagatc                                                20

<210> SEQ ID NO 24
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 24
tttagatcgg tttaagaaac                                                20

<210> SEQ ID NO 25
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 25
```

-continued

```
agatcggttt aagaaacggc                                               20

<210> SEQ ID NO 26
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 26
tttaagaaac ggcgtattac                                               20

<210> SEQ ID NO 27
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 27
ttatatttta tatttggttc                                               20

<210> SEQ ID NO 28
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 28
tttggttcgg agggttttac                                               20

<210> SEQ ID NO 29
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 29
tcggagggtt ttacgtttac                                               20

<210> SEQ ID NO 30
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 30
ttttacgttt acggaatttc                                               20

<210> SEQ ID NO 31
<211> LENGTH: 20
<212> TYPE: DNA
<213> ORGANISM: Artificial
<220> FEATURE:
<223> OTHER INFORMATION: SEQUENCE-IDENTICAL primer specific for the
``` bisulfite-converted METHYLATED SENSE strand of the promoter region of the LINE-1 element

<400> SEQUENCE: 31
ttgagattaa attgtaaggc                                                20

<210> SEQ ID NO 32
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 32
ttaaattgta aggcggtaac                                                20

<210> SEQ ID NO 33
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 33
aacgaggttg ggggaggggc                                                20

<210> SEQ ID NO 34
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 34
aggttggggg aggggcgttc                                                20

<210> SEQ ID NO 35
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 35
tttaggtaaa taaagtagtc                                                20

<210> SEQ ID NO 36
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 36
ataaagtagt cgggaagttc                                                20

<210> SEQ ID NO 37

```
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 37
agtagtggtt tttttagtac                                               20

<210> SEQ ID NO 38
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 38
gtagttggag atttgagaac                                               20

<210> SEQ ID NO 39
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 39
gtttttgatt tttgattttc                                               20

<210> SEQ ID NO 40
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 40
ggtatattga tattttatac                                               20

<210> SEQ ID NO 41
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 41
ttagaaagga tatttatatc                                               20

<210> SEQ ID NO 42
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 42
```

```
aaaattggaa attttaaaac                                                   20

<210> SEQ ID NO 43
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 43
gaaattttaa aacgtagagc                                                   20

<210> SEQ ID NO 44
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 44
tttttttttt ttaaaggaac                                                   20

<210> SEQ ID NO 45
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 45
ggatggagaa tgattttgac                                                   20

<210> SEQ ID NO 46
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 46
gagagaagaa ggttttagac                                                   20

<210> SEQ ID NO 47
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 47
attaaattat tttgagttac                                                   20

<210> SEQ ID NO 48
<211> LENGTH: 20
<212> TYPE: DNA
<213> ORGANISM: Artificial
<220> FEATURE:
```

<223> OTHER INFORMATION: SEQUENCE-IDENTICAL primer specific for the
      bisulfite-converted METHYLATED SENSE strand of the promoter region
      of the LINE-1 element

<400> SEQUENCE: 48
ggagttgaaa attaaggttc                                                    20

<210> SEQ ID NO 49
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 49
aattaaggtt cgagaattac                                                    20

<210> SEQ ID NO 50
<211> LENGTH: 19
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 50
tgtagaagtt ttaggagtc                                                     19

<210> SEQ ID NO 51
<211> LENGTH: 19
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 51
gaagttttag gagtcgatg                                                     19

<210> SEQ ID NO 52
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 52
tgaaatgaat gaaatgaagc                                                    20

<210> SEQ ID NO 53
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 53
tgtgaaaaga ttaaatttac                                                    20

-continued

```
<210> SEQ ID NO 54
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 54
atttagtaag gtaggttaac                                              20

<210> SEQ ID NO 55
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 55
atttaggaaa tatagagaac                                              20

<210> SEQ ID NO 56
<211> LENGTH: 18
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 56
gttataaaga tatttttc                                                18

<210> SEQ ID NO 57
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 57
ggtagttaga gagaaaggtc                                              20

<210> SEQ ID NO 58
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 58
ggggaggagt taagatggtt                                              20

<210> SEQ ID NO 59
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element
```

<400> SEQUENCE: 59
ggttgaatag gaatagtttt                                          20

<210> SEQ ID NO 60
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 60
tttggtttat agtttttagt                                          20

<210> SEQ ID NO 61
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 61
ttatagtttt tagtgtgagt                                          20

<210> SEQ ID NO 62
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 62 tagttttag tgtgagtgat                                           20

<210> SEQ ID NO 63
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 63
gtgtgagtga tgtagaagat                                          20

<210> SEQ ID NO 64
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 64
gtatttttat ttgaggtatt                                          20

<210> SEQ ID NO 65
<211> LENGTH: 20
<212> TYPE: DNA
<213> ORGANISM: Artificial

-continued

```
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 65
gggagtgtta gatagtgggt                                              20

<210> SEQ ID NO 66
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 66
gtgtaggtta gtgtgtgtgt                                              20

<210> SEQ ID NO 67
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 67
ggttagtgtg tgtgtgtatt                                              20

<210> SEQ ID NO 68
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 68
agtgtgtgtg tgtattgtgt                                              20

<210> SEQ ID NO 69
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 69
tgtgtgtgtg tattgtgtgt                                              20

<210> SEQ ID NO 70
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 70
gtgtgtattg tgtgtgagtt                                              20
```

```
<210> SEQ ID NO 71
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 71
tgtgtgagtt gaagtagggt                                              20

<210> SEQ ID NO 72
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 72
tattgtttta tttgggaagt                                              20

<210> SEQ ID NO 73
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 73
gagttaaaga aagggtgat                                               20

<210> SEQ ID NO 74
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 74
taaagaaagg ggtgatggtt                                              20

<210> SEQ ID NO 75
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 75
atggttgtat ttggaaaatt                                              20

<210> SEQ ID NO 76
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element
```

```
<400> SEQUENCE: 76
aaattgggtt atttttattt                                              20

<210> SEQ ID NO 77
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 77
tatttttatt tgaatattgt                                              20

<210> SEQ ID NO 78
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 78
aatattgtgt ttttagatt                                               20

<210> SEQ ID NO 79
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 79
tttagattgg tttaagaaat                                              20

<210> SEQ ID NO 80
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 80
agattggttt aagaaatggt                                              20

<210> SEQ ID NO 81
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 81
tttaagaaat ggtgtattat                                              20

<210> SEQ ID NO 82
<211> LENGTH: 20
<212> TYPE: DNA
```

```
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 82
ttatatttta tatttggttt                                               20

<210> SEQ ID NO 83
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 83
tttggtttgg agggttttat                                               20

<210> SEQ ID NO 84
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 84
ttggagggtt ttatgtttat                                               20

<210> SEQ ID NO 85
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 85
ttttatgttt atggaatttt                                               20

<210> SEQ ID NO 86
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 86
ttgagattaa attgtaaggt                                               20

<210> SEQ ID NO 87
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 87
ttaaattgta aggtggtaat                                               20
```

<210> SEQ ID NO 88
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 88
aatgaggttg ggggaggggt                                              20

<210> SEQ ID NO 89
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 89
aggttggggg agggtgttt                                               20

<210> SEQ ID NO 90
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 90
tttaggtaaa taaagtagtt                                              20

<210> SEQ ID NO 91
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 91
ataaagtagt tgggaagttt                                              20

<210> SEQ ID NO 92
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 92
agtagtggtt ttttagtat                                               20

<210> SEQ ID NO 93
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter region of the LINE-1 element

<400> SEQUENCE: 93
gtagttggag atttgagaat                                      20

<210> SEQ ID NO 94
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 94
gtttttgatt tttgattttt                                      20

<210> SEQ ID NO 95
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 95
ggtatattga tattttatat                                      20

<210> SEQ ID NO 96
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 96
ttagaaagga tatttatatt                                      20

<210> SEQ ID NO 97
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 97
aaaattggaa attttaaaat                                      20

<210> SEQ ID NO 98
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 98
gaaattttaa aatgtagagt                                      20

<210> SEQ ID NO 99
<211> LENGTH: 20

```
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 99
tttttttttt ttaaaggaat                                              20

<210> SEQ ID NO 100
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 100
ggatggagaa tgattttgat                                              20

<210> SEQ ID NO 101
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 101
gagagaagaa ggttttagat                                              20

<210> SEQ ID NO 102
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 102
attaaattat tttgagttat                                              20

<210> SEQ ID NO 103
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 103
ggagttgaaa attaaggttt                                              20

<210> SEQ ID NO 104
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 104
```

```
aattaaggtt tgagaattat                                              20

<210> SEQ ID NO 105
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 105
atgtagaagt tttaggagtt                                              20

<210> SEQ ID NO 106
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 106
gaagttttag gagttgatgt                                              20

<210> SEQ ID NO 107
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 107
tgaaatgaat gaaatgaagt                                              20

<210> SEQ ID NO 108
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 108
tgtgaaaaga ttaaatttat                                              20

<210> SEQ ID NO 109
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 109
atttagtaag gtaggttaat                                              20

<210> SEQ ID NO 110
<211> LENGTH: 20
<212> TYPE: DNA
<213> ORGANISM: Artificial
<220> FEATURE:
<223> OTHER INFORMATION: SEQUENCE-IDENTICAL primer specific for the
``` bisulfite-converted DEMETHYLATED SENSE strand of the promoter
      region of the LINE-1 element

<400> SEQUENCE: 110
atttaggaaa tatagagaat                                              20

<210> SEQ ID NO 111
<211> LENGTH: 18
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 111
gttataaaga tatttttt                                                18

<210> SEQ ID NO 112
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the promoter
      region of the LINE-1 element

<400> SEQUENCE: 112
ggtagttaga gagaaaggtt                                              20

<210> SEQ ID NO 113
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter
      region of the LINE-1 element

<400> SEQUENCE: 113
tttcctttaa aaataacccg                                              20

<210> SEQ ID NO 114
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 114
tcttaaaatt actcttctcg                                              20

<210> SEQ ID NO 115
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 115
cgaaaaatat ctttataacg                                              20

<210> SEQ ID NO 116

```
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 116
atatttccta aatctaaacg                                              20

<210> SEQ ID NO 117
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 117
tcaaatacac caatcaaacg                                              20

<210> SEQ ID NO 118
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 118
tctctaaact tcccttctcg                                              20

<210> SEQ ID NO 119
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 119
ccctttcttc caattaatcg                                              20

<210> SEQ ID NO 120
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 120
tcttccaatt aatcgcatcg                                              20

<210> SEQ ID NO 121
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 121
```
aaacttctac attcttcacg					20

<210> SEQ ID NO 122
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 122
cattcttcac gtaattctcg					20

<210> SEQ ID NO 123
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 123
ttaatttaaa tatcctcccg					20

<210> SEQ ID NO 124
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 124
aactcaaaat aatttaatcg					20

<210> SEQ ID NO 125
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 125
aaccttcttc tctcaactcg					20

<210> SEQ ID NO 126
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 126
attactaata aaaaactacg					20

<210> SEQ ID NO 127
<211> LENGTH: 20
<212> TYPE: DNA
<213> ORGANISM: Artificial
<220> FEATURE:

<223> OTHER INFORMATION: COMPLEMENTARY primer specific for the
      bisulfite-converted METHYLATED SENSE strand of the promoter region
      of the LINE-1 element

<400> SEQUENCE: 127
cctttaaaaa aaaaaaaacg                                              20

<210> SEQ ID NO 128
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 128
aaaaaaaaaa acgctctacg                                              20

<210> SEQ ID NO 129
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 129
aatatacaaa taaattttcg                                              20

<210> SEQ ID NO 130
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 130
tctattaaaa taccctaccg                                              20

<210> SEQ ID NO 131
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 131
cctcccaatt aaactactcg                                              20

<210> SEQ ID NO 132
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 132
aaaaacaatc tatctacccg                                              20

-continued

```
<210> SEQ ID NO 133
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 133
ttctcaaatc tccaactacg                                              20

<210> SEQ ID NO 134
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 134
aataaactcc acccaattcg                                              20

<210> SEQ ID NO 135
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 135
cacccaattc gaacttcccg                                              20

<210> SEQ ID NO 136
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 136
aacctaaaca ataacgaacg                                              20

<210> SEQ ID NO 137
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 137
acgcccctcc cccaacctcg                                              20

<210> SEQ ID NO 138
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element
```

```
<400> SEQUENCE: 138
ctcccccaac ctcgttaccg                                               20

<210> SEQ ID NO 139
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 139
tactatacta acaatcaacg                                               20

<210> SEQ ID NO 140
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 140
taacaatcaa cgaaattccg                                               20

<210> SEQ ID NO 141
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 141
tcaacgaaat tccgtaaacg                                               20

<210> SEQ ID NO 142
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted
      METHYLATED SENSE strand of the promoter region of the LINE-1
      element

<400> SEQUENCE: 142
cgtaaacgta aaccctccg                                                20

<210> SEQ ID NO 143
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 143
aaatataaaa tataatctcg                                               20

<210> SEQ ID NO 144
<211> LENGTH: 20
<212> TYPE: DNA
```

```
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 144
aaatataatc tcgtaatacg                                            20

<210> SEQ ID NO 145
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 145
tataatctcg taatacgccg                                            20

<210> SEQ ID NO 146
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 146
atacgccgtt tcttaaaccg                                            20

<210> SEQ ID NO 147
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 147
ttaaaccgat ctaaaaaacg                                            20

<210> SEQ ID NO 148
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 148
tctaaaaaac gcaatattcg                                            20

<210> SEQ ID NO 149
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 149
attcgaataa aaataacccg                                            20
```

```
<210> SEQ ID NO 150
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 150
aacccgattt tccaaatacg                                              20

<210> SEQ ID NO 151
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 151
cgattttcca aatacgaccg                                              20

<210> SEQ ID NO 152
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 152
aaactcccta accccttacg                                              20

<210> SEQ ID NO 153
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 153
ccaaataaaa caataccctcg                                             20

<210> SEQ ID NO 154
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 154
caatacctcg ccctacttcg                                              20

<210> SEQ ID NO 155
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
```

```
                       of the LINE-1 element

<400> SEQUENCE: 155
cctcgcccta cttcgactcg                                                 20

<210> SEQ ID NO 156
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 156
tcgccctact tcgactcgcg                                                 20

<210> SEQ ID NO 157
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 157
cctacttcga ctcgcgcacg                                                 20

<210> SEQ ID NO 158
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 158
ttcgactcgc gcacgatacg                                                 20

<210> SEQ ID NO 159
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 159
cgcacacaca ctaacctacg                                                 20

<210> SEQ ID NO 160
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 160
tccctaataa aataaacccg                                                 20

<210> SEQ ID NO 161
<211> LENGTH: 20
```

```
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 161
taaaaataca aaaatcaccg                                          20

<210> SEQ ID NO 162
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 162
aaaaatcacc gtcttctacg                                          20

<210> SEQ ID NO 163
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 163
aatcaccgtc ttctacgtcg                                          20

<210> SEQ ID NO 164
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 164
cgtcttctac gtcgctcacg                                          20

<210> SEQ ID NO 165
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 165
acgctaaaaa ctataaaccg                                          20

<210> SEQ ID NO 166
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter region
      of the LINE-1 element

<400> SEQUENCE: 166
```

```
accgaaacta ttcctattcg                                               20

<210> SEQ ID NO 167
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 167
tttcctttaa aaataaccca                                               20

<210> SEQ ID NO 168
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 168
tcttaaaatt actcttctca                                               20

<210> SEQ ID NO 169
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 169
caaaaaatat ctttataaca                                               20

<210> SEQ ID NO 170
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 170
atatttccta aatctaaaca                                               20

<210> SEQ ID NO 171
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 171
tcaaatacac caatcaaaca                                               20

<210> SEQ ID NO 172
<211> LENGTH: 20
<212> TYPE: DNA
<213> ORGANISM: Artificial
<220> FEATURE:
<223> OTHER INFORMATION: COMPLEMENTARY primer specific for the
``` bisulfite-converted DEMETHYLATED SENSE strand of the promoter
region of the LINE-1 element

<400> SEQUENCE: 172
tctctaaact tcccttctca                                          20

<210> SEQ ID NO 173
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 173
ccctttcttc caattaatca                                          20

<210> SEQ ID NO 174
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 174
tcttccaatt aatcacatca                                          20

<210> SEQ ID NO 175
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 175
aaacttctac attcttcaca                                          20

<210> SEQ ID NO 176
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 176
cattcttcac ataattctca                                          20

<210> SEQ ID NO 177
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 177
ttaatttaaa tatcctccca                                          20

<210> SEQ ID NO 178

```
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 178
aactcaaaat aatttaatca                                              20

<210> SEQ ID NO 179
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 179
aaccttcttc tctcaactca                                              20

<210> SEQ ID NO 180
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 180
aaccttcttc tctcaactca                                              20

<210> SEQ ID NO 181
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 181
cctttaaaaa aaaaaaaaca                                              20

<210> SEQ ID NO 182
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 182
aaaaaaaaaa acactctaca                                              20

<210> SEQ ID NO 183
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 183
```

-continued aatatacaaa taaattttca                                          20

<210> SEQ ID NO 184
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 184
tctattaaaa taccctacca                                          20

<210> SEQ ID NO 185
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 185
cctcccaatt aaactactca                                          20

<210> SEQ ID NO 186
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 186
aaaaacaatc tatctaccca                                          20

<210> SEQ ID NO 187
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the promoter
      region of the LINE-1 element

<400> SEQUENCE: 187
ttctcaaatc tccaactaca                                          20

<210> SEQ ID NO 188
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 188
aataaactcc acccaattca                                          20

<210> SEQ ID NO 189
<211> LENGTH: 20
<212> TYPE: DNA
<213> ORGANISM: Artificial
<220> FEATURE:

```
<223> OTHER INFORMATION: COMPLEMENTARY primer specific for the
      bisulfite-converted DEMETHYLATED SENSE strand of the promoter
      region of the LINE-1 element

<400> SEQUENCE: 189
cacccaattc aaacttccca                                                    20

<210> SEQ ID NO 190
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 190
aacctaaaca ataacaaaca                                                    20

<210> SEQ ID NO 191
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 191
acacccctcc cccaacctca                                                    20

<210> SEQ ID NO 192
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 192
ctcccccaac ctcattacca                                                    20

<210> SEQ ID NO 193
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 193
tactatacta acaatcaaca                                                    20

<210> SEQ ID NO 194
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 194
taacaatcaa caaaattcca                                                    20
```

```
<210> SEQ ID NO 195
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 195
tcaacaaaat tccataaaca                                              20

<210> SEQ ID NO 196
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 196
cataaacata aaccctcca                                               20

<210> SEQ ID NO 197
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 197
aaatataaaa tataatctca                                              20

<210> SEQ ID NO 198
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 198
aaatataatc tcataataca                                              20

<210> SEQ ID NO 199
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 199
tataatctca taatacacca                                              20

<210> SEQ ID NO 200
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element
```

<400> SEQUENCE: 200
atacaccatt tcttaaacca                                              20

<210> SEQ ID NO 201
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 201
ttaaaccaat ctaaaaaaca                                              20

<210> SEQ ID NO 202
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 202
tctaaaaaac acaatattca                                              20

<210> SEQ ID NO 203
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 203
attcaaataa aaataaccca                                              20

<210> SEQ ID NO 204
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 204
aacccaattt tccaaataca                                              20

<210> SEQ ID NO 205
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 205
caattttcca aatacaacca                                              20

<210> SEQ ID NO 206
<211> LENGTH: 20
<212> TYPE: DNA
<213> ORGANISM: Artificial

```
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 206
aaactcccta accccttaca                                                  20

<210> SEQ ID NO 207
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 207
ccaaataaaa caatacctca                                                  20

<210> SEQ ID NO 208
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 208
caatacctca ccctacttca                                                  20

<210> SEQ ID NO 209
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 209
cctcacccta cttcaactca                                                  20

<210> SEQ ID NO 210
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 210
tcaccctact tcaactcaca                                                  20

<210> SEQ ID NO 211
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 211
cctacttcaa ctcacacaca                                                  20
```

<210> SEQ ID NO 212
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 212
ttcaactcac acacaataca                                                      20

<210> SEQ ID NO 213
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 213
cacacacaca ctaacctaca                                                      20

<210> SEQ ID NO 214
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 214
tccctaataa aataaaccca                                                      20

<210> SEQ ID NO 215
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 215
taaaaataca aaaatcacca                                                      20

<210> SEQ ID NO 216
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 216
aaaaatcacc atcttctaca                                                      20

<210> SEQ ID NO 217
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 217
aatcaccatc ttctacatca                                                    20

<210> SEQ ID NO 218
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 218
catcttctac atcactcaca                                                    20

<210> SEQ ID NO 219
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 219
acactaaaaa ctataaacca                                                    20

<210> SEQ ID NO 220
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the promoter
      region of the LINE-1 element

<400> SEQUENCE: 220
accaaaacta ttcctattca                                                    20

<210> SEQ ID NO 221
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter
      region of the LINE-1 element

<400> SEQUENCE: 221
tgtagttttt ttttagtttc                                                    20

<210> SEQ ID NO 222
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 222
ttttggtatg attttgtagc                                                    20

<210> SEQ ID NO 223
<211> LENGTH: 20
<212> TYPE: DNA

<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 223
attttgtagc ggttggtatc                                           20

<210> SEQ ID NO 224
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 224
tggtttgtag ggttttttgtc                                          20

<210> SEQ ID NO 225
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 225
tttttttttg agggtaattc                                           20

<210> SEQ ID NO 226
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 226
gttttggagt tgttttttttc                                          20

<210> SEQ ID NO 227
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 227
tgtatttttt gaatttgaac                                           20

<210> SEQ ID NO 228
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 228
tttaggtata ttaattagac                                           20

<210> SEQ ID NO 229
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 229 tttttttaaat ttttttttc                                              20

<210> SEQ ID NO 230
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 230 atttttttt ttagttgatc                                               20

<210> SEQ ID NO 231
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 231 ttttttagt tgatcgtatc                                               20

<210> SEQ ID NO 232
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 232 gaggttttg tattttttac                                               20

<210> SEQ ID NO 233
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 233
gtatttttta cgtagttttc                                              20

<210> SEQ ID NO 234
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region of the LINE-1 element

<400> SEQUENCE: 234
tttggtttga atgtttttc                                                    20

<210> SEQ ID NO 235
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 235
tagtttagag taatttgatc                                                   20

<210> SEQ ID NO 236
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 236
aagttttttt ttttagttc                                                    20

<210> SEQ ID NO 237
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 237
tgttgttggt gaggaattgc                                                   20

<210> SEQ ID NO 238
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 238 tttttttggag gaggagaggc                                                  20

<210> SEQ ID NO 239
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 239
gaggaggaga ggcgttttgc                                                   20

<210> SEQ ID NO 240
<211> LENGTH: 20

```
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 240
tgatgtatag atgggttttc                                              20

<210> SEQ ID NO 241
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 241
gtttgttgga atattttgtc                                              20

<210> SEQ ID NO 242
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 242 gtttttagt taggttgttc                                               20

<210> SEQ ID NO 243
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 243
aggaggtagt ttgtttgttc                                              20

<210> SEQ ID NO 244
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 244
gtttttagat ttttagttgc                                              20

<210> SEQ ID NO 245
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 245
```
tggtgggttt tatttagttc    20

<210> SEQ ID NO 246
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 246
ttatttagtt cgagttttc    20

<210> SEQ ID NO 247
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 247
aagtaagttt gggtaatggc    20

<210> SEQ ID NO 248
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 248
aagtttgggt aatggcgggc    20

<210> SEQ ID NO 249
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 249
ggcgtttttt ttttagtttc    20

<210> SEQ ID NO 250
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 250 tttttttag tttcgttgtc    20

<210> SEQ ID NO 251
<211> LENGTH: 20
<212> TYPE: DNA
<213> ORGANISM: Artificial
<220> FEATURE:
<223> OTHER INFORMATION: SEQUENCE-IDENTICAL primer specific for the -continued bisulfite-converted METHYLATED SENSE strand of the promoter region
of the LINE-1 element

<400> SEQUENCE: 251
ttgttgtgtt agtaattagc                                                 20

<210> SEQ ID NO 252
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 252
ttagtaatta gcgagatttc                                                 20

<210> SEQ ID NO 253
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 253
attagcgaga tttcgtgggc                                                 20

<210> SEQ ID NO 254
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 254
tcgtgggcgt aggattttc                                                  20

<210> SEQ ID NO 255
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the promoter
      region of the LINE-1 element

<400> SEQUENCE: 255
taggtgtggg atatagtttc                                                 20

<210> SEQ ID NO 256
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 256
gggatatagt ttcgtggtgc                                                 20

<210> SEQ ID NO 257

-continued

```
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 257
atatagtttc gtggtgcgtc                                                  20

<210> SEQ ID NO 258
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 258
ggtgcgtcgt tttttaagtc                                                  20

<210> SEQ ID NO 259
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 259
tttaagtcgg tttgaaaagc                                                  20

<210> SEQ ID NO 260
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 260
gtttgaaaag cgtaatattc                                                  20

<210> SEQ ID NO 261
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 261
tattcgggtg ggagtgattc                                                  20

<210> SEQ ID NO 262
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 262
```
tgattcgatt ttttaggtgc                                              20

<210> SEQ ID NO 263
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 263
tcgatttttt aggtgcgatc                                              20

<210> SEQ ID NO 264
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 264
ggaatttttt gatttttttgc                                             20

<210> SEQ ID NO 265
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 265
tttaggtgag gtaatgtttc                                              20

<210> SEQ ID NO 266
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 266
gtaatgtttc gttttgtttc                                              20

<210> SEQ ID NO 267
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 267
gtttcgtttt gtttcggttc                                              20

<210> SEQ ID NO 268
<211> LENGTH: 20
<212> TYPE: DNA
<213> ORGANISM: Artificial
<220> FEATURE:

<223> OTHER INFORMATION: SEQUENCE-IDENTICAL primer specific for the
      bisulfite-converted METHYLATED SENSE strand of the promoter region
      of the LINE-1 element

<400> SEQUENCE: 268
ttcgttttgt ttcggttcgc                                           20

<210> SEQ ID NO 269
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 269
ttttgtttcg gttcgcgtac                                           20

<210> SEQ ID NO 270
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 270
tttcggttcg cgtacggtgc                                           20

<210> SEQ ID NO 271
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 271
gcgtatatat attggtttgc                                           20

<210> SEQ ID NO 272
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 272 tttttttagtg agatgaattc                                          20

<210> SEQ ID NO 273
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 273
atggaaatgt agaaattatc                                           20

```
<210> SEQ ID NO 274
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 274
tagaaattat cgttttttgc                                                  20

<210> SEQ ID NO 275
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 275
aaattatcgt ttttgcgtc                                                   20

<210> SEQ ID NO 276
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 276 tcgtttttg cgtcgtttac                                                   20

<210> SEQ ID NO 277
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 277
tacgttggga gttgtagatc                                                  20

<210> SEQ ID NO 278
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the promoter region
      of the LINE-1 element

<400> SEQUENCE: 278
gatcggagtt gttttattc                                                   20

<210> SEQ ID NO 279
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element
```

<400> SEQUENCE: 279
tgtagttttt ttttagtttt                          20

<210> SEQ ID NO 280
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 280
ttttggtatg attttgtagt                          20

<210> SEQ ID NO 281
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 281
attttgtagt ggttggtatt                          20

<210> SEQ ID NO 282
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 282
tggtttgtag ggttttttgtt                         20

<210> SEQ ID NO 283
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 283
tttttttttg agggtaattt                          20

<210> SEQ ID NO 284
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 284
gttttggagt tgttttttttt                         20

<210> SEQ ID NO 285
<211> LENGTH: 20
<212> TYPE: DNA
<213> ORGANISM: Artificial

```
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 285 tgtattttt gaatttgaat                                            20

<210> SEQ ID NO 286
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 286
tttaggtata ttaattagat                                           20

<210> SEQ ID NO 287
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 287 tttttaaat tttttttttt                                            20

<210> SEQ ID NO 288
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 288 atttttttt ttagttgatt                                            20

<210> SEQ ID NO 289
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 289
tttttttagt tgattgtatt                                           20

<210> SEQ ID NO 290
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 290 gaggttttg tatttttat                                             20
```

<210> SEQ ID NO 291
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 291 gtattttta tgtagttttt                                                  20

<210> SEQ ID NO 292
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 292
tttggtttga atgtttttt                                                  20

<210> SEQ ID NO 293
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 293
tagtttagag taatttgatt                                                 20

<210> SEQ ID NO 294
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 294
aagttttttt tttttagttt                                                 20

<210> SEQ ID NO 295
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 295
tgttgttggt gaggaattgt                                                 20

<210> SEQ ID NO 296
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

```
<400> SEQUENCE: 296 tttttttggag gaggagaggt                                               20

<210> SEQ ID NO 297
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 297
gaggaggaga ggtgttttgt                                                20

<210> SEQ ID NO 298
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 298
tgatgtatag atgggttttt                                                20

<210> SEQ ID NO 299
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 299
gtttgttgga atattttgtt                                                20

<210> SEQ ID NO 300
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 300 gtttttagt taggttgttt                                                 20

<210> SEQ ID NO 301
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 301
aggaggtagt ttgtttgttt                                                20

<210> SEQ ID NO 302
<211> LENGTH: 20
<212> TYPE: DNA
```

```
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 302
gtttttagat ttttagttgt                                              20

<210> SEQ ID NO 303
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 303
tggtgggttt tatttagttt                                              20

<210> SEQ ID NO 304
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 304
ttatttagtt tgagtttttt                                              20

<210> SEQ ID NO 305
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 305
aagtaagttt gggtaatggt                                              20

<210> SEQ ID NO 306
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 306
aagtttgggt aatggtgggt                                              20

<210> SEQ ID NO 307
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 307
ggtgtttttt ttttagtttt                                              20
```

<210> SEQ ID NO 308
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 308 tttttttttag ttttgttgtt                                              20

<210> SEQ ID NO 309
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 309
ttgttgtgtt agtaattagt                                               20

<210> SEQ ID NO 310
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 310
ttagtaatta gtgagattt                                                20

<210> SEQ ID NO 311
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 311
attagtgaga ttttgtgggt                                               20

<210> SEQ ID NO 312
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 312
ttgtgggtgt aggatttttt                                               20

<210> SEQ ID NO 313
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter region of the LINE-1 element

<400> SEQUENCE: 313
taggtgtggg atatagtttt                                            20

<210> SEQ ID NO 314
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 314
gggatatagt tttgtggtgt                                            20

<210> SEQ ID NO 315
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 315
atatagtttt gtggtgtgtt                                            20

<210> SEQ ID NO 316
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 316
ggtgtgttgt tttttaagtt                                            20

<210> SEQ ID NO 317
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 317
tttaagttgg tttgaaaagt                                            20

<210> SEQ ID NO 318
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 318
gtttgaaaag tgtaatattt                                            20

<210> SEQ ID NO 319
<211> LENGTH: 20

```
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 319
tatttgggtg ggagtgattt                                              20

<210> SEQ ID NO 320
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 320
tgatttgatt ttttaggtgt                                              20

<210> SEQ ID NO 321
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 321
ttgatttttt aggtgtgatt                                              20

<210> SEQ ID NO 322
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 322
ggaatttttt gattttttgt                                              20

<210> SEQ ID NO 323
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 323
tttaggtgag gtaatgtttt                                              20

<210> SEQ ID NO 324
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 324
```

```
gtaatgtttt gttttgtttt                                          20

<210> SEQ ID NO 325
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 325
gttttgtttt gttttggttt                                          20

<210> SEQ ID NO 326
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 326
tttgttttgt tttggtttgt                                          20

<210> SEQ ID NO 327
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 327
ttttgttttg gtttgtgtat                                          20

<210> SEQ ID NO 328
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 328
ttttggtttg tgtatggtgt                                          20

<210> SEQ ID NO 329
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 329
gtgtatatat attggtttgt                                          20

<210> SEQ ID NO 330
<211> LENGTH: 20
<212> TYPE: DNA
<213> ORGANISM: Artificial
<220> FEATURE:
<223> OTHER INFORMATION: SEQUENCE-IDENTICAL primer specific for the
``` bisulfite-converted DEMETHYLATED ANTISENSE strand of the promoter region of the LINE-1 element

<400> SEQUENCE: 330 tttttttagtg agatgaattt                                           20

<210> SEQ ID NO 331
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 331
atggaaatgt agaaattatt                                            20

<210> SEQ ID NO 332
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 332
tagaaattat tgttttttgt                                            20

<210> SEQ ID NO 333
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 333
aaattattgt ttttgtgtt                                             20

<210> SEQ ID NO 334
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 334
ttgttttttg tgttgtttat                                            20

<210> SEQ ID NO 335
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 335
tatgttggga gttgtagatt                                            20

<210> SEQ ID NO 336

```
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the promoter
      region of the LINE-1 element

<400> SEQUENCE: 336
gattggagtt gttttttattt                                              20

<210> SEQ ID NO 337
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 337
aaaaaaaaac caaaataacc g                                             21

<210> SEQ ID NO 338
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 338
aaccgaataa aaacaactcc g                                             21

<210> SEQ ID NO 339
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 339
tccgatctac aactcccaac g                                             21

<210> SEQ ID NO 340
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 340
ctacaactcc caacgtaaac g                                             21

<210> SEQ ID NO 341
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 341
```

```
caactcccaa cgtaaacgac g                                              21
```

<210> SEQ ID NO 342
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 342

```
acgtaaacga cgcaaaaaac g                                              21
```

<210> SEQ ID NO 343
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 343

```
acatttccat ctaaaatacc g                                              21
```

<210> SEQ ID NO 344
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 344

```
aaaaatacca aacaataaac g                                              21
```

<210> SEQ ID NO 345
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 345

```
acgcaaacca atatatatac g                                              21
```

<210> SEQ ID NO 346
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 346

```
aaccaatata tatacgcacc g                                              21
```

<210> SEQ ID NO 347
<211> LENGTH: 21
<212> TYPE: DNA
<213> ORGANISM: Artificial
<220> FEATURE:

-continued

```
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 347
aatatatata cgcaccgtac g                                              21

<210> SEQ ID NO 348
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 348
tatatatacg caccgtacgc g                                              21

<210> SEQ ID NO 349
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 349
atacgcaccg tacgcgaacc g                                              21

<210> SEQ ID NO 350
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 350
tacgcgaacc gaaacaaaac g                                              21

<210> SEQ ID NO 351
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 351
cattacctca cctaaaaaac g                                              21

<210> SEQ ID NO 352
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 352
aaatcaaaaa aaaaaataac g                                              21
```

<210> SEQ ID NO 353
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 353
caaaaaaaaa aataacgatc g                                         21

<210> SEQ ID NO 354
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 354
acgatcgcac ctaaaaaatc g                                         21

<210> SEQ ID NO 355
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 355
aaatcgaatc actcccaccc g                                         21

<210> SEQ ID NO 356
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 356
cactcccacc cgaatattac g                                         21

<210> SEQ ID NO 357
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 357
aatattacgc ttttcaaacc g                                         21

<210> SEQ ID NO 358
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

```
<400> SEQUENCE: 358
ttcaaaccga cttaaaaaac g                                        21

<210> SEQ ID NO 359
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 359
aaaccgactt aaaaaacgac g                                        21

<210> SEQ ID NO 360
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 360
cttaaaaaac gacgcaccac g                                        21

<210> SEQ ID NO 361
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 361
ctatatccca cacctaactc g                                        21

<210> SEQ ID NO 362
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 362
cctaactcga aaatcctac g                                         21

<210> SEQ ID NO 363
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 363
tcgaaaaatc ctacgcccac g                                        21

<210> SEQ ID NO 364
<211> LENGTH: 21
<212> TYPE: DNA
<213> ORGANISM: Artificial
```

```
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 364
tcctacgccc acgaaatctc g                                              21

<210> SEQ ID NO 365
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 365
ctaaaatcaa actacaaaac g                                              21

<210> SEQ ID NO 366
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 366
tcaaactaca aaacgacaac g                                              21

<210> SEQ ID NO 367
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 367
aacgaaacta aaaaaaaaac g                                              21

<210> SEQ ID NO 368
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 368
aaactaaaaa aaaaacgccc g                                              21

<210> SEQ ID NO 369
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 369
cttaaataaa caaacaacc g                                               21
```

<210> SEQ ID NO 370
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 370
acaaaacaac cgaaaaactc g                                             21

<210> SEQ ID NO 371
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 371
aacaataatt ctcccaacac g                                             21

<210> SEQ ID NO 372
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 372
gcaactaaaa atctaaaaac g                                             21

<210> SEQ ID NO 373
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 373
atccctaact cctaaccccc g                                             21

<210> SEQ ID NO 374
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 374
aacacactaa cacctcacac g                                             21

<210> SEQ ID NO 375
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element -continued

<400> SEQUENCE: 375
ccaaaaaaaa catctacacc g                                              21

<210> SEQ ID NO 376
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 376
aaaactaaaa actctaaaac g                                              21

<210> SEQ ID NO 377
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 377
aaaactctaa aacgcaaaac g                                              21

<210> SEQ ID NO 378
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 378
ctctcctcct ccaaaaaaac g                                              21

<210> SEQ ID NO 379
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 379
aaataaaaaa taattttaac g                                              21

<210> SEQ ID NO 380
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 380
aaaaaaaaaa aacttcaaac g                                              21

<210> SEQ ID NO 381
<211> LENGTH: 21
<212> TYPE: DNA

```
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 381
atcaaattac tctaaactac g                                           21

<210> SEQ ID NO 382
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 382
aaaactaaaa accaaaactc g                                           21

<210> SEQ ID NO 383
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 383
aaccaaaact cgaaaactac g                                           21

<210> SEQ ID NO 384
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 384
atacaaaaac ctcaaaaacc g                                           21

<210> SEQ ID NO 385
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 385
aaaacctcaa aaaccgatac g                                           21

<210> SEQ ID NO 386
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted METHYLATED ANTISENSE strand of the promoter
      region of the LINE-1 element

<400> SEQUENCE: 386
taaaataaat aaaataaaac g                                           21
```

<210> SEQ ID NO 387
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 387
aaaaaaaaac caaaataacc a                                             21

<210> SEQ ID NO 388
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 388
aaccaaataa aaacaactcc a                                             21

<210> SEQ ID NO 389
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 389
tccaatctac aactcccaac a                                             21

<210> SEQ ID NO 390
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 390
ctacaactcc caacataaac a                                             21

<210> SEQ ID NO 391
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 391
caactcccaa cataaacaac a                                             21

<210> SEQ ID NO 392
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter region of the LINE-1 element

<400> SEQUENCE: 392
acataaacaa cacaaaaaac a                                              21

<210> SEQ ID NO 393
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 393
acatttccat ctaaaatacc a                                              21

<210> SEQ ID NO 394
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 394
aaaaatacca aacaataaac a                                              21

<210> SEQ ID NO 395
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 395
acacaaacca atatatatac a                                              21

<210> SEQ ID NO 396
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 396
aaccaatata tatacacacc a                                              21

<210> SEQ ID NO 397
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 397
aatatatata cacaccatac a                                              21

<210> SEQ ID NO 398
<211> LENGTH: 21

```
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 398
tatatataca caccatacac a                                              21

<210> SEQ ID NO 399
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 399
atacacacca tacacaaacc a                                              21

<210> SEQ ID NO 400
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 400
tacacaaacc aaaacaaaac a                                              21

<210> SEQ ID NO 401
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 401
cattacctca cctaaaaaac a                                              21

<210> SEQ ID NO 402
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 402
aaatcaaaaa aaaaaataac a                                              21

<210> SEQ ID NO 403
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 403
```
caaaaaaaaa aataacaatc a                                              21

<210> SEQ ID NO 404
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 404
acaatcacac ctaaaaaatc a                                              21

<210> SEQ ID NO 405
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 405
aaatcaaatc actcccaccc a                                              21

<210> SEQ ID NO 406
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 406
cactcccacc caaatattac a                                              21

<210> SEQ ID NO 407
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 407
aatattacac ttttcaaacc a                                              21

<210> SEQ ID NO 408
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 408
ttcaaaccaa cttaaaaaac a                                              21

<210> SEQ ID NO 409
<211> LENGTH: 21
<212> TYPE: DNA
<213> ORGANISM: Artificial
<220> FEATURE:
<223> OTHER INFORMATION: COMPLEMEMTARY PRIMER specific for the

```
      bisulfite-converted DEMETHYLATED ANTISENSE strand of the promoter
      region of the LINE-1 element

<400> SEQUENCE: 409
aaaccaactt aaaaaacaac a                                              21

<210> SEQ ID NO 410
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 410
cttaaaaaac aacacaccac a                                              21

<210> SEQ ID NO 411
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 411
ctatatccca cacctaactc a                                              21

<210> SEQ ID NO 412
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 412
cctaactcaa aaaatcctac a                                              21

<210> SEQ ID NO 413
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 413
tcaaaaaatc ctacacccac a                                              21

<210> SEQ ID NO 414
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 414
tcctacaccc acaaaatctc a                                              21

<210> SEQ ID NO 415
```

```
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 415
ctaaaatcaa actacaaaac a                                              21

<210> SEQ ID NO 416
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 416
tcaaactaca aacaacaac a                                               21

<210> SEQ ID NO 417
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 417
aacaaaacta aaaaaaaaac a                                              21

<210> SEQ ID NO 418
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 418
aaactaaaaa aaaaacaccc a                                              21

<210> SEQ ID NO 419
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 419
cttaaataaa caaacaacc a                                               21

<210> SEQ ID NO 420
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 420
```
acaaaacaac caaaaaactc a         21

<210> SEQ ID NO 421
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 421
aacaataatt ctcccaacac a         21

<210> SEQ ID NO 422
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 422
gcaactaaaa atctaaaaac a         21

<210> SEQ ID NO 423
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 423
atccctaact cctaaccccc a         21

<210> SEQ ID NO 424
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 424
aacacactaa cacctcacac a         21

<210> SEQ ID NO 425
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 425
ccaaaaaaaa catctacacc a         21

<210> SEQ ID NO 426
<211> LENGTH: 21
<212> TYPE: DNA
<213> ORGANISM: Artificial
<220> FEATURE:

-continued

<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 426
aaaactaaaa actctaaaac a                                           21

<210> SEQ ID NO 427
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 427
aaaactctaa aacacaaaac a                                           21

<210> SEQ ID NO 428
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 428
ctctcctcct ccaaaaaaac a                                           21

<210> SEQ ID NO 429
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 429
aaataaaaaa taattttaac a                                           21

<210> SEQ ID NO 430
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 430
aaaaaaaaaa aacttcaaac a                                           21

<210> SEQ ID NO 431
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 431
atcaaattac tctaaactac a                                           21

```
<210> SEQ ID NO 432
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 432
aaaactaaaa accaaaactc a                                              21

<210> SEQ ID NO 433
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 433
aaccaaaact caaaaactac a                                              21

<210> SEQ ID NO 434
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 434
atacaaaaac ctcaaaaacc a                                              21

<210> SEQ ID NO 435
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 435
aaaacctcaa aaaccaatac a                                              21

<210> SEQ ID NO 436
<211> LENGTH: 21
<212> TYPE: DNA
<213> ORGANISM: Artificial
<220> FEATURE:
<223> OTHER INFORMATION: COMPLEMEMTARY PRIMER specific for the
      bisulfite-converted DEMETHYLATED ANTISENSE strand of the promoter
      region of the LINE-1 element

<400> SEQUENCE: 436
taaaataaat aaaataaaac a                                              21

<210> SEQ ID NO 437
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted
      METHYLATED SENSE strand of the Alu element
```

```
<400> SEQUENCE: 437
ggtcgggcgc ggtggtttac                                              20

<210> SEQ ID NO 438
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 438
ttttagtatt tgggaggtc                                               20

<210> SEQ ID NO 439
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 439
gtattttggg aggtcgaggc                                              20

<210> SEQ ID NO 440
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 440
tttgggaggt cgaggcgggc                                              20

<210> SEQ ID NO 441
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 441
ttatttgagg ttaggagatc                                              20

<210> SEQ ID NO 442
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 442
ggttaatatg gtgaaatttc                                              20

<210> SEQ ID NO 443
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 443
```
taaaaatata aaaattagtc                                           20

<210> SEQ ID NO 444
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 444
aatataaaaa ttagtcgggc                                           20

<210> SEQ ID NO 445
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 445
aattagtcgg gcgtggtggc                                           20

<210> SEQ ID NO 446
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 446
ttagtcgggc gtggtggcgc                                           20

<210> SEQ ID NO 447
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 447
agtcgggcgt ggtggcgcgc                                           20

<210> SEQ ID NO 448
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 448
gtttgtaatt ttagttattc                                           20

<210> SEQ ID NO 449
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 449
gaggttgagg taggagaatc                                               20

<210> SEQ ID NO 450
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 450
taggagaatc gtttgaattc                                               20

<210> SEQ ID NO 451
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 451
atcgtttgaa ttcgggaggc                                               20

<210> SEQ ID NO 452
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 452
ggttgtagtg agtcgagatc                                               20

<210> SEQ ID NO 453
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 453
ttgtagtgag tcgagatcgc                                               20

<210> SEQ ID NO 454
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 454
tattgtattt tagtttgggc                                               20

<210> SEQ ID NO 455
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 455
tttagtttgg gcgatagagc                                               20

<210> SEQ ID NO 456
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the Alu element

<400> SEQUENCE: 456
gggcgataga gcgagatttc                                                   20

<210> SEQ ID NO 457
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 457
ggttgggtgt ggtggtttat                                                   20

<210> SEQ ID NO 458
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 458
ttttagtatt ttgggaggtt                                                   20

<210> SEQ ID NO 459
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 459
gtattttggg aggttgaggt                                                   20

<210> SEQ ID NO 460
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 460
tttgggaggt tgaggtgggt                                                   20

<210> SEQ ID NO 461
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 461
ttatttgagg ttaggagatt                                                   20

<210> SEQ ID NO 462
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 462
ggttaatatg gtgaaatttt                                              20

<210> SEQ ID NO 463
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 463
taaaaatata aaaattagtt                                              20

<210> SEQ ID NO 464
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 464
aatataaaaa ttagttgggt                                              20

<210> SEQ ID NO 465
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 465
aattagttgg gtgtggtggt                                              20

<210> SEQ ID NO 466
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 466
ttagttgggt gtggtggtgt                                              20

<210> SEQ ID NO 467
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 467
agttgggtgt ggtggtgtgt                                              20

-continued

```
<210> SEQ ID NO 468
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 468
gtttgtaatt ttagttattt                                                 20

<210> SEQ ID NO 469
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 469
gaggttgagg taggagaatt                                                 20

<210> SEQ ID NO 470
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 470
taggagaatt gtttgaattt                                                 20

<210> SEQ ID NO 471
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 471
attgtttgaa tttgggaggt                                                 20

<210> SEQ ID NO 472
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 472
ggttgtagtg agttgagatt                                                 20

<210> SEQ ID NO 473
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 473
ttgtagtgag ttgagattgt                                                 20

<210> SEQ ID NO 474
```

```
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 474
tattgtattt tagtttgggt                                                     20

<210> SEQ ID NO 475
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 475
tttagtttgg gtgatagagt                                                     20

<210> SEQ ID NO 476
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the Alu element

<400> SEQUENCE: 476
gggtgataga gtgagatttt                                                     20

<210> SEQ ID NO 477
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the Alu element

<400> SEQUENCE: 477 tttttttaaaa cgaaatctcg                                                    20

<210> SEQ ID NO 478
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 478
aacgaaatct cgctctatcg                                                     20

<210> SEQ ID NO 479
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 479
caaactaaaa tacaataacg                                                     20

<210> SEQ ID NO 480
<211> LENGTH: 20
```

```
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 480
aactaaaata caataacgcg                                             20

<210> SEQ ID NO 481
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 481
aatacaataa cgcgatctcg                                             20

<210> SEQ ID NO 482
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 482
tcgactcact acaacctccg                                             20

<210> SEQ ID NO 483
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 483
actacaacct ccgcctcccg                                             20

<210> SEQ ID NO 484
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 484
ccgcctcccg aattcaaacg                                             20

<210> SEQ ID NO 485
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 485
tctcctacct caacctcccg                                             20

<210> SEQ ID NO 486
<211> LENGTH: 20
<212> TYPE: DNA
```

```
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 486
aataactaaa attacaaacg                                            20

<210> SEQ ID NO 487
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 487
taactaaaat tacaaacgcg                                            20

<210> SEQ ID NO 488
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 488
actaaaatta caaacgcgcg                                            20

<210> SEQ ID NO 489
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 489
tacaaacgcg cgccaccacg                                            20

<210> SEQ ID NO 490
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 490
aacgcgcgcc accacgcccg                                            20

<210> SEQ ID NO 491
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 491
ttatattttt aataaaaacg                                            20

<210> SEQ ID NO 492
<211> LENGTH: 20
<212> TYPE: DNA
<213> ORGANISM: Artificial
```

<220> FEATURE:
<223> OTHER INFORMATION: COMPLEMENTARY PRIMER specific of the METHYLATED
      SENSE strand of the Alu element

<400> SEQUENCE: 492
tattaaccaa aataatctcg                                                    20

<210> SEQ ID NO 493
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 493
tcctaacctc aaataatccg                                                    20

<210> SEQ ID NO 494
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 494
aacctcaaat aatccgcccg                                                    20

<210> SEQ ID NO 495
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 495
caaataatcc gcccgcctcg                                                    20

<210> SEQ ID NO 496
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 496
aaatactaaa attacaaacg                                                    20

<210> SEQ ID NO 497
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 497
attacaaacg taaaccaccg                                                    20

<210> SEQ ID NO 498
<211> LENGTH: 20
<212> TYPE: DNA
<213> ORGANISM: Artificial
<220> FEATURE:

<223> OTHER INFORMATION: COMPLEMENTARY PRIMER specific of the METHYLATED
      SENSE strand of the Alu element

<400> SEQUENCE: 498
tacaaacgta aaccaccgcg                                                      20

<210> SEQ ID NO 499
<211> LENGTH: 20
<212> TYPE: DNA
<213> ORGANISM: Artificial
<220> FEATURE:
<223> OTHER INFORMATION: COMPLEMENTARY PRIMER specific of the METHYLATED
      SENSE strand of the Alu element

<400> SEQUENCE: 499
aacgtaaacc accgcgcccg                                                      20

<210> SEQ ID NO 500
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 500 tttttaaaa caaatctca                                                        20

<210> SEQ ID NO 501
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 501
aacaaaatct cactctatca                                                      20

<210> SEQ ID NO 502
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 502
caaactaaaa tacaataaca                                                      20

<210> SEQ ID NO 503
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 503
aactaaaata caataacaca                                                      20

<210> SEQ ID NO 504
<211> LENGTH: 20
<212> TYPE: DNA
<213> ORGANISM: Artificial
<220> FEATURE:
<223> OTHER INFORMATION: COMPLEMENTARY PRIMER specific of theDE METHYLATED SENSE strand of the Alu element

<400> SEQUENCE: 504
aatacaataa cacaatctca                                               20

<210> SEQ ID NO 505
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 505
tcaactcact acaacctcca                                               20

<210> SEQ ID NO 506
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 506
actacaacct ccacctccca                                               20

<210> SEQ ID NO 507
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 507
ccacctccca aattcaaaca                                               20

<210> SEQ ID NO 508
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 508
tctcctacct caacctccca                                               20

<210> SEQ ID NO 509
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 509
aataactaaa attacaaaca                                               20

<210> SEQ ID NO 510
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element -continued <210> SEQ ID NO 511
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 511
actaaaatta caaacacaca                                              20

<210> SEQ ID NO 512
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 512
tacaaacaca caccaccaca                                              20

<210> SEQ ID NO 513
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 513
aacacacacc accacaccca                                              20

<210> SEQ ID NO 514
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 514
ttatattttt aataaaaaca                                              20

<210> SEQ ID NO 515
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 515
tattaaccaa aataatctca                                              20

<210> SEQ ID NO 516
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

```
<400> SEQUENCE: 516
tcctaacctc aaataatcca                                               20

<210> SEQ ID NO 517
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 517
aacctcaaat aatccaccca                                               20

<210> SEQ ID NO 518
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 518
caaataatcc acccacctca                                               20

<210> SEQ ID NO 519
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 519
aaatactaaa attacaaaca                                               20

<210> SEQ ID NO 520
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 520
attacaaaca taaaccacca                                               20

<210> SEQ ID NO 521
<211> LENGTH: 20
<212> TYPE: DNA
<213> ORGANISM: Artificial
<220> FEATURE:
<223> OTHER INFORMATION: COMPLEMENTARY PRIMER specific of theDE
      METHYLATED SENSE strand of the Alu element

<400> SEQUENCE: 521
tacaaacata aaccaccaca                                               20

<210> SEQ ID NO 522
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the Alu element

<400> SEQUENCE: 522
```
aacgtaaacc accgcgccca                                               20

<210> SEQ ID NO 523
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 523
tttttttgag acggagtttc                                               20

<210> SEQ ID NO 524
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 524
agacggagtt tcgttttgtc                                               20

<210> SEQ ID NO 525
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 525
agacggagtt tcgttttgtc                                               20

<210> SEQ ID NO 526
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 526
ttaggttgga gtgtagtggc                                               20

<210> SEQ ID NO 527
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 527
aggttggagt gtagtggcgc                                               20

<210> SEQ ID NO 528
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 528

```
gagtgtagtg gcgcgatttc                                              20
```

<210> SEQ ID NO 529
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 529

```
ttcggtttat tgtaattttc                                              20
```

<210> SEQ ID NO 530
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 530

```
tattgtaatt ttcgttttc                                               20
```

<210> SEQ ID NO 531
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 531

```
ttcgtttttc gggtttaagc                                              20
```

<210> SEQ ID NO 532
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 532

```
tttttttgtt ttagttttc                                               20
```

<210> SEQ ID NO 533
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 533

```
gagtagttgg gattataggc                                              20
```

<210> SEQ ID NO 534
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 534

```
gtagttggga ttataggcgc                                              20
```

<210> SEQ ID NO 535
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 535
agttgggatt ataggcgcgc                                         20

<210> SEQ ID NO 536
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 536
ttataggcgc gcgttattac                                         20

<210> SEQ ID NO 537
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 537
aggcgcgcgt tattacgttc                                         20

<210> SEQ ID NO 538
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 538
tttgtatttt tagtagagac                                         20

<210> SEQ ID NO 539
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 539
atgttggtta ggatggtttc                                         20

<210> SEQ ID NO 540
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 540
tttttgattt taggtgattc                                         20

<210> SEQ ID NO 541
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 541
tgattttagg tgattcgttc                                               20

<210> SEQ ID NO 542
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 542
ttaggtgatt cgttcgtttc                                               20

<210> SEQ ID NO 543
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 543
aaagtgttgg gattataggc                                               20

<210> SEQ ID NO 544
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 544
gattataggc gtgagttatc                                               20

<210> SEQ ID NO 545
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 545
ttataggcgt gagttatcgc                                               20

<210> SEQ ID NO 546
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the Alu element

<400> SEQUENCE: 546
aggcgtgagt tatcgcgttc                                               20

<210> SEQ ID NO 547
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 547 ttttttttgag actgagtttt                                              20

<210> SEQ ID NO 548
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 548
agactgagtt tcttttttgtt                                              20

<210> SEQ ID NO 549
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 549
agactgagtt tcttttttgtt                                              20

<210> SEQ ID NO 550
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 550
ttaggttgga gtgtagtggt                                               20

<210> SEQ ID NO 551
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 551
aggttggagt gtagtggctt                                               20

<210> SEQ ID NO 552
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 552
gagtgtagtg gctctatttt                                          20

<210> SEQ ID NO 553
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 553
ttctgtttat tgtaatttttt                                         20

<210> SEQ ID NO 554
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 554
tattgtaatt ttctttttt                                           20

<210> SEQ ID NO 555
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element
<400> SEQUENCE: 555
ttcttttttc tggtttaagt                                          20

<210> SEQ ID NO 556
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 556
tttttttgtt ttagttttttt                                         20

<210> SEQ ID NO 557
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 557
gagtagttgg gattataggt                                          20

<210> SEQ ID NO 558
<211> LENGTH: 20
<212> TYPE: DNA
<213> ORGANISM: Artificial
<220> FEATURE:

-continued

<223> OTHER INFORMATION: SEQUENCE-IDENTICAL primer specific for the
     bisulfite-converted DEMETHYLATED ANTISENSE strand of the Alu
     element

<400> SEQUENCE: 558
gtagttggga ttataggctt                                              20

<210> SEQ ID NO 559
<211> LENGTH: 20
<212> TYPE: DNA
<213> ORGANISM: Artificial
<220> FEATURE:
<223> OTHER INFORMATION: SEQUENCE-IDENTICAL primer specific for the
     bisulfite-converted DEMETHYLATED ANTISENSE strand of the Alu
     element

<400> SEQUENCE: 559
agttgggatt ataggctctt                                              20

<210> SEQ ID NO 560
<211> LENGTH: 20
<212> TYPE: DNA
<213> ORGANISM: Artificial
<220> FEATURE:
<223> OTHER INFORMATION: SEQUENCE-IDENTICAL primer specific for the
     bisulfite-converted DEMETHYLATED ANTISENSE strand of the Alu
     element

<400> SEQUENCE: 560
ttataggctc tctttattat                                              20

<210> SEQ ID NO 561
<211> LENGTH: 20
<212> TYPE: DNA
<213> ORGANISM: Artificial
<220> FEATURE:
<223> OTHER INFORMATION: SEQUENCE-IDENTICAL primer specific for the
     bisulfite-converted DEMETHYLATED ANTISENSE strand of the Alu
     element

<400> SEQUENCE: 561
aggctctctt tattactttt                                              20

<210> SEQ ID NO 562
<211> LENGTH: 20
<212> TYPE: DNA
<213> ORGANISM: Artificial
<220> FEATURE:
<223> OTHER INFORMATION: SEQUENCE-IDENTICAL primer specific for the
     bisulfite-converted DEMETHYLATED ANTISENSE strand of the Alu
     element

<400> SEQUENCE: 562
tttgtatttt tagtagagat                                              20

<210> SEQ ID NO 563
<211> LENGTH: 20
<212> TYPE: DNA
<213> ORGANISM: Artificial
<220> FEATURE:
<223> OTHER INFORMATION: SEQUENCE-IDENTICAL primer specific for the
     bisulfite-converted DEMETHYLATED ANTISENSE strand of the Alu
     element

<400> SEQUENCE: 563
atgttggtta ggatggtttt                                              20

<210> SEQ ID NO 564
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 564
tttttgattt taggtgattt                                                 20

<210> SEQ ID NO 565
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 565
tgattttagg tgattctttt                                                 20

<210> SEQ ID NO 566
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 566
ttaggtgatt ctttcttttt                                                 20

<210> SEQ ID NO 567
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 567
aaagtgttgg gattataggt                                                 20

<210> SEQ ID NO 568
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 568
gattataggc ttgagttatt                                                 20

<210> SEQ ID NO 569
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element -continued

<400> SEQUENCE: 569
ttataggctt gagttatctt                                        20

<210> SEQ ID NO 570
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the Alu
      element

<400> SEQUENCE: 570
aggcttgagt tatctctttt                                        20

<210> SEQ ID NO 571
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu
      element

<400> SEQUENCE: 571
accgaacgcg ataactcacg                                        20

<210> SEQ ID NO 572
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu
      element

<400> SEQUENCE: 572
cccaacactt taaaaaaccg                                        20

<210> SEQ ID NO 573
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 573
cactttaaaa aaccgaaacg                                        20

<210> SEQ ID NO 574
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 574
ttaaaaaacc gaaacgaacg                                        20

<210> SEQ ID NO 575
<211> LENGTH: 20
<212> TYPE: DNA
<213> ORGANISM: Artificial
<220> FEATURE:
<223> OTHER INFORMATION: COMPLEMENTARY PRIMER specific for the bisulfite-converted METHYLATED ANTISENSE strand of the Alu element

<400> SEQUENCE: 575
cacctaaaat caaaaaatcg                                              20

<210> SEQ ID NO 576
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 576
accaacataa taaaaccccg                                              20

<210> SEQ ID NO 577
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 577
aaaaatacaa aaattaaccg                                              20

<210> SEQ ID NO 578
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 578
atacaaaaat taaccgaacg                                              20

<210> SEQ ID NO 579
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 579
attaaccgaa cgtaataacg                                              20

<210> SEQ ID NO 580
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 580
taaccgaacg taataacgcg                                              20

<210> SEQ ID NO 581
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 581
accgaacgta ataacgcgcg                                           20

<210> SEQ ID NO 582
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 582
cctataatcc caactactcg                                           20

<210> SEQ ID NO 583
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 583
gaactaaaac aaaaaaatcg                                           20

<210> SEQ ID NO 584
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 584
aaaaaaatcg cttaaacccg                                           20

<210> SEQ ID NO 585
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 585
tcgcttaaac ccgaaaaacg                                           20

<210> SEQ ID NO 586
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 586
acgaaaatta caataaaccg                                           20

<210> SEQ ID NO 587
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

```
<400> SEQUENCE: 587
attacaataa accgaaatcg                                              20

<210> SEQ ID NO 588
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 588
tacaataaac cgaaatcgcg                                              20

<210> SEQ ID NO 589
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 589
actacactcc aacctaaacg                                              20

<210> SEQ ID NO 590
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 590
ccaacctaaa cgacaaaacg                                              20

<210> SEQ ID NO 591
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted METHYLATED ANTISENSE strand of the Alu element

<400> SEQUENCE: 591
aacgacaaaa cgaaactccg                                              20

<210> SEQ ID NO 592
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 592
accaaacaca ataactcaca                                              20

<210> SEQ ID NO 593
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element
```

<400> SEQUENCE: 593
cccaacactt taaaaaacca                                              20

<210> SEQ ID NO 594
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 594
cactttaaaa aaccaaaaca                                              20

<210> SEQ ID NO 595
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 595
ttaaaaaacc aaaacaaaca                                              20

<210> SEQ ID NO 596
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 596
cacctaaaat caaaaaatca                                              20

<210> SEQ ID NO 597
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 597
accaacataa taaaacccca                                              20

<210> SEQ ID NO 598
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 598
aaaaatacaa aaattaacca                                              20

<210> SEQ ID NO 599
<211> LENGTH: 20
<212> TYPE: DNA

<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 599
atacaaaaat taaccaaaca                                              20

<210> SEQ ID NO 600
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 600
attaaccaaa cataataaca                                              20

<210> SEQ ID NO 601
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 601
taaccaaaca taataacaca                                              20

<210> SEQ ID NO 602
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 602
accaaacata ataacacaca                                              20

<210> SEQ ID NO 603
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 603
cctataatcc caactactca                                              20

<210> SEQ ID NO 604
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 604
gaactaaaac aaaaaaatca                                              20

<210> SEQ ID NO 605
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 605
aaaaaaatca cttaaaccca                                               20

<210> SEQ ID NO 606
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 606
tcacttaaac ccaaaaaaca                                               20

<210> SEQ ID NO 607
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 607
acaaaaatta caataaacca                                               20

<210> SEQ ID NO 608
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 608
attacaataa accaaaatca                                               20

<210> SEQ ID NO 609
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 609
tacaataaac caaaatcaca                                               20

<210> SEQ ID NO 610
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu

```
                                    element

<400> SEQUENCE: 610
actacactcc aacctaaaca                                              20

<210> SEQ ID NO 611
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 611
ccaacctaaa caacaaaaca                                              20

<210> SEQ ID NO 612
<211> LENGTH: 20
<212> TYPE: DNA
<213> ORGANISM: Artificial
<220> FEATURE:
<223> OTHER INFORMATION: COMPLEMENTARY PRIMER specific for the
      bisulfite-converted DEMETHYLATED ANTISENSE strand of the Alu
      element

<400> SEQUENCE: 612
aacaacaaaa caaaactcca                                              20

<210> SEQ ID NO 613
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 613
atgattttat ttttaatttc                                              20

<210> SEQ ID NO 614
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 614
gggttaaatg gattaagggc                                              20

<210> SEQ ID NO 615
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 615
tttagggata taaaaattgc                                              20

<210> SEQ ID NO 616
<211> LENGTH: 20
<212> TYPE: DNA
<213> ORGANISM: Artificial
<220> FEATURE:
```

```
<223> OTHER INFORMATION: SEQUENCE-IDENTICAL primer specific for the
      bisulfite-converted METHYLATED SENSE strand of the HERV-K element

<400> SEQUENCE: 616
agagtttgaa atatggtttc                                                   20

<210> SEQ ID NO 617
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 617
gggaagggaa agatttgatc                                                   20

<210> SEQ ID NO 618
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 618
atttgatcgt tttttagttc                                                   20

<210> SEQ ID NO 619
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 619
tttgggtaat ggaatgtttc                                                   20

<210> SEQ ID NO 620
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 620
aatgtttcgg tataaaattc                                                   20

<210> SEQ ID NO 621
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 621
ggtataaaat tcgattgtac                                                   20

<210> SEQ ID NO 622
<211> LENGTH: 20
<212> TYPE: DNA
<213> ORGANISM: Artificial
<220> FEATURE:
<223> OTHER INFORMATION: SEQUENCE-IDENTICAL primer specific for the
``` bisulfite-converted METHYLATED SENSE strand of the HERV-K element

<400> SEQUENCE: 622
atgtaaagat ttttgtttac                                          20

<210> SEQ ID NO 623
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 623 tttttagag aaatatttac                                           20

<210> SEQ ID NO 624
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 624 ggattttta tatgttgaac                                           20

<210> SEQ ID NO 625
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 625
atgttgaacg ttggttttc                                           20

<210> SEQ ID NO 626
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 626 agtttttat tgtattttac                                           20

<210> SEQ ID NO 627
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 627 tttttattt ggtgtttaac                                           20

<210> SEQ ID NO 628
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 628
tttggggtga aggtatattc                                               20

<210> SEQ ID NO 629
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 629
gggtgaaggt atattcgagc                                               20

<210> SEQ ID NO 630
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 630
gtggttattg aggataagtc                                               20

<210> SEQ ID NO 631
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 631
ataagtcgat aagagatttc                                               20

<210> SEQ ID NO 632
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 632
atatttatag ttagttttac                                               20

<210> SEQ ID NO 633
<211> LENGTH: 19
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 633
tacggtaagt ttgtgtatt                                                19

<210> SEQ ID NO 634
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

```
<400> SEQUENCE: 634
tattttaaat agaagatagc                                              20

<210> SEQ ID NO 635
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 635
aaaaaatttt agaaggaaac                                              20

<210> SEQ ID NO 636
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 636
aaacggaaat tttatattgc                                              20

<210> SEQ ID NO 637
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 637
tgcgaatatg tagtagagtc                                              20

<210> SEQ ID NO 638
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 638
tcgttaatgg tttagttaac                                              20

<210> SEQ ID NO 639
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 639
gttattagag tttaaattac                                              20

<210> SEQ ID NO 640
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 640
``` tttttagtagg ttaggtgatc                                              20

<210> SEQ ID NO 641
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 641
gtaatattat aattttaagc                                               20

<210> SEQ ID NO 642
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 642
gtttattaat attggttatc                                               20

<210> SEQ ID NO 643
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 643
attaatattg gttatcggtc                                               20

<210> SEQ ID NO 644
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 644
atcggtcgaa ttttagtatc                                               20

<210> SEQ ID NO 645
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 645
agggagttat atttttagtc                                               20

<210> SEQ ID NO 646
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 646
aaggaaggag atattgaggc                                           20

<210> SEQ ID NO 647
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 647
gcgtggtaat ttttagtaac                                           20

<210> SEQ ID NO 648
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 648
tttttagtaa cgttagaatc                                           20

<210> SEQ ID NO 649
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 649
atgtggattt ttgtgtttac                                           20

<210> SEQ ID NO 650
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 650
gatttttgtg tttacggatc                                           20

<210> SEQ ID NO 651
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 651
tttgtgttta cggatcgatc                                           20

<210> SEQ ID NO 652
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 652
gatcgatcgt gggaggtttc                                           20

<210> SEQ ID NO 653
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 653
tgattgaaat attaaaaggc                                          20

<210> SEQ ID NO 654
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 654
ttataaattt tatattaatc                                          20

<210> SEQ ID NO 655
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 655
taggtgtatt taatagtttc                                          20

<210> SEQ ID NO 656
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 656
ttcgaagaga tagtgatatc                                          20

<210> SEQ ID NO 657
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 657
gagatagtga tatcgagaac                                          20

<210> SEQ ID NO 658
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 658
cgagaacggg ttatgatgac                                          20

<210> SEQ ID NO 659
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 659
cgggttatga tgacgatggc                                               20

<210> SEQ ID NO 660
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED SENSE strand of the HERV-K element

<400> SEQUENCE: 660
atgacgatgg cggttttgtc                                               20

<210> SEQ ID NO 661
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 661
atgattttat ttttaatttt                                               20

<210> SEQ ID NO 662
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 662
gggttaaatg gattaagggt                                               20

<210> SEQ ID NO 663
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 663
tttagggata taaaaattgt                                               20

<210> SEQ ID NO 664
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 664
agagtttgaa atatggtttt                                         20

<210> SEQ ID NO 665
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 665
gggaagggaa agatttgatt                                         20

<210> SEQ ID NO 666
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 666
atttgatctt tttttagttt                                         20

<210> SEQ ID NO 667
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 667
tttgggtaat ggaatgtttt                                         20

<210> SEQ ID NO 668
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 668
aatgtttctg tataaaattt                                         20

<210> SEQ ID NO 669
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 669
ggtataaaat tctattgtat                                         20

<210> SEQ ID NO 670
<211> LENGTH: 20
<212> TYPE: DNA
<213> ORGANISM: Artificial
<220> FEATURE:

<223> OTHER INFORMATION: SEQUENCE-IDENTICAL primer specific for the
      bisulfite-converted DEMETHYLATED SENSE strand of the HERV-K
      element

<400> SEQUENCE: 670
atgtaaagat ttttgtttat                                             20

<210> SEQ ID NO 671
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 671 tttttagag aaatatttat                                              20

<210> SEQ ID NO 672
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 672 ggattttta tatgttgaat                                              20

<210> SEQ ID NO 673
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 673
atgttgaact ttggttttt                                              20

<210> SEQ ID NO 674
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 674
agttttttat tgtattttat                                             20

<210> SEQ ID NO 675
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 675 tttttattt ggtgtttaat                                              20

```
<210> SEQ ID NO 676
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 676
tttggggtga aggtatattt                                          20

<210> SEQ ID NO 677
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 677
gggtgaaggt atattctagt                                          20

<210> SEQ ID NO 678
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 678
gtggttattg aggataagtt                                          20

<210> SEQ ID NO 679
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 679
ataagtctat aagagatttt                                          20

<210> SEQ ID NO 680
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 680
atatttatag ttagttttat                                          20

<210> SEQ ID NO 681
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element
```

```
<400> SEQUENCE: 681
tactgtaagt ttgtgtattt                                              20

<210> SEQ ID NO 682
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 682
tattttaaat agaagatagt                                              20

<210> SEQ ID NO 683
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 683
aaaaaatttt agaaggaaat                                              20

<210> SEQ ID NO 684
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 684
aaactgaaat tttatattgt                                              20

<210> SEQ ID NO 685
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 685
tgctaatatg tagtagagtt                                              20

<210> SEQ ID NO 686
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 686
tctttaatgg tttagttaat                                              20

<210> SEQ ID NO 687
<211> LENGTH: 20
<212> TYPE: DNA
<213> ORGANISM: Artificial
```

```
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 687
gttattagag tttaaattat                                          20

<210> SEQ ID NO 688
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 688
ttttagtagg ttaggtgatt                                          20

<210> SEQ ID NO 689
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 689
gtaatattat aattttaagt                                          20

<210> SEQ ID NO 690
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 690
gtttattaat attggttatt                                          20

<210> SEQ ID NO 691
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 691
attaatattg gttatctgtt                                          20

<210> SEQ ID NO 692
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 692
atctgtctaa ttttagtatt                                          20
```

<210> SEQ ID NO 693
<211> LENGTH: 20
<212> TYPE: DNA
<213> ORGANISM: Artificial
<220> FEATURE:
<223> OTHER INFORMATION: SEQUENCE-IDENTICAL primer specific for the bisulfite-converted DEMETHYLATED SENSE strand of the HERV-K element

<400> SEQUENCE: 693
agggagttat atttttagtt                                           20

<210> SEQ ID NO 694
<211> LENGTH: 20
<212> TYPE: DNA
<213> ORGANISM: Artificial
<220> FEATURE:
<223> OTHER INFORMATION: SEQUENCE-IDENTICAL primer specific for the bisulfite-converted DEMETHYLATED SENSE strand of the HERV-K element

<400> SEQUENCE: 694
aaggaaggag atattgaggt                                           20

<210> SEQ ID NO 695
<211> LENGTH: 20
<212> TYPE: DNA
<213> ORGANISM: Artificial
<220> FEATURE:
<223> OTHER INFORMATION: SEQUENCE-IDENTICAL primer specific for the bisulfite-converted DEMETHYLATED SENSE strand of the HERV-K element

<400> SEQUENCE: 695
gcttggtaat ttttagtaat                                           20

<210> SEQ ID NO 696
<211> LENGTH: 20
<212> TYPE: DNA
<213> ORGANISM: Artificial
<220> FEATURE:
<223> OTHER INFORMATION: SEQUENCE-IDENTICAL primer specific for the bisulfite-converted DEMETHYLATED SENSE strand of the HERV-K element

<400> SEQUENCE: 696
tttttagtaa ctttagaatt                                           20

<210> SEQ ID NO 697
<211> LENGTH: 20
<212> TYPE: DNA
<213> ORGANISM: Artificial
<220> FEATURE:
<223> OTHER INFORMATION: SEQUENCE-IDENTICAL primer specific for the bisulfite-converted DEMETHYLATED SENSE strand of the HERV-K element

<400> SEQUENCE: 697
atgtggattt ttgtgtttat                                           20

<210> SEQ ID NO 698
<211> LENGTH: 20
<212> TYPE: DNA
<213> ORGANISM: Artificial
<220> FEATURE:
<223> OTHER INFORMATION: SEQUENCE-IDENTICAL primer specific for the bisulfite-converted DEMETHYLATED SENSE strand of the HERV-K element

<400> SEQUENCE: 698
gatttttgtg tttactgatt        20

<210> SEQ ID NO 699
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 699
tttgtgttta ctgatctatt        20

<210> SEQ ID NO 700
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 700
gatctatctt gggaggtttt        20

<210> SEQ ID NO 701
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 701
tgattgaaat attaaaaggt        20

<210> SEQ ID NO 702
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 702
ttataaattt tatattaatt        20

<210> SEQ ID NO 703
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 703
taggtgtatt taatagtttt        20

<210> SEQ ID NO 704
<211> LENGTH: 20
<212> TYPE: DNA

```
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 704
ttctaagaga tagtgatatt                                              20

<210> SEQ ID NO 705
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 705
gagatagtga tatctagaat                                              20

<210> SEQ ID NO 706
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 706
ctagaactgg ttatgatgat                                              20

<210> SEQ ID NO 707
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 707
ctggttatga tgactatggt                                              20

<210> SEQ ID NO 708
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED SENSE strand of the HERV-K
      element

<400> SEQUENCE: 708
atgactatgg ctgttttgtt                                              20

<210> SEQ ID NO 709
<211> LENGTH: 20
<212> TYPE: DNA
<213> ORGANISM: Artificial
<220> FEATURE:
<223> OTHER INFORMATION: complementary primer sequence specific for the
      METHYLATED SENSE strand of the HERV-K element

<400> SEQUENCE: 709
aaaaaaaata aaaaaacccg                                              20
```

<210> SEQ ID NO 710
<211> LENGTH: 20
<212> TYPE: DNA
<213> ORGANISM: Artificial
<220> FEATURE:
<223> OTHER INFORMATION: complementary primer sequence specific for the
      METHYLATED SENSE strand of the HERV-K element

<400> SEQUENCE: 710
aaaaacccga aaaaccaacg                                                    20

<210> SEQ ID NO 711
<211> LENGTH: 20
<212> TYPE: DNA
<213> ORGANISM: Artificial
<220> FEATURE:
<223> OTHER INFORMATION: complementary primer sequence specific for the
      METHYLATED SENSE strand of the HERV-K element

<400> SEQUENCE: 711
tcaacatata aaaaatcccg                                                    20

<210> SEQ ID NO 712
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 712
cattcataaa tatttctccg                                                    20

<210> SEQ ID NO 713
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 713
aaaatcaaca aacaaacacg                                                    20

<210> SEQ ID NO 714
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 714
aaacatctca atactttacg                                                    20

<210> SEQ ID NO 715
<211> LENGTH: 20
<212> TYPE: DNA
<213> ORGANISM: Artificial
<220> FEATURE:
<223> OTHER INFORMATION: complementary primer sequence specific for the
      METHYLATED SENSE strand of the HERV-K element

<400> SEQUENCE: 715
ataaataaaa tattcaatcg                                                    20

-continued

<210> SEQ ID NO 716
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 716
aaaatcccta cgacctttcg                                               20

<210> SEQ ID NO 717
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 717 atttcccct tttctttcg                                                 20

<210> SEQ ID NO 718
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 718 ttttctttc gacaaaaccg                                                20

<210> SEQ ID NO 719
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 719 ttttctttc gacaaaaccg                                                20

<210> SEQ ID NO 720
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 720
gccatcgtca tcataacccg                                               20

<210> SEQ ID NO 721
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 721
gtcatcataa cccgttctcg                                               20

<210> SEQ ID NO 722

<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 722
tcgatatcac tatctcttcg                                               20

<210> SEQ ID NO 723
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 723
aacaaaacaa acacacaacg                                               20

<210> SEQ ID NO 724
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 724
taacaaaatt aaaatttacg                                               20

<210> SEQ ID NO 725
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 725
ttttaaatct atttaaaacg                                               20

<210> SEQ ID NO 726
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 726
caaaatataa ataaataacg                                               20

<210> SEQ ID NO 727
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 727
aaataacgaa acctcccacg                                               20

<210> SEQ ID NO 728
<211> LENGTH: 20

```
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 728
aacgaaacct cccacgatcg                                                 20

<210> SEQ ID NO 729
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 729
aacctcccac gatcgatccg                                                 20

<210> SEQ ID NO 730
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 730
gcaactttat aaaaaaaccg                                                 20

<210> SEQ ID NO 731
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 731
ttaaaataaa atttaaatcg                                                 20

<210> SEQ ID NO 732
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 732
ataatataaa ataacttacg                                                 20

<210> SEQ ID NO 733
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 733
ctaaactttc tattaaatcg                                                 20

<210> SEQ ID NO 734
<211> LENGTH: 20
<212> TYPE: DNA
```

-continued

<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 734
tttctattaa atcgctatcg                                              20

<210> SEQ ID NO 735
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 735
aacgatcata ataatttccg                                              20

<210> SEQ ID NO 736
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 736
cattattata acaaatctcg                                              20

<210> SEQ ID NO 737
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 737
cttctaaaac tatacctacg                                              20

<210> SEQ ID NO 738
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 738
ctaaaactat acctacgccg                                              20

<210> SEQ ID NO 739
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 739
acattatctc ctaataaacg                                              20

<210> SEQ ID NO 740
<211> LENGTH: 20
<212> TYPE: DNA
<213> ORGANISM: Artificial

<220> FEATURE:
<223> OTHER INFORMATION: COMPLEMENTARY primer specific for the
      bisulfite-converted METHYLATED SENSE strand of the HERV-K element

<400> SEQUENCE: 740
taactttcta aaataaccg                                                  20

<210> SEQ ID NO 741
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 741
ccgatactaa aattcgaccg                                                 20

<210> SEQ ID NO 742
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 742
ccgatactaa aattcgaccg                                                 20

<210> SEQ ID NO 743
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 743
cttattttct ctaacctacg                                                 20

<210> SEQ ID NO 744
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 744
ttcgcaatat aaaatttccg                                                 20

<210> SEQ ID NO 745
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 745 tatcaccta acttcttccg                                                  20

<210> SEQ ID NO 746
<211> LENGTH: 20
<212> TYPE: DNA
<213> ORGANISM: Artificial
<220> FEATURE:

```
<223> OTHER INFORMATION: COMPLEMENTARY primer specific for the
      bisulfite-converted METHYLATED SENSE strand of the HERV-K element

<400> SEQUENCE: 746
ccgaatacac aaacttaccg                                              20

<210> SEQ ID NO 747
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 747
actaactata aatatactcg                                              20

<210> SEQ ID NO 748
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 748
acttatcctc aataaccacg                                              20

<210> SEQ ID NO 749
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 749
atcctcaata accacgctcg                                              20

<210> SEQ ID NO 750
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 750
acacctataa atatttctcg                                              20

<210> SEQ ID NO 751
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED SENSE strand of the HERV-K element

<400> SEQUENCE: 751
aaaaacccga aaaccaacg                                               20

<210> SEQ ID NO 752
<211> LENGTH: 20
<212> TYPE: DNA
<213> ORGANISM: Artificial
<220> FEATURE:
<223> OTHER INFORMATION: COMPLEMENTARY primer specific for the
``` bisulfite-converted METHYLATED SENSE strand of the HERV-K element

<400> SEQUENCE: 752
aaaataaaca aacaaacacg                                          20

<210> SEQ ID NO 753
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 753
aaaaaaaata aaaaaaccca                                          20

<210> SEQ ID NO 754
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 754
aaaaacccaa aaaaccaaca                                          20

<210> SEQ ID NO 755
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 755
tcaacatata aaaaatccca                                          20

<210> SEQ ID NO 756
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 756
cattcataaa tatttctcca                                          20

<210> SEQ ID NO 757
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 757
aaaatcaaca aacaaacaca                                          20

<210> SEQ ID NO 758
<211> LENGTH: 20

```
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 758
aaacatctca atactttaca                                                    20

<210> SEQ ID NO 759
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 759
ataaataaaa tattcaatca                                                    20

<210> SEQ ID NO 760
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 760
aaaatcccta caacctttca                                                    20

<210> SEQ ID NO 761
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 761
atttccccct tttctttttca                                                   20

<210> SEQ ID NO 762
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 762
ttttcttttc aacaaaacca                                                    20

<210> SEQ ID NO 763
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 763
```
tttcaacaaa accaccatca                                          20

<210> SEQ ID NO 764
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 764
gccatcatca tcataaccca                                          20

<210> SEQ ID NO 765
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 765
gtcatcataa cccattctca                                          20

<210> SEQ ID NO 766
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 766
tcaatatcac tatctcttca                                          20

<210> SEQ ID NO 767
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 767
aacaaaacaa acacacaaca                                          20

<210> SEQ ID NO 768
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 768
taacaaaatt aaaatttaca                                          20

<210> SEQ ID NO 769
<211> LENGTH: 20
<212> TYPE: DNA
<213> ORGANISM: Artificial
<220> FEATURE:
<223> OTHER INFORMATION: COMPLEMENTARY primer specific for the -continued bisulfite-converted DEMETHYLATED SENSE strand of the HERV-K element

<400> SEQUENCE: 769
ttttaaatct atttaaaaca                                               20

<210> SEQ ID NO 770
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 770
caaaatataa ataaataaca                                               20

<210> SEQ ID NO 771
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 771
aaataacaaa acctcccaca                                               20

<210> SEQ ID NO 772
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 772
aacaaaacct cccacaatca                                               20

<210> SEQ ID NO 773
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 773
aacctcccac aatcaatcca                                               20

<210> SEQ ID NO 774
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 774
gcaactttat aaaaaaacca                                               20

<210> SEQ ID NO 775

```
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 775
ttaaaataaa atttaaatca                                              20

<210> SEQ ID NO 776
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 776
ataatataaa ataacttaca                                              20

<210> SEQ ID NO 777
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 777
ctaaactttc tattaaatca                                              20

<210> SEQ ID NO 778
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 778
tttctattaa atcactatca                                              20

<210> SEQ ID NO 779
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 779
aacaatcata ataatttcca                                              20

<210> SEQ ID NO 780
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 780
```
cttctaaaac tatacctaca                                              20

<210> SEQ ID NO 781
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 781
cttctaaaac tatacctaca                                              20

<210> SEQ ID NO 782
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 782
ctaaaactat acctacacca                                              20

<210> SEQ ID NO 783
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 783
acattatctc ctaataaaca                                              20

<210> SEQ ID NO 784
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 784
taactttcta aaaataacca                                              20

<210> SEQ ID NO 785
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 785
ataaccaata ctaaaattca                                              20

<210> SEQ ID NO 786
<211> LENGTH: 20
<212> TYPE: DNA
<213> ORGANISM: Artificial
<220> FEATURE:

<223> OTHER INFORMATION: COMPLEMENTARY primer specific for the
      bisulfite-converted DEMETHYLATED SENSE strand of the HERV-K
      element

<400> SEQUENCE: 786
ccaatactaa aattcaacca                                                      20

<210> SEQ ID NO 787
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 787
cttattttct ctaacctaca                                                      20

<210> SEQ ID NO 788
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 788
ttcacaatat aaaatttcca                                                      20

<210> SEQ ID NO 789
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 789
tatcacccta acttcttcca                                                      20

<210> SEQ ID NO 790
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 790
ccaaatacac aaacttacca                                                      20

<210> SEQ ID NO 791
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 791
actaactata aatatactca                                                      20

```
<210> SEQ ID NO 792
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 792
acttatcctc aataaccaca                                                   20

<210> SEQ ID NO 793
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 793
atcctcaata accacactca                                                   20

<210> SEQ ID NO 794
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 794
acacctataa atatttctca                                                   20

<210> SEQ ID NO 795
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 795
aaaaacccaa aaaaccaaca                                                   20

<210> SEQ ID NO 796
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED SENSE strand of the HERV-K
      element

<400> SEQUENCE: 796
aaaataaaca aacaaacaca                                                   20

<210> SEQ ID NO 797
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element
```

<400> SEQUENCE: 797
agaaagaaat aagggggttc					20

<210> SEQ ID NO 798
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 798 aggggttcg gggaattagc					20

<210> SEQ ID NO 799
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 799
tttagtatat ggaggatttc					20

<210> SEQ ID NO 800
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 800
ttagtattta ttgattattc					20

<210> SEQ ID NO 801
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 801
ttattcgtgg gtgttttttc					20

<210> SEQ ID NO 802
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 802
gagggttagt agataaatac					20

<210> SEQ ID NO 803
<211> LENGTH: 20
<212> TYPE: DNA
<213> ORGANISM: Artificial

```
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 803
taaatatttt aatgttttac                                              20

<210> SEQ ID NO 804
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 804
agtagatgga atgtttaatc                                              20

<210> SEQ ID NO 805
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 805
ttttagtata gattttttac                                              20

<210> SEQ ID NO 806
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 806
atagattttt tacgggtgtc                                              20

<210> SEQ ID NO 807
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 807
ttaggttttt tttttttac                                               20

<210> SEQ ID NO 808
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 808
ttttaggtag aggtttttgc                                              20
```

<210> SEQ ID NO 809
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 809
agaggttttt gcggtttttc                                                20

<210> SEQ ID NO 810
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 810
gtatatgttt tagagagtac                                                20

<210> SEQ ID NO 811
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 811 tattttttt ttttttttc                                                  20

<210> SEQ ID NO 812
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 812
tttttttttt cgataaaatc                                                20

<210> SEQ ID NO 813
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 813
ttttcgataa aatcgttatc                                                20

<210> SEQ ID NO 814
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element -continued

<400> SEQUENCE: 814
cgttatcgtt attatggttc                                           20

<210> SEQ ID NO 815
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 815
cgttattatg gttcgttttc                                           20

<210> SEQ ID NO 816
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 816
ttcgatgtta ttgtttttc                                            20

<210> SEQ ID NO 817
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 817
agataaaata ggtatataac                                           20

<210> SEQ ID NO 818
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 818
gtgatagggt taagatttgc                                           20

<210> SEQ ID NO 819
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 819
taatttttgt tatagtagtc                                           20

<210> SEQ ID NO 820
<211> LENGTH: 20
<212> TYPE: DNA

```
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 820
tttttggatt tatttaaaac                                              20

<210> SEQ ID NO 821
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 821
ttaaaatatg gatggatggc                                              20

<210> SEQ ID NO 822
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 822
tggatggcga ggtttttac                                               20

<210> SEQ ID NO 823
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 823
tggcgaggtt ttttacggtc                                              20

<210> SEQ ID NO 824
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 824
aggtttttta cggtcggttc                                              20

<210> SEQ ID NO 825
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 825
aggtttttta cggtcggttc                                              20
```

<210> SEQ ID NO 826
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 826
cgtaattttg taaaggaatc                                               20

<210> SEQ ID NO 827
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 827
gttagaatgg aatttaggtc                                               20

<210> SEQ ID NO 828
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 828
gatagtataa aatggtttac                                               20

<210> SEQ ID NO 829
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 829
ttatttgtgt atttggatac                                               20

<210> SEQ ID NO 830
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 830
attgtggtag aattgatttc                                               20

<210> SEQ ID NO 831
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K -continued element

<400> SEQUENCE: 831
gtttaattta taatagtttc                                            20

<210> SEQ ID NO 832
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 832
gttttgtaaa taatttattc                                            20

<210> SEQ ID NO 833
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 833
cgtggtttga gtgatatttc                                            20

<210> SEQ ID NO 834
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 834
tttaggtttg gtagggtagc                                            20

<210> SEQ ID NO 835
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 835
tgattggtgt tattattttc                                            20

<210> SEQ ID NO 836
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 836
gttattattt tcgtggaggc                                            20

<210> SEQ ID NO 837
<211> LENGTH: 20

<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 837
gtattatata tgtagaattc                                          20

<210> SEQ ID NO 838
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 838 agtattttt aaaggtttac                                          20

<210> SEQ ID NO 839
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 839
aggaatgttt agagttggtc                                          20

<210> SEQ ID NO 840
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 840
atggggttat ataatgtagc                                          20

<210> SEQ ID NO 841
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 841
ttattgttgt aataaatttc                                          20

<210> SEQ ID NO 842
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 842
atttttgagg ttgtgtttac                                          20

<210> SEQ ID NO 843
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 843
tttgaggttg tgtttacgtc                                          20

<210> SEQ ID NO 844
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 844
ttataagtat agttttatgc                                          20

<210> SEQ ID NO 845
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 845
tttttttttt aggtggtatc                                          20

<210> SEQ ID NO 846
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 846
taggtggtat cggttttaac                                          20

<210> SEQ ID NO 847
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 847
ttgatttttt gggggtggtc                                          20

<210> SEQ ID NO 848
<211> LENGTH: 20
<212> TYPE: DNA
<213> ORGANISM: Artificial
<220> FEATURE:
<223> OTHER INFORMATION: SEQUENCE-IDENTICAL primer specific for the bisulfite-converted METHYLATED ANTISENSE strand of the HERV-K
element

<400> SEQUENCE: 848
ggtggtcgat attgaagttc                                               20

<210> SEQ ID NO 849
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 849
gtcgatattg aagttcggtc                                               20

<210> SEQ ID NO 850
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 850
ttttattttt tttaatttgc                                               20

<210> SEQ ID NO 851
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 851
gtttgaggtt gtaatgttac                                               20

<210> SEQ ID NO 852
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 852
gcgttgattg agttattaac                                               20

<210> SEQ ID NO 853
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 853
ttgttatttt agttttttc                                                20

<210> SEQ ID NO 854

```
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 854
ttcgagtgta taagtttatc                                                    20

<210> SEQ ID NO 855
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 855
gatttgtttt taatgattac                                                    20

<210> SEQ ID NO 856
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 856
tgtttttaat gattacgttc                                                    20

<210> SEQ ID NO 857
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 857
tgtttttaat gattacgttc                                                    20

<210> SEQ ID NO 858
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 858
agaaagaaat aaggggttc                                                     20

<210> SEQ ID NO 859
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted METHYLATED ANTISENSE strand of the HERV-K
      element

<400> SEQUENCE: 859
``` aggggggttcg gggaattaac                                              20

<210> SEQ ID NO 860
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 860
agaaagaaat aaggggtttt                                               20

<210> SEQ ID NO 861
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 861 aggggggttct gggaattagt                                              20

<210> SEQ ID NO 862
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 862
tttagtatat ggaggatttt                                               20

<210> SEQ ID NO 863
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 863
ttagtattta ttgattattt                                               20

<210> SEQ ID NO 864
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 864
ttattcttgg gtgttttttt                                               20

<210> SEQ ID NO 865
<211> LENGTH: 20
<212> TYPE: DNA
<213> ORGANISM: Artificial
<220> FEATURE:

```
<223> OTHER INFORMATION: SEQUENCE-IDENTICAL primer specific for the
      bisulfite-converted DEMETHYLATED ANTISENSE strand of the HERV-K
      element

<400> SEQUENCE: 865
gagggttagt agataaatat                                              20

<210> SEQ ID NO 866
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 866
taaatatttt aatgttttat                                              20

<210> SEQ ID NO 867
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 867
agtagatgga atgtttaatt                                              20

<210> SEQ ID NO 868
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 868
ttttagtata gattttttat                                              20

<210> SEQ ID NO 869
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 869
atagattttt tactggtgtt                                              20

<210> SEQ ID NO 870
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 870
ttaggttttt tttttttat                                               20
```

```
<210> SEQ ID NO 871
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 871
ttttaggtag aggttttttgt                                              20

<210> SEQ ID NO 872
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 872
agaggttttt gctgttttt                                                20

<210> SEQ ID NO 873
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 873
gtatatgttt tagagagtat                                               20

<210> SEQ ID NO 874
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 874
tatttttttt tttttttttt                                               20

<210> SEQ ID NO 875
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 875
tttttttttt ctataaaatt                                               20

<210> SEQ ID NO 876
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element
```

<400> SEQUENCE: 876
ttttctataa aatctttatt                                          20

<210> SEQ ID NO 877
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 877
ctttatcttt attatggttt                                          20

<210> SEQ ID NO 878
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 878
ctttattatg gttctttttt                                          20

<210> SEQ ID NO 879
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 879
ttctatgtta ttgttttttt                                          20

<210> SEQ ID NO 880
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 880
agataaaata ggtatataat                                          20

<210> SEQ ID NO 881
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 881
gtgatagggt taagatttgt                                          20

<210> SEQ ID NO 882
<211> LENGTH: 20
<212> TYPE: DNA
<213> ORGANISM: Artificial

```
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 882
taatttttgt tatagtagtt                                              20

<210> SEQ ID NO 883
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 883
tttttggatt tatttaaaat                                              20

<210> SEQ ID NO 884
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 884
ttaaaatatg gatggatggt                                              20

<210> SEQ ID NO 885
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 885
tggatggcta ggttttttat                                              20

<210> SEQ ID NO 886
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 886
tggctaggtt ttttactgtt                                              20

<210> SEQ ID NO 887
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 887
aggtttttta ctgtctgttt                                              20
```

<210> SEQ ID NO 888
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 888
tgtttttatt agtagaatat                                          20

<210> SEQ ID NO 889
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 889
cttaattttg taaaggaatt                                          20

<210> SEQ ID NO 890
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 890
gttagaatgg aatttaggtt                                          20

<210> SEQ ID NO 891
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 891
gatagtataa aatggtttat                                          20

<210> SEQ ID NO 892
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 892
ttatttgtgt atttggatat                                          20

<210> SEQ ID NO 893
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

```
<400> SEQUENCE: 893
attgtggtag aattgatttt                                                   20

<210> SEQ ID NO 894
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 894
gtttaattta taatagtttt                                                   20

<210> SEQ ID NO 895
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 895
gttttgtaaa taatttattt                                                   20

<210> SEQ ID NO 896
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 896
cttggtttga gtgatatttt                                                   20

<210> SEQ ID NO 897
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 897
tttaggtttg gtagggtagt                                                   20

<210> SEQ ID NO 898
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 898
tgattggtgt tattatttt                                                    20

<210> SEQ ID NO 899
<211> LENGTH: 20
<212> TYPE: DNA
```

```
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 899
gttattattt tcttggaggt                                              20

<210> SEQ ID NO 900
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 900
gtattatata tgtagaattt                                              20

<210> SEQ ID NO 901
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 901
agtatttttt aaaggtttat                                              20

<210> SEQ ID NO 902
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 902
aggaatgttt agagttggtt                                              20

<210> SEQ ID NO 903
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 903
atggggttat ataatgtagt                                              20

<210> SEQ ID NO 904
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 904
ttattgttgt aataaatttt                                              20
```

<210> SEQ ID NO 905
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 905
atttttgagg ttgtgtttat                                          20

<210> SEQ ID NO 906
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 906
tttgaggttg tgtttacttt                                          20

<210> SEQ ID NO 907
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 907
ttataagtat agttttatgt                                          20

<210> SEQ ID NO 908
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 908
tttttttttt aggtggtatt                                          20

<210> SEQ ID NO 909
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 909
taggtggtat ctgttttaat                                          20

<210> SEQ ID NO 910
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K -continued

```
        element

<400> SEQUENCE: 910 ttgattttt ggggtggtt                                              20

<210> SEQ ID NO 911
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 911
ggtggtctat attgaagttt                                            20

<210> SEQ ID NO 912
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 912
gtctatattg aagttctgtt                                            20

<210> SEQ ID NO 913
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 913
ttttattttt tttaatttgt                                            20

<210> SEQ ID NO 914
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 914
gtttgaggtt gtaatgttat                                            20

<210> SEQ ID NO 915
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 915
gctttgattg agttattaat                                            20

<210> SEQ ID NO 916
<211> LENGTH: 20
```

<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 916
ttgttatttt agtttttttt                                              20

<210> SEQ ID NO 917
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 917
ttctagtgta taagtttatt                                              20

<210> SEQ ID NO 918
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 918
gatttgtttt taatgattat                                              20

<210> SEQ ID NO 919
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 919
tgtttttaat gattactttt                                              20

<210> SEQ ID NO 920
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 920
tatatttgtg ggtgtttttt                                              20

<210> SEQ ID NO 921
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 921
agaaagaaat aagggggttt                                          20

<210> SEQ ID NO 922
<211> LENGTH: 20
<212> TYPE: DNA
<213> ORGANISM: Artificial
<220> FEATURE:
<223> OTHER INFORMATION: SEQUENCE-IDENTICAL primer specific for the
      bisulfite-converted DEMETHYLATED ANTISENSE strand of the HERV-K
      element

<400> SEQUENCE: 922 aggggggttct gggaattaat                                         20

<210> SEQ ID NO 923
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 923
taaccttacc cccaaccccg                                          20

<210> SEQ ID NO 924
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 924
aattaaataa attaaaaacg                                          20

<210> SEQ ID NO 925
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 925
ccaaaaacac aaaaactacg                                          20

<210> SEQ ID NO 926
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 926
aaatctaaaa tataacctcg                                          20

<210> SEQ ID NO 927
<211> LENGTH: 20
<212> TYPE: DNA
<213> ORGANISM: Artificial
<220> FEATURE:
<223> OTHER INFORMATION: COMPLEMENTARY primer specific for the -continued bisulfite-converted METHYLATED ANTISENSE strand of the HERV-K
element

<400> SEQUENCE: 927
aaaaaaaaaa aacctaaccg                                                20

<210> SEQ ID NO 928
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 928
cctaaccgtc ccccaacccg                                                20

<210> SEQ ID NO 929
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 929
ctaaacaata aaatatctcg                                                20

<210> SEQ ID NO 930
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 930
atatctcgat ataaaacccg                                                20

<210> SEQ ID NO 931
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 931
atataaaacc cgattatacg                                                20

<210> SEQ ID NO 932
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 932
tacaaaaacc tttattcacg                                                20

<210> SEQ ID NO 933

```
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 933
ctctcaaaaa aacacccacg                                              20

<210> SEQ ID NO 934
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 934
aatcctccat atactaaacg                                              20

<210> SEQ ID NO 935
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 935
tactaaacgt taattccccg                                              20

<210> SEQ ID NO 936
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 936
atctctcatt acaccttacg                                              20

<210> SEQ ID NO 937
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 937
ccttcatcta atacccaacg                                              20

<210> SEQ ID NO 938
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 938
```
ctaaaataaa aatacactcg                                               20

<210> SEQ ID NO 939
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 939
aataaaaata cactcgaacg                                               20

<210> SEQ ID NO 940
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 940
taatcattaa aaacaaatcg                                               20

<210> SEQ ID NO 941
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 941
atttcaaaca aaaataacg                                                20

<210> SEQ ID NO 942
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 942
aaaaatccca aaaaaaaacg                                               20

<210> SEQ ID NO 943
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 943
aacgaaaact ttacattacg                                               20

<210> SEQ ID NO 944
<211> LENGTH: 20
<212> TYPE: DNA
<213> ORGANISM: Artificial
<220> FEATURE:

<223> OTHER INFORMATION: COMPLEMENTARY primer specific for the
     bisulfite-converted METHYLATED ANTISENSE strand of the HERV-K
     element

<400> SEQUENCE: 944
acgaatatat aacaaaaccg                                                   20

<210> SEQ ID NO 945
<211> LENGTH: 20
<212> TYPE: DNA
<213> ORGANISM: Artificial
<220> FEATURE:
<223> OTHER INFORMATION: COMPLEMENTARY primer specific for the
     bisulfite-converted METHYLATED ANTISENSE strand of the HERV-K
     element

<400> SEQUENCE: 945
cgttaataac tcaatcaacg                                                   20

<210> SEQ ID NO 946
<211> LENGTH: 20
<212> TYPE: DNA
<213> ORGANISM: Artificial
<220> FEATURE:
<223> OTHER INFORMATION: COMPLEMENTARY primer specific for the
     bisulfite-converted METHYLATED ANTISENSE strand of the HERV-K
     element

<400> SEQUENCE: 946
cgttaataac tcaatcaacg                                                   20

<210> SEQ ID NO 947
<211> LENGTH: 20
<212> TYPE: DNA
<213> ORGANISM: Artificial
<220> FEATURE:
<223> OTHER INFORMATION: COMPLEMENTARY primer specific for the
     bisulfite-converted METHYLATED ANTISENSE strand of the HERV-K
     element

<400> SEQUENCE: 947
ttcaacaaat caaataaccg                                                   20

<210> SEQ ID NO 948
<211> LENGTH: 20
<212> TYPE: DNA
<213> ORGANISM: Artificial
<220> FEATURE:
<223> OTHER INFORMATION: COMPLEMENTARY primer specific for the
     bisulfite-converted METHYLATED ANTISENSE strand of the HERV-K
     element

<400> SEQUENCE: 948
taacattaca acctcaaacg                                                   20

<210> SEQ ID NO 949
<211> LENGTH: 20
<212> TYPE: DNA
<213> ORGANISM: Artificial
<220> FEATURE:
<223> OTHER INFORMATION: COMPLEMENTARY primer specific for the
     bisulfite-converted METHYLATED ANTISENSE strand of the HERV-K
     element

<400> SEQUENCE: 949
cttatcaata ctaaccaccg                                                   20

<210> SEQ ID NO 950
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 950
tcaatactaa ccaccgaccg                                            20

<210> SEQ ID NO 951
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 951
ccgaccgaac ttcaatatcg                                            20

<210> SEQ ID NO 952
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 952
attaccaata aaaaaacccg                                            20

<210> SEQ ID NO 953
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 953
aataaaatta ataacatacg                                            20

<210> SEQ ID NO 954
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 954
attaataaca tacgaaaacg                                            20

<210> SEQ ID NO 955
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

```
<400> SEQUENCE: 955
tcaaaatata taaaaacccg                                              20

<210> SEQ ID NO 956
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 956
ataaaattaa aaaaactacg                                              20

<210> SEQ ID NO 957
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 957
aaaataaaca accattatcg                                              20

<210> SEQ ID NO 958
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 958
ctaatcttaa aaaaatcacg                                              20

<210> SEQ ID NO 959
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 959
aatttaaaaa cactaatccg                                              20

<210> SEQ ID NO 960
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 960
aactattaca aaacttatcg                                              20

<210> SEQ ID NO 961
<211> LENGTH: 20
<212> TYPE: DNA
<213> ORGANISM: Artificial
```

```
<220> FEATURE:
<223> OTHER INFORMATION: COMPLEMENTARY primer specific for the
      bisulfite-converted METHYLATED ANTISENSE strand of the HERV-K
      element

<400> SEQUENCE: 961
tattacaaaa cttatcgacg                                              20

<210> SEQ ID NO 962
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 962
tattacaaca ataaaatacg                                              20

<210> SEQ ID NO 963
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 963
aaaaatatta attaaattcg                                              20

<210> SEQ ID NO 964
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 964
attaatccga caaaattacg                                              20

<210> SEQ ID NO 965
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 965
tcaaaactcc atatcaatcg                                              20

<210> SEQ ID NO 966
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 966
caaaaaaaaa cgcctccacg                                              20
```

<210> SEQ ID NO 967
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 967
gaaatatcac tcaaaccacg                                              20

<210> SEQ ID NO 968
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 968
attataaatt aaacacctcg                                              20

<210> SEQ ID NO 969
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 969
actcaaaaca aactcaatcg                                              20

<210> SEQ ID NO 970
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 970
acaaataaat ccaactatcg                                              20

<210> SEQ ID NO 971
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 971
aaatccaact atcgataacg                                              20

<210> SEQ ID NO 972
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 972
actttaaaaa caaaatatcg                                          20

<210> SEQ ID NO 973
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 973
taaaccattt tatactatcg                                          20

<210> SEQ ID NO 974
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 974
acctaaattc cattctaacg                                          20

<210> SEQ ID NO 975
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 975
tataaatccc tatatccacg                                          20

<210> SEQ ID NO 976
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 976
atccctatat ccacgaaccg                                          20

<210> SEQ ID NO 977
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 977
ctatatccac gaaccgaccg                                          20

<210> SEQ ID NO 978
<211> LENGTH: 20
<212> TYPE: DNA

```
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 978
accgaccgta aaaaacctcg                                                    20

<210> SEQ ID NO 979
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 979
cactaaaaca taattaaacg                                                    20

<210> SEQ ID NO 980
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 980
aaaaattact aataacctcg                                                    20

<210> SEQ ID NO 981
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 981
ccgaaaaaac aataacatcg                                                    20

<210> SEQ ID NO 982
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 982
aaacaataac atcgaaaacg                                                    20

<210> SEQ ID NO 983
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 983
gaaaacgaac cataataacg                                                    20
```

<210> SEQ ID NO 984
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 984
gaaccataat aacgataacg                                              20

<210> SEQ ID NO 985
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted METHYLATED ANTISENSE strand of the HERV-K
      element

<400> SEQUENCE: 985
taacgataac gattttatcg                                              20

<210> SEQ ID NO 986
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 986
taaccttacc cccaacccca                                              20

<210> SEQ ID NO 987
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 987
aattaaataa attaaaaaca                                              20

<210> SEQ ID NO 988
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 988
ccaaaaacac aaaaactaca                                              20

<210> SEQ ID NO 989
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K element

<400> SEQUENCE: 989
aaatctaaaa tataacctca                                           20

<210> SEQ ID NO 990
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 990
aaaaaaaaaa aacctaacca                                           20

<210> SEQ ID NO 991
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 991
cctaaccatc ccccaaccca                                           20

<210> SEQ ID NO 992
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 992
ctaaacaata aaatatctca                                           20

<210> SEQ ID NO 993
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 993
atatctcaat ataaaaccca                                           20

<210> SEQ ID NO 994
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 994
atataaaacc caattataca                                           20

<210> SEQ ID NO 995
<211> LENGTH: 20

```
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 995
tacaaaaacc tttattcaca                                               20

<210> SEQ ID NO 996
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 996
ctctcaaaaa aacacccaca                                               20

<210> SEQ ID NO 997
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 997
aatcctccat atactaaaca                                               20

<210> SEQ ID NO 998
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 998
tactaaacat taattcccca                                               20

<210> SEQ ID NO 999
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 999
atctctcatt acaccttaca                                               20

<210> SEQ ID NO 1000
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1000
```
ccttcatcta atacccaaca                                                20

<210> SEQ ID NO 1001
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1001
ctaaaataaa aatacactca                                                20

<210> SEQ ID NO 1002
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1002
aataaaaata cactcaaaca                                                20

<210> SEQ ID NO 1003
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1003
taatcattaa aaacaaatca                                                20

<210> SEQ ID NO 1004
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1004
atttcaaaca aaaataaca                                                 20

<210> SEQ ID NO 1005
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1005
aaaaatccca aaaaaaaaca                                                20

<210> SEQ ID NO 1006
<211> LENGTH: 20
<212> TYPE: DNA
<213> ORGANISM: Artificial
<220> FEATURE:
<223> OTHER INFORMATION: COMPLEMENTARY primer specific for the bisulfite-converted DEMETHYLATED ANTISENSE strand of the HERV-K
element

<400> SEQUENCE: 1006
aacaaaaact ttacattaca                                        20

<210> SEQ ID NO 1007
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1007
acaaatatat aacaaaacca                                        20

<210> SEQ ID NO 1008
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1008
cattaataac tcaatcaaca                                        20

<210> SEQ ID NO 1009
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1009
ccattaaaat ctaaaccaca                                        20

<210> SEQ ID NO 1010
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1010
ttcaacaaat caaataacca                                        20

<210> SEQ ID NO 1011
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1011
taacattaca acctcaaaca                                        20

<210> SEQ ID NO 1012

```
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1012
cttatcaata ctaaccacca                                              20

<210> SEQ ID NO 1013
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1013
tcaatactaa ccaccaacca                                              20

<210> SEQ ID NO 1014
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1014
ccaaccaaac ttcaatatca                                              20

<210> SEQ ID NO 1015
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1015
attaccaata aaaaaaccca                                              20

<210> SEQ ID NO 1016
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1016
aataaaatta ataacataca                                              20

<210> SEQ ID NO 1017
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1017
```
attaataaca tacaaaaaca                                          20

<210> SEQ ID NO 1018
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1018
tcaaaatata taaaaaccca                                          20

<210> SEQ ID NO 1019
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1019
ataaaattaa aaaaactaca                                          20

<210> SEQ ID NO 1020
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1020
aaaataaaca accattatca                                          20

<210> SEQ ID NO 1021
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1021
ctaatcttaa aaaaatcaca                                          20

<210> SEQ ID NO 1022
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1022
aatttaaaaa cactaatcca                                          20

<210> SEQ ID NO 1023
<211> LENGTH: 20
<212> TYPE: DNA
<213> ORGANISM: Artificial
<220> FEATURE:

```
<223> OTHER INFORMATION: COMPLEMENTARY primer specific for the
      bisulfite-converted DEMETHYLATED ANTISENSE strand of the HERV-K
      element

<400> SEQUENCE: 1023
aactattaca aaacttatca                                              20

<210> SEQ ID NO 1024
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1024
tattacaaaa cttatcaaca                                              20

<210> SEQ ID NO 1025
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1025
tattacaaca ataaaataca                                              20

<210> SEQ ID NO 1026
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1026
aaaaatatta attaaattca                                              20

<210> SEQ ID NO 1027
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1027
attaatccaa caaaattaca                                              20

<210> SEQ ID NO 1028
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1028
tcaaaactcc atatcaatca                                              20
```

<210> SEQ ID NO 1029
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1029
caaaaaaaaa cacctccaca                                               20

<210> SEQ ID NO 1030
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1030
gaaatatcac tcaaaccaca                                               20

<210> SEQ ID NO 1031
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1031
attataaatt aaacacctca                                               20

<210> SEQ ID NO 1032
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1032
actcaaaaca aactcaatca                                               20

<210> SEQ ID NO 1033
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1033
acaaataaat ccaactatca                                               20

<210> SEQ ID NO 1034
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1034
aaatccaact atcaataaca                                             20

<210> SEQ ID NO 1035
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1035
actttaaaaa caaaatatca                                             20

<210> SEQ ID NO 1036
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1036
taaaccattt tatactatca                                             20

<210> SEQ ID NO 1037
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1037
acctaaattc cattctaaca                                             20

<210> SEQ ID NO 1038
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1038
tataaatccc tatatccaca                                             20

<210> SEQ ID NO 1039
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1039
atccctatat ccacaaacca                                             20

<210> SEQ ID NO 1040
<211> LENGTH: 20
<212> TYPE: DNA
<213> ORGANISM: Artificial

```
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1040
ctatatccac aaaccaacca                                              20

<210> SEQ ID NO 1041
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1041
accaaccata aaaaacctca                                              20

<210> SEQ ID NO 1042
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1042
cactaaaaca taattaaaca                                              20

<210> SEQ ID NO 1043
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1043
aaaaattact aataacctca                                              20

<210> SEQ ID NO 1044
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1044
ccaaaaaaac aataacatca                                              20

<210> SEQ ID NO 1045
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1045
aaacaataac atcaaaaaca                                              20
```

<210> SEQ ID NO 1046
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1046
gaaaacaaac cataataaca                                           20

<210> SEQ ID NO 1047
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1047
gaaccataat aacaataaca                                           20

<210> SEQ ID NO 1048
<211> LENGTH: 20
<212> TYPE: DNA
<213> ORGANISM: Artificial
<220> FEATURE:
<223> OTHER INFORMATION: COMPLEMENTARY primer specific for the
      bisulfite-converted DEMETHYLATED ANTISENSE strand of the HERV-K
      element

<400> SEQUENCE: 1048
taacaataac aattttatca                                           20

<210> SEQ ID NO 1049
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1049
gtgatttttg tattttattt                                           20

<210> SEQ ID NO 1050
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1050
ggtttatttt attagggagt                                           20

<210> SEQ ID NO 1051
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

```
<400> SEQUENCE: 1051
agggagtgtt agatagtggg                                              20

<210> SEQ ID NO 1052
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1052
aggtattgtt ttatttggga                                              20

<210> SEQ ID NO 1053
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1053
taaggggtta gggagttttt                                              20

<210> SEQ ID NO 1054
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1054
tttttgagtt aaagaaaggg                                              20

<210> SEQ ID NO 1055
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1055
agattatatt ttatatttgg                                              20

<210> SEQ ID NO 1056
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1056
ttgattgtta gtatagtagt                                              20

<210> SEQ ID NO 1057
<211> LENGTH: 20
<212> TYPE: DNA
```

```
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1057
tttgagatta aattgtaagg                                          20

<210> SEQ ID NO 1058
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1058
ttattgttta ggtttgttta                                          20

<210> SEQ ID NO 1059
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1059
gtttaggtaa ataaagtagt                                          20

<210> SEQ ID NO 1060
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1060
aattgggtgg agtttattat                                          20

<210> SEQ ID NO 1061
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1061
tagtttaagg aggtttgttt                                          20

<210> SEQ ID NO 1062
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1062
gtttttgtag gttttatttt                                          20
```

<210> SEQ ID NO 1063
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1063
tgggggtagg gtatagataa                                              20

<210> SEQ ID NO 1064
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1064
ataaaaagat agtagtaatt                                              20

<210> SEQ ID NO 1065
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1065
tttgtagatt taagtgtttt                                              20

<210> SEQ ID NO 1066
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1066
tgtttgatag ttttgaagag                                              20

<210> SEQ ID NO 1067
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1067
gagtagtggt tttttagta                                               20

<210> SEQ ID NO 1068
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the -continued promoter region of the LINE-1 element

<400> SEQUENCE: 1068
ggtagataga ttgttttttt                                              20

<210> SEQ ID NO 1069
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1069
aagtgggttt ttgatttttg                                              20

<210> SEQ ID NO 1070
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1070
attttcgagt agtttaattg                                              20

<210> SEQ ID NO 1071
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1071
ggaggtattt tttagtaggg                                              20

<210> SEQ ID NO 1072
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1072
gtagggtatt ttaatagatt                                              20

<210> SEQ ID NO 1073
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1073
gtagggtatt ttaatagatt                                              20

<210> SEQ ID NO 1074
<211> LENGTH: 20

```
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1074
tgtagttgag ggttttgttt                                              20

<210> SEQ ID NO 1075
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1075
ttagaaggaa aattaataat                                              20

<210> SEQ ID NO 1076
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1076
attagaaagg atatttatat                                              20

<210> SEQ ID NO 1077
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1077
aaaatttatt tgtatattat                                              20

<210> SEQ ID NO 1078
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1078
tattattaaa gattaaaagt                                              20

<210> SEQ ID NO 1079
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1079
```
agataaaatt ataaagatgg    20

<210> SEQ ID NO 1080
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1080
ggaaaaaata gaatagaaaa    20

<210> SEQ ID NO 1081
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1081
aaaaattgga aattttaaaa    20

<210> SEQ ID NO 1082
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1082
tttttttttt tttaaaggaa    20

<210> SEQ ID NO 1083
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1083 tagttttta ttagtaatag    20

<210> SEQ ID NO 1084
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1084
aataaagttg gatggagaat    20

<210> SEQ ID NO 1085
<211> LENGTH: 20
<212> TYPE: DNA
<213> ORGANISM: Artificial
<220> FEATURE:
<223> OTHER INFORMATION: Sequence-identical and complementary primer sequence specific for the bisulfite-converted sense strand of the
promoter region of the LINE-1 element

<400> SEQUENCE: 1085
agttgagaga agaaggtttt                                           20

<210> SEQ ID NO 1086
<211> LENGTH: 20
<212> TYPE: DNA
<213> ORGANISM: Artificial
<220> FEATURE:
<223> OTHER INFORMATION: Sequence-identical and complementary primer
      sequence specific for
      the bisulfite-converted sense strand of the promoter region of
      the LINE-1 element

<400> SEQUENCE: 1086
agacgattaa attattttga                                           20

<210> SEQ ID NO 1087
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1087
ggaggatatt taaattaaag                                           20

<210> SEQ ID NO 1088
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1088
gtaaagaagt tgaaaatttt                                           20

<210> SEQ ID NO 1089
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1089
tgaaaaaaat ttagaagaat                                           20

<210> SEQ ID NO 1090
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1090
gtataattag aataattaat                                           20

```
<210> SEQ ID NO 1091
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1091
atagagaagt gtttaaagga                                              20

<210> SEQ ID NO 1092
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1092
gttgatggag ttgaaaatta                                              20

<210> SEQ ID NO 1093
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1093
tgaagaatgt agaagtttta                                              20

<210> SEQ ID NO 1094
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1094
attaattgga agaaagggta                                              20

<210> SEQ ID NO 1095
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1095
ttagtaatgg aagatgaaat                                              20

<210> SEQ ID NO 1096
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element
```

<400> SEQUENCE: 1096
agaagggaag tttagagaaa                                          20

<210> SEQ ID NO 1097
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1097
ctctatattt cctaaatcta                                          20

<210> SEQ ID NO 1098
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1098
ttaacctacc ttactaaatt                                          20

<210> SEQ ID NO 1099
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of
      the LINE-1 element

<400> SEQUENCE: 1099
taaataatat cctacaaaat                                          20

<210> SEQ ID NO 1100
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1100
cacatcactt tcaaatacac                                          20

<210> SEQ ID NO 1101
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1101
atttaatctt ttcacataat                                          20

<210> SEQ ID NO 1102
<211> LENGTH: 20
<212> TYPE: DNA

```
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1102
cttaaaaact ttactcattt                                              20

<210> SEQ ID NO 1103
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1103
ttattctttt ttctctaaac                                              20

<210> SEQ ID NO 1104
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1104
ttcatttcat tcatttcatc                                              20

<210> SEQ ID NO 1105
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1105
ataccctttc ttccaattaa                                              20

<210> SEQ ID NO 1106
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1106
cctaaaactt ctacattctt                                              20

<210> SEQ ID NO 1107
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1107
attttcaact ccatcaactc                                              20
```

```
<210> SEQ ID NO 1108
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1108
ttattctaat tatacattct                                            20

<210> SEQ ID NO 1109
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1109
aaaattttca acttctttac                                            20

<210> SEQ ID NO 1110
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1110
gtaactcaaa ataatttaat                                            20

<210> SEQ ID NO 1111
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1111
aaaaccttct tctctcaact                                            20

<210> SEQ ID NO 1112
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1112
gtcaaaatca ttctccatcc                                            20

<210> SEQ ID NO 1113
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
``` promoter region of the LINE-1 element

<400> SEQUENCE: 1113
attctattac taataaaaaa                                             20

<210> SEQ ID NO 1114
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1114
gttcctttaa aaaaaaaaa                                              20

<210> SEQ ID NO 1115
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1115
tttaaaattt ccaatttttc                                             20

<210> SEQ ID NO 1116
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1116
cccatcttta taattttatc                                             20

<210> SEQ ID NO 1117
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1117
taatctttaa taataataat                                             20

<210> SEQ ID NO 1118
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1118
taaatatcct ttctaattat                                             20

<210> SEQ ID NO 1119
<211> LENGTH: 20

```
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1119
caaacaaaac cctcaactac                                                  20

<210> SEQ ID NO 1120
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1120
gtataaaata tcaatatacc                                                  20

<210> SEQ ID NO 1121
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1121
aaatacctcc caattaaact                                                  20

<210> SEQ ID NO 1122
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1122
aaaatcaaaa acccacttaa                                                  20

<210> SEQ ID NO 1123
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1123
aaaaaaacaa tctatctacc                                                  20

<210> SEQ ID NO 1124
<211> LENGTH: 19
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1124
```

```
gttctcaaat ctccaacta                                                19
```

<210> SEQ ID NO 1125
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1125

```
actaaaaaaa ccactactct                                               20
```

<210> SEQ ID NO 1126
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1126

```
aaacaaaaac acttaaatct                                               20
```

<210> SEQ ID NO 1127
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1127

```
attactacta tcttttttatt                                              20
```

<210> SEQ ID NO 1128
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1128

```
ccccaaaaat aaaacctaca                                               20
```

<210> SEQ ID NO 1129
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1129

```
caaacctcct taaactataa                                               20
```

<210> SEQ ID NO 1130
<211> LENGTH: 20
<212> TYPE: DNA
<213> ORGANISM: Artificial
<220> FEATURE:
<223> OTHER INFORMATION: Sequence-identical and complementary primer sequence specific for the bisulfite-converted sense strand of the
promoter region of the LINE-1 element

<400> SEQUENCE: 1130
tttacctaaa caaacctaaa                                               20

<210> SEQ ID NO 1131
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1131
caatttaatc tcaaactact                                               20

<210> SEQ ID NO 1132
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1132
ccaaatataa aatataatct                                               20

<210> SEQ ID NO 1133
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1133 caccccttc tttaactcaa                                                20

<210> SEQ ID NO 1134
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1134
aaaaactccc taacccctta                                               20

<210> SEQ ID NO 1135
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1135
tcccaaataa aacaataacct                                              20

<210> SEQ ID NO 1136

```
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1136
tctaacactc cctaataaaa                                              20

<210> SEQ ID NO 1137
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1137
acctcaaata aaaatacaaa                                              20

<210> SEQ ID NO 1138
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1138
accatcttaa ctcctccccc                                              20

<210> SEQ ID NO 1139
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1139
cactaaaaca taattaaaca                                              20

<210> SEQ ID NO 1140
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1140
aaaaattact aataacctca                                              20

<210> SEQ ID NO 1141
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1141
```
ccaaaaaaac aataacatca                                              20

<210> SEQ ID NO 1142
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1142
aaacaataac atcaaaaaca                                              20

<210> SEQ ID NO 1143
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1143
gaaaacaaac cataataaca                                              20

<210> SEQ ID NO 1144
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1144
gaaccataat aacaataaca                                              20

<210> SEQ ID NO 1145
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      promoter region of the LINE-1 element

<400> SEQUENCE: 1145
taacaataac aattttatca                                              20

<210> SEQ ID NO 1146
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1146
aattttgttg atttttttaa                                              20

<210> SEQ ID NO 1147
<211> LENGTH: 20
<212> TYPE: DNA
<213> ORGANISM: Artificial
<220> FEATURE:

```
<223> OTHER INFORMATION: Sequence-identical and complementary primer
      sequence specific for the bisulfite-converted antisense strand of
      the promoter region of the LINE-1 element

<400> SEQUENCE: 1147 gtgttttat ttttttagt                                                   20

<210> SEQ ID NO 1148
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1148
aatgtgtttg ttttttgtttt                                                20

<210> SEQ ID NO 1149
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1149
taattttgga ttttttttgt                                                 20

<210> SEQ ID NO 1150
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1150
tttttttata tattgttttg                                                 20

<210> SEQ ID NO 1151
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1151
gtatgtggtg tttttgtttt                                                 20

<210> SEQ ID NO 1152
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1152 atattttat ttttgttttt                                                  20
```

-continued

<210> SEQ ID NO 1153
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1153
aggttgttta gtttttatgt                                              20

<210> SEQ ID NO 1154
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1154
tgtattgtgg tttgagagat                                              20

<210> SEQ ID NO 1155
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1155
attatgtggt taattttgga                                              20

<210> SEQ ID NO 1156
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1156
gatttggggt ggagagtttt                                              20

<210> SEQ ID NO 1157
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1157
tttttgggta tttttgttga                                              20

<210> SEQ ID NO 1158
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1158
tgttaaagtt ttttattatt                                               20

<210> SEQ ID NO 1159
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1159
gttttatgaa tttgggtgtt                                               20

<210> SEQ ID NO 1160
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1160
tgttgaattg atttttttat                                               20

<210> SEQ ID NO 1161
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1161
tgttgaattg atttttttat                                               20

<210> SEQ ID NO 1162
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1162
gtatattgat gggttttgat                                               20

<210> SEQ ID NO 1163
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1163
gtatattgat gggttttgat                                               20

<210> SEQ ID NO 1164
<211> LENGTH: 20
<212> TYPE: DNA
<213> ORGANISM: Artificial

```
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1164 tttttttaatt gtagaattta                                              20

<210> SEQ ID NO 1165
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1165
tttgtttatt agttgatgta                                               20

<210> SEQ ID NO 1166
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1166
ttatattttg gtatgattttt                                              20

<210> SEQ ID NO 1167
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1167
gtgttttttt taggagtttt                                               20

<210> SEQ ID NO 1168
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1168
aaagtatttt atttttttttt                                              20

<210> SEQ ID NO 1169
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1169
aaatttgggg ttgaaaattt                                               20
```

<210> SEQ ID NO 1170
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1170
ggttgttttt aatattttt                                              20

<210> SEQ ID NO 1171
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1171
ataattatgt gttttggagt                                              20

<210> SEQ ID NO 1172
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1172
gttttatttt ttatattatt                                              20

<210> SEQ ID NO 1173
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1173
atatagtttt atatttttg                                               20

<210> SEQ ID NO 1174
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1174
ttgatatttt tttttttagt                                              20

<210> SEQ ID NO 1175
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

```
<400> SEQUENCE: 1175
tttgaggttt ttgtattttt                                                   20

<210> SEQ ID NO 1176
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1176
attagttttt ttaagtattt                                                   20

<210> SEQ ID NO 1177
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1177
ttttaatttt tttgttttttg                                                  20

<210> SEQ ID NO 1178
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1178 gaagttttttt tttttttagtt                                                 20

<210> SEQ ID NO 1179
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1179
tgttttgttg ttggtgagga                                                   20

<210> SEQ ID NO 1180
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1180
tgatggtgat gtatagatgg                                                   20

<210> SEQ ID NO 1181
<211> LENGTH: 20
<212> TYPE: DNA
```

```
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1181
ttttagttgt aggtttgttg                                                   20

<210> SEQ ID NO 1182
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1182
agtgtgtttt tgttgggggg                                                   20

<210> SEQ ID NO 1183
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1183
tttatttgag gaggtagttt                                                   20

<210> SEQ ID NO 1184
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1184
gttgttagat agggatattt                                                   20

<210> SEQ ID NO 1185
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1185
ttgtgttttg tttttagagg                                                   20

<210> SEQ ID NO 1186
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1186
agttgtggtg ggttttattt                                                   20
```

```
<210> SEQ ID NO 1187
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1187
ttaagtaagt ttgggtaatg                                           20

<210> SEQ ID NO 1188
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1188
ttgattttag attgttgtgt                                           20

<210> SEQ ID NO 1189
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1189
ttaggtgtgg gatatagttt                                           20

<210> SEQ ID NO 1190
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1190
tttttttgat ttagaaaggg                                           20

<210> SEQ ID NO 1191
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1191
ttggtatttt ttagtgagat                                           20

<210> SEQ ID NO 1192
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
``` the promoter region of the LINE-1 element

<400> SEQUENCE: 1192
tagatggaaa tgtagaaatt                                           20

<210> SEQ ID NO 1193
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1193
tctacatttc catctaaaat                                           20

<210> SEQ ID NO 1194
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1194
taaaaaatac caaacaataa                                           20

<210> SEQ ID NO 1195
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1195 aaattcccett tctaaatcaa                                          20

<210> SEQ ID NO 1196
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1196
actatatccc acacctaact                                           20

<210> SEQ ID NO 1197
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1197
acaacaatct aaaatcaaac                                           20

<210> SEQ ID NO 1198
<211> LENGTH: 20

```
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1198
aacttactta aataaacaaa                                                20

<210> SEQ ID NO 1199
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1199
caccacaact caaaaaaacc                                                20

<210> SEQ ID NO 1200
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1200
ctaaaaacaa aacacaaaca                                                20

<210> SEQ ID NO 1201
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1201
aacttaaata tccctatcta                                                20

<210> SEQ ID NO 1202
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1202
aaaaaaacaa taattctccc                                                20

<210> SEQ ID NO 1203
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1203
```
caaataaatc cctaactcct                                              20

<210> SEQ ID NO 1204
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1204
ccaacaaaaa cacactaaca                                              20

<210> SEQ ID NO 1205
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1205
taaaaatcct atctattaaa                                              20

<210> SEQ ID NO 1206
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1206
aaaaaccaaa aataaataaa                                              20

<210> SEQ ID NO 1207
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1207
aacaaaacaa aactaaataa                                              20

<210> SEQ ID NO 1208
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1208
taaaaaaaaa aaacttcaaa                                              20

<210> SEQ ID NO 1209
<211> LENGTH: 20
<212> TYPE: DNA
<213> ORGANISM: Artificial
<220> FEATURE:
<223> OTHER INFORMATION: Sequence-identical and complementary primer sequence specific for the bisulfite-converted antisense strand of
      the promoter region of the LINE-1 element

<400> SEQUENCE: 1209
aaccaaaaac aaaaaaatta                                              20

<210> SEQ ID NO 1210
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1210
tataactaaa ataaccaata                                              20

<210> SEQ ID NO 1211
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1211
aataaaacta aaaccaaaa                                               20

<210> SEQ ID NO 1212
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1212
aatacaaaaa cctcaaaaac                                              20

<210> SEQ ID NO 1213
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1213
caacaataaa aataaaata                                               20

<210> SEQ ID NO 1214
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1214
aaaaaaaaaa aaataaaaaa                                              20

<210> SEQ ID NO 1215

```
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1215
aaaatataaa actatataaa                                              20

<210> SEQ ID NO 1216
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1216
taaaaataat ataaaaaata                                              20

<210> SEQ ID NO 1217
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1217
tacaaaatat tatccaaaaa                                              20

<210> SEQ ID NO 1218
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1218
aattcaaaaa atacaaaaaa                                              20

<210> SEQ ID NO 1219
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1219
aattcaccaa aattaaaata                                              20

<210> SEQ ID NO 1220
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1220
```
aaaacccatc aaactaacaa                                              20

<210> SEQ ID NO 1221
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1221
aaaaaaaata aaaaccaata                                              20

<210> SEQ ID NO 1222
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1222
aaccaaacta aacttcataa                                              20

<210> SEQ ID NO 1223
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1223
aaatattaaa aaattttatc                                              20

<210> SEQ ID NO 1224
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1224
acactaaaca taaaaaaaaa                                              20

<210> SEQ ID NO 1225
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1225
atcataccaa aatataaaaa                                              20

<210> SEQ ID NO 1226
<211> LENGTH: 20
<212> TYPE: DNA
<213> ORGANISM: Artificial
<220> FEATURE:

-continued

<223> OTHER INFORMATION: Sequence-identical and complementary primer
      sequence specific for the bisulfite-converted antisense strand of
      the promoter region of the LINE-1 element

<400> SEQUENCE: 1226
atcaactaat aaacaaaatc                                               20

<210> SEQ ID NO 1227
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the promoter region of the LINE-1 element

<400> SEQUENCE: 1227
caaaatcaaa ttcacacata                                               20

<210> SEQ ID NO 1228
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1228
gtttgtaatt ttagtattt                                                20

<210> SEQ ID NO 1229
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1229
attttagtat tttgggaggt                                               20

<210> SEQ ID NO 1230
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1230
ggattatttg aggttaggag                                               20

<210> SEQ ID NO 1231
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1231
gagattattt tggttaatat                                               20

<210> SEQ ID NO 1232
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1232
tggttaatat ggtgaaattt                                              20

<210> SEQ ID NO 1233
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1233
gtttttatta aaatataaa                                               20

<210> SEQ ID NO 1234
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1234
ttaaaaatat aaaaattagt                                              20

<210> SEQ ID NO 1235
<211> LENGTH: 19
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1235
gtttgtaatt ttagttatt                                               19

<210> SEQ ID NO 1236
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1236
gggaggttga ggtaggagaa                                              20

<210> SEQ ID NO 1237
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1237
gttattgtat tttagtttgg				20

<210> SEQ ID NO 1238
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1238
cccaaactaa aatacaataa				20

<210> SEQ ID NO 1239
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1239
attctcctac ctcaacctcc				20

<210> SEQ ID NO 1240
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1240
ttttatattt ttaataaaaa				20

<210> SEQ ID NO 1241
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1241
catattaacc aaaataatct				20

<210> SEQ ID NO 1242
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      alu element

<400> SEQUENCE: 1242
tctcctaacc tcaaataatc				20

<210> SEQ ID NO 1243
<211> LENGTH: 20
<212> TYPE: DNA
<213> ORGANISM: Artificial

```
<220> FEATURE:
<223> OTHER INFORMATION: Sequence-identical and complementary primer
      sequence specific for the bisulfite-converted sense strand of the
      alu element

<400> SEQUENCE: 1243
caaaatacta aaattacaaa                                              20

<210> SEQ ID NO 1244
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1244
tttaggttgg agtgtagtgg                                              20

<210> SEQ ID NO 1245
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1245 attttttttgt tttagttttt                                             20

<210> SEQ ID NO 1246
<211> LENGTH: 19
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1246
gagtagttgg gattatagg                                               19

<210> SEQ ID NO 1247
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1247
tttttgtatt tttagtagag                                              20

<210> SEQ ID NO 1248
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1248
ttttattatg ttggttagga                                              20
```

<210> SEQ ID NO 1249
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1249
attttttgat tttaggtgat                                              20

<210> SEQ ID NO 1250
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1250
tttttaaagt gttgggatta                                              20

<210> SEQ ID NO 1251
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1251
atcccaacac tttaaaaaac                                              20

<210> SEQ ID NO 1252
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1252
aatcacctaa aatcaaaaaa                                              20

<210> SEQ ID NO 1253
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1253
tcctaaccaa cataataaaa                                              20

<210> SEQ ID NO 1254
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1254
tactaaaaat acaaaaatta                                               20

<210> SEQ ID NO 1255
<211> LENGTH: 19
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1255
gcctataatc ccaactact                                                19

<210> SEQ ID NO 1256
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1256
gaaaaactaa aacaaaaaaa                                               20

<210> SEQ ID NO 1257
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the alu element

<400> SEQUENCE: 1257
ccactacact ccaacctaaa                                               20

<210> SEQ ID NO 1258
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1258
gtagttgaga taagaggaag                                               20

<210> SEQ ID NO 1259
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1259
agggagaaat tattttaggg                                               20

<210> SEQ ID NO 1260
<211> LENGTH: 20
<212> TYPE: DNA

```
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1260
taaagtattg agatgtttat                                                    20

<210> SEQ ID NO 1261
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1261
atatattttt tttttagaga                                                    20

<210> SEQ ID NO 1262
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1262
gaaatattta taggtgtgga                                                    20

<210> SEQ ID NO 1263
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1263
ggggtaaatt aaaattaaaa                                                    20

<210> SEQ ID NO 1264
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1264
atagaataat tttgtttatg                                                    20

<210> SEQ ID NO 1265
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1265
agtaggtagg aagggtaata                                                    20
```

```
<210> SEQ ID NO 1266
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1266
gttttagaat tattttaaat                                              20

<210> SEQ ID NO 1267
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1267
ggaagttgta taatagattg                                              20

<210> SEQ ID NO 1268
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1268
aattagtggg gttattagag                                              20

<210> SEQ ID NO 1269
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1269
gatttaattg ttagtagttt                                              20

<210> SEQ ID NO 1270
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1270
tatggtatta tttagtaggt                                              20

<210> SEQ ID NO 1271
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
```

HERV-K element

<400> SEQUENCE: 1271
gaaagaggga gtaaaatagt                                              20

<210> SEQ ID NO 1272
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1272
gaattgatgg ggtataagaa                                              20

<210> SEQ ID NO 1273
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1273
taagtattaa tgtaaaatga                                              20

<210> SEQ ID NO 1274
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1274
agagtttggg aaaaaattta                                              20

<210> SEQ ID NO 1275
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1275
atagtaagat aaggtttaaa                                              20

<210> SEQ ID NO 1276
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1276
gatgtaattt tagagtatgt                                              20

<210> SEQ ID NO 1277
<211> LENGTH: 20

-continued

<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1277
atattgggtt agttaatgtt                                         20

<210> SEQ ID NO 1278
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1278
ataaaaaatt tttataggag                                         20

<210> SEQ ID NO 1279
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1279
ttagaagtgt attaaagtat                                         20

<210> SEQ ID NO 1280
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1280
tggtttatat agggttaaaa                                         20

<210> SEQ ID NO 1281
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1281
ttagttatat ggatggataa                                         20

<210> SEQ ID NO 1282
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1282
gatttaattt ttaattggta                                           20

<210> SEQ ID NO 1283
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1283
atattttgat tgaaatatta                                           20

<210> SEQ ID NO 1284
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1284
gagtattatt gggatatggt                                           20

<210> SEQ ID NO 1285
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1285
ttatgattat aaattttata                                           20

<210> SEQ ID NO 1286
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1286
agtagatata ggagatttta                                           20

<210> SEQ ID NO 1287
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1287
tttgtttagg aaagttaggt                                           20

<210> SEQ ID NO 1288
<211> LENGTH: 20
<212> TYPE: DNA
<213> ORGANISM: Artificial
<220> FEATURE:
<223> OTHER INFORMATION: Sequence-identical and complementary primer sequence specific for the bisulfite-converted sense strand of the
HERV-K element

<400> SEQUENCE: 1288
tttattgaga tagggaaaaa				20

<210> SEQ ID NO 1289
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1289
ataaatatta agggaattta				20

<210> SEQ ID NO 1290
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1290
cttaatattt attaatcatt				20

<210> SEQ ID NO 1291
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1291
tacatacaca taaacatctc				20

<210> SEQ ID NO 1292
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1292
ttccctatct caataaataa				20

<210> SEQ ID NO 1293
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1293
aacattccat tacccaaaaa				20

<210> SEQ ID NO 1294

-continued

<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1294
ctcacataaa aaaaaacctt                                              20

<210> SEQ ID NO 1295
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1295
taaaaaataa taataactct                                              20

<210> SEQ ID NO 1296
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1296
tccatttaac ccaaaattta                                              20

<210> SEQ ID NO 1297
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1297
aacaaaaaaa tttttcttaa                                              20

<210> SEQ ID NO 1298
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1298
actaacaaca aacaaaacaa                                              20

<210> SEQ ID NO 1299
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1299
tcctaacacc aaatttaaat                                          20

<210> SEQ ID NO 1300
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1300
ctaaaataaa attatcttct                                          20

<210> SEQ ID NO 1301
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1301
tattctaaaa tcataaacct                                          20

<210> SEQ ID NO 1302
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1302
aacttaccaa tttttaatca                                          20

<210> SEQ ID NO 1303
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1303
aatcaaaata taaataaata                                          20

<210> SEQ ID NO 1304
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1304
aactaattta ataactatat                                          20

<210> SEQ ID NO 1305
<211> LENGTH: 20
<212> TYPE: DNA
<213> ORGANISM: Artificial
<220> FEATURE:

-continued

```
<223> OTHER INFORMATION: Sequence-identical and complementary primer
      sequence specific for the bisulfite-converted sense strand of the
      HERV-K element

<400> SEQUENCE: 1305
tatacttata tttatctaaa                                                 20

<210> SEQ ID NO 1306
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1306
cttaaaacaa attttccctt                                                 20

<210> SEQ ID NO 1307
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1307
catcctaata ctctccctaa                                                 20

<210> SEQ ID NO 1308
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1308
cattataaaa cttcaaatat                                                 20

<210> SEQ ID NO 1309
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1309
taaaattttc cactaactta                                                 20

<210> SEQ ID NO 1310
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1310
cattactaaa accatcaata                                                 20
```

<210> SEQ ID NO 1311
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1311
tttactaata aatataaaac                                              20

<210> SEQ ID NO 1312
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1312
atataaaatc tcaatacttt                                              20

<210> SEQ ID NO 1313
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1313
aaccttaata tataacaaaa                                              20

<210> SEQ ID NO 1314
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1314 aactcccta aaaacaaaaa                                               20

<210> SEQ ID NO 1315
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1315
ctctacctat tattataata                                              20

<210> SEQ ID NO 1316
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

```
<400> SEQUENCE: 1316
tctaaaatta catctaatcc                                               20

<210> SEQ ID NO 1317
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1317
accctaccta ctaaataata                                               20

<210> SEQ ID NO 1318
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1318
acctcctata attaattata                                               20

<210> SEQ ID NO 1319
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1319
attttaataa aactaaaata                                               20

<210> SEQ ID NO 1320
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1320
cataaacaaa ataaaaaatt                                               20

<210> SEQ ID NO 1321
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1321
ctaatcctcc tcaacacaaa                                               20

<210> SEQ ID NO 1322
<211> LENGTH: 20
<212> TYPE: DNA
<213> ORGANISM: Artificial
```

```
-continued

<220> FEATURE:
<223> OTHER INFORMATION: Sequence-identical and complementary primer
      sequence specific for the bisulfite-converted sense strand of the
      HERV-K element

<400> SEQUENCE: 1322
ccttcaaaca tctatttaac                                                   20

<210> SEQ ID NO 1323
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted sense strand of the
      HERV-K element

<400> SEQUENCE: 1323
ttaacaacat ctcaaaacaa                                                   20

<210> SEQ ID NO 1324
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1324 tttttagta tttattgatt                                                    20

<210> SEQ ID NO 1325
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1325
ggggatgtgt tagggttata                                                   20

<210> SEQ ID NO 1326
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1326
tgtattatag ataaggtaaa                                                   20

<210> SEQ ID NO 1327
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1327
atatgtatat atataaatat                                                   20
```

<210> SEQ ID NO 1328
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1328 tttttttta ttttagtaga                                          20

<210> SEQ ID NO 1329
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1329
gatgtttttt tttttttta                                          20

<210> SEQ ID NO 1330
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1330
ggatggttag gtttttttt                                          20

<210> SEQ ID NO 1331
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1331
agattaggga gtggtgatga                                         20

<210> SEQ ID NO 1332
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1332
ttgatatagt atatgtttta                                         20

<210> SEQ ID NO 1333
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element -continued

<400> SEQUENCE: 1333
gattaatagt attttaaggt                                              20

<210> SEQ ID NO 1334
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1334
gtaataattt tattttttt                                               20

<210> SEQ ID NO 1335
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1335
gatttataat tatagtattt                                              20

<210> SEQ ID NO 1336
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1336 aattttgta attgttttag                                               20

<210> SEQ ID NO 1337
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1337
tggaaatgtt taaagtgaga                                              20

<210> SEQ ID NO 1338
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1338
gtttagattt attataaatt                                              20

<210> SEQ ID NO 1339
<211> LENGTH: 20
<212> TYPE: DNA

```
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1339
ttgtaattaa agtaaaaatg                                              20

<210> SEQ ID NO 1340
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1340
ggtttaataa ttatattttt                                              20

<210> SEQ ID NO 1341
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1341
ttttggggta gagattttttt                                             20

<210> SEQ ID NO 1342
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1342
ttgagtaatt gtggtagaat                                              20

<210> SEQ ID NO 1343
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1343
ttaaattaaa attttttgtat                                             20

<210> SEQ ID NO 1344
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1344
gataagtgaa tttattgtta                                              20
```

<210> SEQ ID NO 1345
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1345
aggtattaaa tattttggtg                                              20

<210> SEQ ID NO 1346
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1346
tatttttata ggattattta                                              20

<210> SEQ ID NO 1347
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1347
attttaaatg tttagtgggt                                              20

<210> SEQ ID NO 1348
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1348
tattttttat gttttatttt                                              20

<210> SEQ ID NO 1349
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1349
gttagattaa gttgtatttg                                              20

<210> SEQ ID NO 1350
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of -continued the HERV-K element

<400> SEQUENCE: 1350
agttgtatat atgaaatgtg                                       20

<210> SEQ ID NO 1351
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1351
ttttaatatt ttttgtagtt                                       20

<210> SEQ ID NO 1352
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1352
gttatttttt tattgttgga                                       20

<210> SEQ ID NO 1353
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1353
ttattttgtt tgggttattt                                       20

<210> SEQ ID NO 1354
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1354 tatttttag taatttttga                                        20

<210> SEQ ID NO 1355
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1355 gattttttt gaattataaa                                        20

<210> SEQ ID NO 1356
<211> LENGTH: 20

```
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1356
tttattttgg ttataatttt                                              20

<210> SEQ ID NO 1357
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1357
ggttttaagt aatgtaaaat                                              20

<210> SEQ ID NO 1358
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1358
aattttttaa gttgtttttt                                              20

<210> SEQ ID NO 1359
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1359
ttttaatata tggtaggagt                                              20

<210> SEQ ID NO 1360
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1360
aagattagtt ttatagtttt                                              20

<210> SEQ ID NO 1361
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1361
```

-continued ttaaatttag aatgatattg					20

<210> SEQ ID NO 1362
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1362
tgtttgggtt ataagtatag					20

<210> SEQ ID NO 1363
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1363
gtttttttga attttgtttt					20

<210> SEQ ID NO 1364
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1364
atagttgatt tgtatttatg					20

<210> SEQ ID NO 1365
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1365
tattgtttta ttttttttt					20

<210> SEQ ID NO 1366
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1366
gattttttaa taattttatg					20

<210> SEQ ID NO 1367
<211> LENGTH: 20
<212> TYPE: DNA
<213> ORGANISM: Artificial
<220> FEATURE:
<223> OTHER INFORMATION: Sequence-identical and complementary primer sequence specific for the bisulfite-converted antisense strand of
      the HERV-K element

<400> SEQUENCE: 1367
aaatggtttt aaagttgttt                                             20

<210> SEQ ID NO 1368
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1368
tttttatatt tgtgggtgtt                                             20

<210> SEQ ID NO 1369
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1369
taatagtggg gagagggtga                                             20

<210> SEQ ID NO 1370
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1370
ggaaatagat gtttttttttt                                            20

<210> SEQ ID NO 1371
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1371
tttgagatta gggagtggtg                                             20

<210> SEQ ID NO 1372
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1372
atctataacc ttacccccaa                                             20

<210> SEQ ID NO 1373

<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1373
aacaaatact taaaaacaac                                              20

<210> SEQ ID NO 1374
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1374
aatctcaaat acccaaaaac                                              20

<210> SEQ ID NO 1375
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1375
tccccatata aaaatctaaa                                              20

<210> SEQ ID NO 1376
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1376
aaaaaaaatt aatataaaaa                                              20

<210> SEQ ID NO 1377
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1377
caccttaaaa ctaaaaataa                                              20

<210> SEQ ID NO 1378
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1378
cacatctccc tctcaaaaaa                                                20

<210> SEQ ID NO 1379
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1379
tttttctttt ccaaatctct                                                20

<210> SEQ ID NO 1380
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1380
tttctctaaa ataaaaatac                                                20

<210> SEQ ID NO 1381
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1381
cttaacttca ttaaaattct                                                20

<210> SEQ ID NO 1382
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1382
aacaaataaa aaaaataata                                                20

<210> SEQ ID NO 1383
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1383
aattacaaaa aataatatat                                                20

<210> SEQ ID NO 1384
<211> LENGTH: 20
<212> TYPE: DNA
<213> ORGANISM: Artificial
<220> FEATURE:

```
<223> OTHER INFORMATION: Sequence-identical and complementary primer
      sequence specific for the bisulfite-converted antisense strand of
      the HERV-K element

<400> SEQUENCE: 1384
ccaactacca ataacttatc                                              20

<210> SEQ ID NO 1385
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1385
aataaacaaa ataataaatt                                              20

<210> SEQ ID NO 1386
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1386
ccaaataaaa atctttttaa                                              20

<210> SEQ ID NO 1387
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1387
tttacaattt aaaacttaat                                              20

<210> SEQ ID NO 1388
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1388
aattaaaact atctacctta                                              20

<210> SEQ ID NO 1389
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1389
ccattaaacc attaaaaaaa                                              20
```

<210> SEQ ID NO 1390
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1390
atcaaaataa tcatttaaaa                                            20

<210> SEQ ID NO 1391
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1391
taataaaaat aaacaaccat                                            20

<210> SEQ ID NO 1392
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1392 caaccccccac tatcccaaat                                           20

<210> SEQ ID NO 1393
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1393
ataccaatcc aaaaaacaaa                                            20

<210> SEQ ID NO 1394
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1394
aaatcaataa ccaaaaaatt                                            20

<210> SEQ ID NO 1395
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

```
<400> SEQUENCE: 1395
taaccaaaat aaaatatata                                              20

<210> SEQ ID NO 1396
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1396
taattcaaaa aaaatccaac                                              20

<210> SEQ ID NO 1397
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand
      of the HERV-K element

<400> SEQUENCE: 1397
aaaattacca atacaaaact                                              20

<210> SEQ ID NO 1398
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1398
atcccttaac cccactccaa                                              20

<210> SEQ ID NO 1399
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1399
ataaaaataa cccaaacaaa                                              20

<210> SEQ ID NO 1400
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1400
aaaaaaataa cttacacaaa                                              20

<210> SEQ ID NO 1401
<211> LENGTH: 20
<212> TYPE: DNA
<213> ORGANISM: Artificial
```

```
<220> FEATURE:
<223> OTHER INFORMATION: Sequence-identical and complementary primer
      sequence specific for the bisulfite-converted antisense strand of
      the HERV-K element

<400> SEQUENCE: 1401
aaaaaacttc ccattttata                                              20

<210> SEQ ID NO 1402
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1402
acttattcac atttcatata                                              20

<210> SEQ ID NO 1403
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1403
cacataaaaa aaaactaatt                                              20

<210> SEQ ID NO 1404
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1404
taataataat atataaatac                                              20

<210> SEQ ID NO 1405
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1405
cttatcaaaa atcattaaaa                                              20

<210> SEQ ID NO 1406
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1406
tacacaaata aatccaacta                                              20
```

<210> SEQ ID NO 1407
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1407
ctataaccta taaaaattat                                         20

<210> SEQ ID NO 1408
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1408
acaaaaaaat tctacaaaat                                         20

<210> SEQ ID NO 1409
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1409
taaatctaaa catcactaaa                                         20

<210> SEQ ID NO 1410
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1410
tattattaat ctacaaatat                                         20

<210> SEQ ID NO 1411
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1411
aaaataatac aaaatatact                                         20

<210> SEQ ID NO 1412
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1412
taatataaaa aaaaaacata                                           20

<210> SEQ ID NO 1413
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1413
actaccttaa aactaaaaat                                           20

<210> SEQ ID NO 1414
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1414
tattatctta taaccctaac                                           20

<210> SEQ ID NO 1415
<211> LENGTH: 20
<212> TYPE: DNA
<213> ORGANISM: Artificial
<220> FEATURE:
<223> OTHER INFORMATION: Sequence-identical and complementary primer
      sequence specific for the bisulfite-converted antisense strand of
      the HERV-K element

<400> SEQUENCE: 1415
tccaccttat aaaaaacacc                                           20

<210> SEQ ID NO 1416
<211> LENGTH: 420
<212> TYPE: DNA
<213> ORGANISM: Artificial
<220> FEATURE:
<223> OTHER INFORMATION: Primer

<400> SEQUENCE: 1416 gggggagga gccaagatgg ccgaatagga acagctccgg tctacagctc ccagcgtgag      60
cgacgcagaa gacggtgatt tctgcatttc catctgaggt accgggttca tctcactagg    120
gagtgccaga cagtgggcgc aggccagtgt gtgtgcgcac cgtgcgcgag ccgaagcagg    180
gcgaggcatt gcctcacctg ggaagcgcaa ggggtcaggg agttcccttt ctgagtcaaa    240
gaaaggggtg acggtcgcac ctggaaaatc gggtcactcc cacccgaata ttgcgctttt    300
cagaccggct taagaaacgg cgcaccacga gactatatcc cacacctggc tcggagggtc    360
ctacgcccac ggaatctcgc tgattgctag cacagcagtc tgagatcaaa ctgcaaggcg    420

<210> SEQ ID NO 1417
<211> LENGTH: 19
<212> TYPE: DNA
<213> ORGANISM: Artificial
<220> FEATURE:
<223> OTHER INFORMATION: Primer

```
<400> SEQUENCE: 1417
gcgcgagtcg aagtagggc                                            19

<210> SEQ ID NO 1418
<211> LENGTH: 29
<212> TYPE: DNA
<213> ORGANISM: Artificial
<220> FEATURE:
<223> OTHER INFORMATION: Primer

<400> SEQUENCE: 1418
ctccgaacca aatataaaat ataatctcg                                 29

<210> SEQ ID NO 1419
<211> LENGTH: 28
<212> TYPE: DNA
<213> ORGANISM: Artificial
<220> FEATURE:
<223> OTHER INFORMATION: Primer

<400> SEQUENCE: 1419
aggttttatt tttgggggta gggtatag                                  28

<210> SEQ ID NO 1420
<211> LENGTH: 30
<212> TYPE: DNA
<213> ORGANISM: Artificial
<220> FEATURE:
<223> OTHER INFORMATION: Primer

<400> SEQUENCE: 1420
cccctactaa aaaatacctc ccaattaaac                                30

<210> SEQ ID NO 1421
<211> LENGTH: 32
<212> TYPE: DNA
<213> ORGANISM: Artificial
<220> FEATURE:
<223> OTHER INFORMATION: Primer

<400> SEQUENCE: 1421
accctccaaa ccaaatataa aatataatct ca                             32

<210> SEQ ID NO 1422
<211> LENGTH: 32
<212> TYPE: DNA
<213> ORGANISM: Artificial
<220> FEATURE:
<223> OTHER INFORMATION: Primer

<400> SEQUENCE: 1422
accctccaaa ccaaatataa aatataatct ca                             32
```

We claim:

1. A process for determining the normalized DNA methylation level, comprising the steps:
   a) quantitatively determining the presence of a transposon or fragment thereof in a DNA wherein this quantitative determination comprises amplifying a non-bisulfited DNA with at least one primer pair that is specific for the transposon or fragment thereof, or amplifying of a bisulfited DNA with at least one primer pair that is specific for a bisulfited transposon or fragment thereof, wherein the primers do not include a differentially methylated position of the transposon;
   b) quantitatively determining the presence of at least one differentially methylated C of a CpG dinucleotide within the same transposon or fragment thereof wherein this determination comprises amplifying the bisulfited DNA with at least one primer pair that is specific for the transposon or fragment thereof, and that includes at least one primer comprising at least one differentially methylated position of the transposon; and
   c) determining the normalized DNA methylation level via the values determined in steps a) and b) wherein this determination comprises determining the normalized DNA methylation level via the ratio of the amplificates formed in steps a) and b), wherein the same amounts of DNA are employed in steps a) and b), having been isolated from one sample, wherein the primer pair in step a) and the primer pair in step b) are selected so that a first amplifying region in step a) and a second amplifying region in step b) have a distance of ≤6000 bp apart on the transposon.

2. The process according to claim 1, wherein said transposon or fragment thereof is selected from the group consisting of a LINE element, a LINE-1 element, an Alu element, and a HERV element.

3. The process according to claim 1, wherein both primers of the primer pair in step b) include at least one differentially methylated position of the transposon.

4. The process according to claim 1, wherein the at least one primer in step b) includes 2, 3 or 4 differentially methylated positions of the transposon.

5. The process according to claim 1, wherein the at least one primer in step b has a differentially methylated position of the transposon at its 3' end.

6. The process according to claim 1, wherein said at least one primer in step b) includes an oligonucleotide selected from the group consisting of SEQ ID Nos. 3 to 1048.

7. The process according to claim 1, wherein said amplification in steps a) and b) is performed by means of real time PCR.

8. The process according to claim 7, wherein a relative quantification is conducted in the real time PCR.

9. The process according to claim 7, wherein cycle threshold values are determined in step a) and step b) and the normalized methylation level is derived from said cycle threshold values.

10. The process according to claim 1, wherein at least one oligonucleotide selected from the group consisting of SEQ ID No. 3 to SEQ ID No. 1415 is used for determining the normalized DNA methylation level.

11. The process according to claim 1, wherein said transposon or fragment thereof is the promoter region of a LINE-1 element.

12. A process for determining the relative DNA methylation level, comprising the steps:

determining the normalized methylation level according to steps a) to c) according to claim 1 for a first DNA and a second DNA; and determining the relative DNA methylation level via the ratio of the methylation levels determined for the first and second DNAs.

13. The process according to claim 12, wherein said first DNA is a reference sample and said second DNA originates from a sample to be examined and further comprising using the determined relative methylation level for the diagnosis of a disease related to altered DNA methylation.

14. The process according to claim 13, wherein said disease is the presence of a tumor.

15. A process for determining the normalized DNA methylation level, comprising the steps:
a) quantitatively determining in a real-time PCR the presence of a transposon or fragment thereof in a DNA wherein this quantitative determination comprises amplifying a non-bisulfited DNA with at least one primer pair that is specific for the transposon or fragment thereof, or amplifying of a bisulfited DNA with at least one primer pair that is specific for a bisulfited transposon or fragment thereof, wherein the primers do not include a differentially methylated position of the transposon;
b) quantitatively determining in a real-time PCR the presence of at least one differentially methylated C of a CpG dinucleotide within the same transposon or fragment thereof wherein this determination comprises amplifying the bisulfited DNA with at least one primer pair that is specific for the transposon or fragment thereof, and that includes at least one primer comprising at least one differentially methylated position of the transposon; and
c) determining the normalized DNA methylation level via the values determined in steps a) and b) wherein this determination comprises determining the normalized DNA methylation level via the ratio of the amplificates formed in steps a) and b),
wherein the same amounts of DNA are employed in steps a) and b), having been isolated from one sample, wherein a relative quantification is conducted in the real time PCR.

* * * * *